United States Patent
Dave et al.

(10) Patent No.: US 9,969,731 B2
(45) Date of Patent: May 15, 2018

(54) HETEROCYCLYL COMPOUNDS AS MEK INHIBITORS

(71) Applicant: LUPIN LIMITED, Mumbai (IN)

(72) Inventors: Bhavesh Dave, Pune (IN); Rakesh Kumar Banerjee, Pune (IN); Samiron Phukan, Pune (IN); Abhijit Datta Khoje, Pune (IN); Rajkumar Hangarge, Pune (IN); Jitendra Sambhaji Jadhav, Pune (IN); Venkata P. Palle, Pune (IN); Rajender Kumar Kamboj, Pune (IN)

(73) Assignee: Lupin Limited, Mumbai (IN)

( * ) Notice: Subject to any disclaimer, the term of this patent is extended or adjusted under 35 U.S.C. 154(b) by 0 days. days.

(21) Appl. No.: 15/388,327

(22) Filed: Dec. 22, 2016

(65) Prior Publication Data

US 2017/0101408 A1 Apr. 13, 2017

Related U.S. Application Data

(63) Continuation of application No. 15/218,980, filed on Jul. 25, 2016, now Pat. No. 9,555,035, which is a continuation of application No. 14/385,092, filed as application No. PCT/IB2013/051908 on Mar. 11, 2013, now Pat. No. 9,428,499.

(30) Foreign Application Priority Data

Mar. 14, 2012 (IN) .............................. 288/KOL/2012

(51) Int. Cl.
| | |
|---|---|
| C07D 471/04 | (2006.01) |
| A61K 45/06 | (2006.01) |
| A61K 31/519 | (2006.01) |
| A61K 31/5377 | (2006.01) |
| A61K 31/541 | (2006.01) |

(52) U.S. Cl.
CPC .......... C07D 471/04 (2013.01); A61K 31/519 (2013.01); A61K 31/5377 (2013.01); A61K 31/541 (2013.01); A61K 45/06 (2013.01)

(58) Field of Classification Search
CPC .................................................. C07D 471/04
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,837,028 A | 6/1989 | Allen et al. | |
| 5,019,369 A | 5/1991 | Presant et al. | |
| 7,378,423 B2 * | 5/2008 | Kawasaki | C07D 471/04 514/234.2 |
| 9,428,499 B2 * | 8/2016 | Dave | C07D 471/04 |
| 9,555,035 B2 * | 1/2017 | Dave | C07D 471/04 |
| 2006/0014768 A1 | 1/2006 | Kawasaki et al. | |
| 2015/0299186 A1 | 10/2015 | Dave et al. | |

FOREIGN PATENT DOCUMENTS

| | | |
|---|---|---|
| WO | 03/053960 A1 | 7/2003 |
| WO | 2005/023251 A1 | 3/2005 |
| WO | 2005/051906 A1 | 6/2005 |
| WO | 2005/121142 A1 | 12/2005 |
| WO | 2010/121646 A1 | 10/2010 |

OTHER PUBLICATIONS

International Search Report for corresponding Application No. PCT/IB2013/051908, dated May 7, 2013.
Hanahan et al., "The Hallmarks of Cancer", Cell, Jan. 7, 2000, vol. 100, pp. 57-70.
Hanahan et al., "Hallmarks of Cancer: The Next Generation", Cell, Mar. 4, 2011, vol. 144, pp. 646-674.
Sebolt-Leopold et al., "Targeting the Mitogen-activated Protein Kinase Cascade to Treat Cancer", Nature Reviews, Cancer, Dec. 2004, vol. 4, pp. 937-947.
Fukazawa et al., "Mitogen-activated Protein/Extracellular Signal-regulated Kinase Kinase (MEK) Inhibitors Restore Anoikis Sensitivity in Human Breast Cancer Cell Lines with a Constitutively Activated Extracellular-regulated Kinase (ERK) Pathway", Molecular Cancer Therapeutics, Mar. 2002, vol. 1, pp. 303-309.
McCubrey et al., "Targeting the Raf/MEK/ERK pathway with small-molecule inhibitors", Current Opinion in Investigational Drugs, 2008, vol. 9., No. 6, pp. 614-630.
Kyriakis et al., "Sounding the Alarm: Protein Kinase Cascades Activated by Stress and Inflammation", The Journal of Biological Chemistry, 1996, vol. 271, No. 40, pp. 24313-24316.

(Continued)

*Primary Examiner* — Paul V Ward
(74) *Attorney, Agent, or Firm* — Melissa M. Hayworth; Daniel R. Evans; E. Joseph Gess

(57) ABSTRACT

The present disclosure is related to heteroaryl compounds as MEK inhibitors. These compounds include heteroaryl compounds of formula I, their pharmaceutically acceptable salts, combinations with suitable medicament and pharmaceutical compositions thereof. The present disclosure also includes processes of preparation of the compounds and their use in methods of treatment. The compounds as disclosed herein are of Formula (I) below:

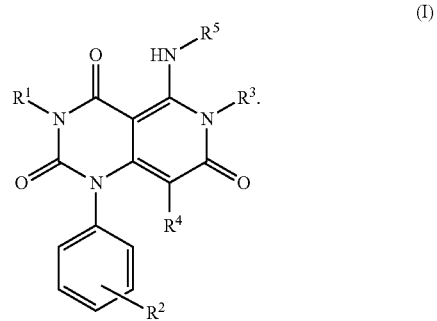

17 Claims, No Drawings

(56) References Cited

OTHER PUBLICATIONS

Hammaker et al., "Regulation of c-Jun N-Terminal Kinase by MEKK-2 and Mitogen-Activated Protein Kinase Kinase Kinases in Rheumatoid Arthritis", The Journal of Immunology, 2004, vol. 172, pp. 1612-1618.
Berge et al., "Pharmaceutical Salts", Review article in Journal of Pharmaceutical Sciences, Jan. 1977, vol. 66, No. 1, pp. 1-19.
Remington's Pharmaceutical Sciences, 18th Edition, Mack Publishing Company, Easton, PA, 1990, p. 1445.
G. Banker, "Pharmaceutics and Pharmacy Practice", J.B. Lippincott Company, Philadelphia, PA, 1982, pp. 238-250.
L. A. Trissel, "Injectable Drugs", 4th Edition, ASHP Handbook, Sep. 1986, pp. 622-630.
Remington's Pharmaceutical Sciences, 17th Edition, Chapter 85 and 86, Mack Publishing Company, Easton, PA, 1985, pp. 1518-1552.
F. Szoka, Jr, "Comparative Properties and Methods of Preparation of Lipid Vesicles (Liposomes)", Ann. Rev. Biophys. Bioeng., 1980, vol. 9, pp. 467-508.
Physician's Desk Reference, 58th Edition, Thomson PDR, 2004.
Wasserman et al. "Clinical Comparison of the Nitrosoureas", Cancer, 1975, vol. 36, pp. 1258-1268.
Stahl et al., "Handbook of Pharmaceutical Salts Properties, Selection, and Use", WILEY-VCH, 2002.
B. Zheng et al., "MEK/ERK pathway is aberrantly active in Hodgkin disease: a signaling pathway shared by CD30, CD40, and RANK that regulates cell proliferation and survival", Blood, 2003, vol. 102, No. 3, pp. 1019-1027.
M. K. Kießling et al., "High-throughput mutation profiling of CTCL samples reveals KRAS and NRAS mutations sensitizing tumors toward inhibitions of the RAS/RAF/MEK signaling cascade", Blood, 2011, vol. 117, No. 8, pp. 2433-2441.
S. Bhalla et al., "The novel anti-MEK small molecule AZD6244 induces BIM-dependent and AKT-independent apoptosis in diffuse large B-cell lymphoma", Blood, 2011, vol. 118, No. 4, pp. 1052-1062.
T. K. Nguyen et al., "Inhibition of MEK/ERK1/2 Sensitizes Lymphoma Cells to Sorafenib-Induced Apoptosis", Leuk. Res., 2010, vol. 34, No. 3, pp. 379-386.
F. Marampon et al., "MEKs/ERKs inhibitor U0126 increases the radiosensitivity of rhabdomyosarcoma cells in vitro and in vivo by down regulating growth and DNA repair signals", Molecular Cancer Therapeutics, 2011, vol. 10, No. 1, pp. 159-168.
F. Marampon et al., "MEK/ERK inhibitor U0126 affects in vitro and in vivo growth of embryonal rhabdomyosarcoma", Molecular Cancer Therapeutics, 2009, vol. 8, No. 3, pp. 543-552.
R. D. Dodd et al., "NF1 Deletion Generates Multiple Subtypes of Soft-Tissue Sarcoma That Respond to MEK Inhibition", Molecular Cancer Therapeutics, 2013, vol. 12, No. 9, pp. 1906-1918.
CH. Chandhanayingyong et al., "MAPK/ERK Signaling in Osteosarcomas, Ewing Sarcomas and Chondrosarcomas: Therapeutic Implications and Future Directions", Sarcoma, 2012, vol. 2012, pp. 1-8.
V. Pettirossi et al., "Targeting the BRAF-MEK-ERK Pathway in Hairy Cell Leukemia", Blood, 2013, vol. 122, No. 21, 2 pages.
E. Tiacci et al. "Targeting Mutant BRAF in Relapsed or Refractory Hairy-Cell Leukemia", The New England Journal of Medicine, 2015, pp. 1-15.
N. Jain et al., "Phase II Study of the Oral Mek Inhibitor Selumetinib in Advanced Acute Myeloid Leukemia (AML): A University of Chicago Phase II Consortium Trial", Clin. Cancer Res., 2014, vol. 20, No. 2, pp. 490-498.
S. B. Cheepala et al., "Identification of the B-Raf/Mek/Erk MAP kinase pathway as a target for all-trans retinoic acid during skin cancer promotoin", Molecular Cancer, 2009, vol. 8, No. 27, pp. 1-16.
C. J. Heuck et al., "Inhibiting MEK in MAPK pathway-activated myeloma", Leukemia, 2015, pp. 1-4.

M. Milella et al., "Theraupetic targeting of the MEK/MAPK signal transduction module in acute myeloid leukemia", J. Clin., Invest., 2001, vol. 108, pp. 851-859.
Y. C. Henderson et al., "MEK Inhibitor PD0325901 Significantly Reduces the Growth of Papillary Thyroid carcinoma Cells In vitro and In vivo", Mol. Cancer Ther., 2010, vol. 9, No. 7, pp. 1968-1976.
D. Liu et al., "Potent Inhibition of Thyroid Cancer Cells by the MEK Inhibitor PD0325901 and Its Potentiation by Suppression of the PI3K and NF-kB Pathways", Thyroid, 2008, vol. 18, No. 8, pp. 853-864.
H. Pan et al., "Modulation of Kaposi's Sarcoma-Associated Herpesvirus Infection and Replication by MEK/ERK, JNK, and p38 Multiple Mitogen-Activated Protein Kinase Pathways during Primary Infection", Journal of Virology, 2006, vol. 80, No. 11, pp. 5371-5382.
P. P. Naranatt et al., "Kaposi's Sarcoma-Associated Herpesvirus Induces the Phosphatidylinositol 3-Kinase-PKC-_-MEK-ERK Signaling Pathway in Target Cells Early during Infection: Implications for Infectivity", Journal of Virology, 2003, vol. 77, No. 2, pp. 1524-1539.
A. Weber et al., "Mutations of the BRAF gene in squamous cell carcinoma of the head and neck", Oncogene, 20013, vol. 22, pp. 4757-4759.
L. R. Kong et al., "MEK Inhibition Overcomes Cisplatin Resistance Conferred by SOS/MAPK Pathway Activation in Squamous Cell Carcinoma", Molecular Cancer Therapeutics, 2015, vol. 14, No. 7, pp. 1750-1761.
I. M. Subbiah et al., "Targeted Therapy of Advanced Gallbladder Cancer and Cholangiocarcinoma with Aggressive Biology: Eliciting Early Response Signals from Phase 1 trials", Oncotarget, 2013, vol. 1, No. 1, pp. 153-162.
R.-R. Liang et al., "Preferential inhibition of hepatocellular carcinoma by the flavonoid Baicelein through blocking MEK-ERK signaling", International Journal of Oncology, 2012, Vo. 41, pp. 969-978.
C. A. Wiesenauer et al., "Multiple Anticancer Effects of Blocking MEK-ERK Signaling in Hepatocellular Carcinoma", MEK-ERK Signaling in Hepatocellular Carcinoma, 2004, vol. 198, No. 3, pp. 410-421.
J. S. Khalili et al., "Combination Small Molecule MEK and PI3K Inhibition Enhances Uveal Melanoma Cell Death in a Mutant GNAQ and GNA11 Dependent Manner", Clinical Cancer Research, 2012, vol. 18, No. 16, pp. 4345-4355.
X. Chen et al., "Combined PKC and MEK inhibition in uveal melanoma with GNAQ and GNA11 mutations", Oncogene, 2014, vol. 33, pp. 4724-4734.
A. P. Fay et al., "MET as a Target in Papillary Renal Cell Carcinoma", Clinical Cancer Research, 2014, vol. 20, No. 13, pp. 3361-3364.
S.T. Bailey et al., "mTOR Inhibition Induces Compensatory, Therapeutically Targetable MEK Activation in Renal Cell carcinoma", Plos One, 2014, vol. 9., Issue 9, pp. 1-11.
I. Ahmad et al., "Exploring molecular genetics of bladder cancer: lessons learned from mouse models", Disease Models & Mechanisms, 2012, vol. 5, pp. 323-332.
H. Hamakawa et al., "Basic evidence of molecular targeted therapy for oral cancer and salivary gland cancer", Clinical Review, Head & Neck—DOI, 2008. pp. 800-809.
I. Hofmann et al., "K-RAS Mutant Pancreatic Tumors Show Higher Sensitivity to MEK than to PI3K Inhibition In Vivo", Plos One, 2012, vol. 7., Issue 8, pp. 1-14.
D. M. Walters et al., "Inhibition of the Growth of Patient-Derived Pancreatic Cancer Xenografts with the MEK Inhibitor Trametinib is Augmented by Combined Treatment with the Epidermal Growth Factor Receptor/HER2 Inhibitor Lapatinib1,2", Neoplasia, 2013, vol. 15, No. 2, pp. 143-155.
H. Horiuchi et al., "A MEK Inhibitor (U0126) Markedly Inhibits Direct Liver Invasion of Orthotopically Inoculated Human Gallbladder Cancer Cells in Nude Mice", J. Exp. Clin. Cancer Res., 2004, vol. 23, No. 4, pp. 599-606.
S. Sogabe et al., "MEK Inhibitor for Gastric Cancer with MEK1 Gene Mutations", Molecular Cancer Therapeutics, 2014, vol. 13, No. 12, pp. 3098-3106.

(56) References Cited

OTHER PUBLICATIONS

C. Fremin et al., "From basic research to clinical development of MEK1/2 inhibitors for cancer therapy", Journal of Hematology & Oncology, 2010, vol. 3, No. 8, pp. 1-11.
R. R. Keld et al., "Targeting key signalling pathways in oesophageal adenocarcinoma: A reality for personalised medicine?", World Journal of Gastroenterology, 2011, vol. 17, No. 23, pp. 2781-2790.
M. R. Maiello et al., "EGFR and MEK Blockade in Triple Negative Breast Cancer Cells", Journal of Cellular Biochemistry, 2015, vol. 116, pp. 2778-2785.
P. J. Roberts et al., "Targeting the Raf-MEK-ERK mitogen-activated protein kinase cascade for the treatment of cancer", Oncogene, 2007, vol. 26, pp. 3291-3310.
C. C. Gomes et al., "BRAFV600E Mutation in Melanotic Neuroectodermal Tumor of Infancy: Toward Personalized Medicine?", Pediatrics, 2015, vol. 136, No. 1, pp. e267-e269.
T. J. MacDonald et al., "The rationale for targeted therapies in medulloblastoma", Neuro-Oncology, 2014, vol. 16, No. 1, pp. 9-20.
W. L. See et al., "Sensitivity of Glioblastomas to Clinically Available MEK Inhibitors is Defined by Neurofibromin 1 Deficiency", Cancer Research, 2012, vol. 72, No. 13, pp. OF1-OF10.
V. R. Torti et al., "Epithelial Tissue Hyperplasia Induced by the RAF Inhibitor PF-04880594 is Attenuated by a Clinically Well-Tolerated Dose of the MEK Inhibitor PD-0325901", Molecular Cancer Therapeutics, 2012, vol. 11, No. 10, pp. 2274-2283.
F. A. Scholl et al., "Mek1/2 gene dosage determines tissue response to oncogenic Ras signaling in the skin", Oncogene, 2009, vol. 28, pp. 1485-1495.
I. J. Lim et al., "Synchronous Activation of ERK and Phosphatidylinositol 3-Kinase Pathways is Required for Collagen and Extracellular Matrix Production in Keloids", The Journal of Biological Chemistry, 2003, vol. 278, No. 42, pp. 40851-40858.
M. Peric et al., "IL-17A Enhances Vitamin D3-Induced Expression of Cathelicidin Antimicrobial Peptide in Human Keratinocytes1", The Journal of Immunology, 2008, pp. 8504-8512.
Andrew Leask, "MEK/ERK inhibitors: proof-of-concept studies in lung fibrosis", J. Cell Commun. Signal., 2012, vol. 6, pp. 59-60.
S. Namura et al., "Intravenous administration of MEK inhibitor U0126 affords brain protection against forebrain ischema and focal cerebral ischemia", PNAS, 2001, vol. 98, No. 20, pp. 11569-11574.
N. Farrokhnia et al., "MEK-inhibitor U0126 in hyperglycaemic focal ischaemic brain injury in the rat", European Journal of Clinical Investigation, 2008, vol. 38, No. 9, pp. 679-685.
A. Gladbach et al., "ERK inhibition with PD184164 mitigates brain damage in a mouse model of stroke", J. Neural. Transm., 2013, 5 pages.
J. L. Rogers et al., "Cellular Targeting in Autoimmunity", Curr. Allergy Asthma Rep., 2012, vol. 12, No. 6, pp. 495-510.
J. Guo et al., "Constitutive Activation of MEK1 Promotes Treg Cell Instability in Vivo", Journal of Biological Chemistry, 2014, vol. 289, No. 51, pp. 35139-35148.
B. D. Jaffee et al., "Inhibition of MAP Kinase Kinase (MEK) Results in an Anti-inflammatory Response in Vivo", Biochemical and Biophysical Research Communications, 2000, vol. 268, pp. 647-651.
H. M. Pinedo et al., "Translational Research: The Role of VEGF in Tumor Angiogenesis", The Oncologist, 2000, vol. 5 (suppl 1), pp. 1-2.
Gerald McMahon, "VEGF Receptor Signaling in Tumor Angiogenesis", The Oncologist, 2000, vol. 5 (suppl 1), pp. 3-10.

* cited by examiner

HETEROCYCLYL COMPOUNDS AS MEK INHIBITORS

CROSS-REFERENCE TO A RELATED APPLICATION

This application is a Continuation of U.S. patent application Ser. No. 15/218,980, filed on Jul. 25, 2016, which is a Continuation of U.S. patent application Ser. No. 14/385,092, filed on Dec. 11, 2014, now U.S. Pat. No. 9,428,499, which is the U.S. National Stage filing of PCT/IB2013/051908 filed on Mar. 11, 2013, which claims the benefit of Indian Provisional Patent Application No. 0288/KOL/2012 filed Mar. 14, 2012, the disclosures of each of which are herein incorporated by reference in their entirety.

FIELD OF THE INVENTION

The present invention relates to anticancer compounds, their pharmaceutically acceptable salts, combinations with suitable medicament and pharmaceutical compositions thereof containing one or more such compounds, and methods of treating various cancers.

BACKGROUND OF THE INVENTION

Cancer cells possess certain characteristics that allow them a growth advantage. These include six main alterations in cell physiology such as self-sufficiency in growth signals, insensitivity to growth-inhibitory signals, evasion of apoptosis, indefinite proliferative potential, sustained angiogenesis, tissue invasion and metastasis (Hanahan and Weinberg, Cell, 2000, Vol. 100, 57-70). These changes are triggered by genomic instability and inflammation which generates a microenvironment conducive for tumor growth. In addition to the above mentioned traits, reprogramming of cellular energy metabolism and evasion of immune destruction has also been observed in a majority of cancers.

The enhanced survival in cancer cells is further potentiated by the presence of aberrantly activated signalling pathways. A large majority of cancers are known to have mutations in growth factor signalling cascades that lead to constitutive activation of these pathways. Such constitutive activations has been observed in growth factor receptors which include but are not limited to epidermal growth factor receptor—EGFR, fibroblast growth factor receptor—FGFR, Hepatocyte growth factor receptor—HGFR, etc. Furthermore, activating mutations have been reported in certain receptor as well as non receptor tyrosine kinases which include but are not limited to MET receptor tyrosine kinase, EGFR-tyrosine kinase, Bcr-Abl tyrosine kinase, Src tyrosine kinase etc. Activation of Ser-Thr kinases such as Ras and lipid kinases such as PI3-kinases also leads to oncogenesis. Chronic activation of the growth factor/cytokine/hormone-associated signalling leads to activation of immediate downstream components such as Src, Ras, PI3-kinase, etc. These kinases further activate effectors such as MEK, ERK, AKT, eventually leading to activation of transcription factors that endow the cells with a high proliferative potential, improved survival, subversion of metabolic pathways and inhibition of apoptosis. (Hanahan and Weinberg, Cell, 2000, Vol. 100, 57-70; Hanahan and Weinberg Cell 2011, Vol. 144, 646-674).

MEK kinase (Mitogen Activated Protein Kinase Kinase (MAPKK)) is an important component of the Ras-RAF-MEK-ERK cell survival pathway. The Ras pathway is activated by binding of growth factors, cytokines, and hormones to their cognate receptors. In cancer cells, this pathway is, however, constitutively activated and leads to increased cancer cell survival, cell proliferation, angiogenesis and metastasis. The tumors that show constitutive activation of the Ras or the MEK kinase include but are not limited to those of the colon, pancreas, breast, brain, ovary, lungs and skin (Sebolt-Leopold and Herrera, Nat. Rev. Cancer 2004, 4 937-947; Fukazawa et al., Mol. Cancer Ther. 2002, Vol. 1, 303-309). Activation of Ras (due to upstream signalling or as a result of activating point mutations in the Ras oncogene) lead to the phosphorylation and activation of Raf kinase that in turn phosphorylate and activate MEK kinase. MEK1/2 kinase phosphorylates and activates the ERK1/2 kinase (also referred to as MAP Kinase) that further phosphorylates and regulates the function of proteins such as Mcl-1, Bim and Bad that are involved in cell survival and apoptosis. Thus, activation of this phosphorylation mediated cascade leads to enhanced cell proliferation, cell survival, decreased cell death that are necessary for initiation and maintenance of the tumorigenic phenotype (Curr. Opin. Invest. Drugs, 2008, 9, 614).

The Ras-Raf-MEK-ERK cascade plays a pivotal role in survival and proliferation of cancer cells. As such, inhibition of this pathway at any of these levels would lead to the inhibition of cancer cell growth, proliferation and survival. Indeed, it has already been reported that inhibition of Ras or Raf leads to inhibition of tumor growth in animal models as well as in cancer patients. However, the success with these inhibitors has been limited to only certain types of cancers (e.g. Sorafenib which inhibits Raf kinase has been approved for renal cell carcinoma). Hence, inhibiting MEK is a novel approach towards controlling this pathway in cancer cells. Moreover, the possibility of designing allosteric inhibitors also allows enhanced selectivity that is crucial for decreasing the toxic effects associated with kinase inhibitors.

The MEK-ERK Pathway is activated in numerous inflammatory conditions (Kyriakis and Avruch, 1996, Vol. 271, No. 40, pp. 24313-24316; Hammaker et al., J. Immunol. 2004, 172, 1612-1618), including rheumatoid arthritis, inflammatory bowel disease and COPD. MEK regulates the biosynthesis of the inflammatory cytokines TNF, IL-6 and IL-1. It has been shown that MEK inhibitors interfere with the production/secretion of these cytokines. Array BioPharma has developed a first-in-class MEK inhibitor (ARRY 438162) and initiated clinical trials in rheumatoid arthritis (RA) patients.

International patent applications WO/2003/053960, WO/2005/023251, WO/2005/121142, WO/2005/051906, WO/2010/121646 describe MEK inhibitors.

BRIEF SUMMARY OF THE INVENTION

The present invention provides anticancer compounds of the general formula (I), their pharmaceutically acceptable salts, combinations with suitable medicament and pharmaceutical compositions thereof and use thereof in treating various cancers.

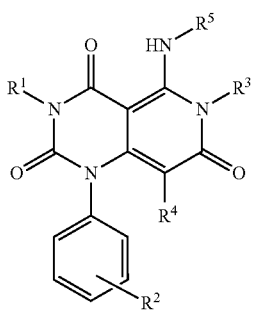

(I)

wherein, $R^1$-$R^5$ are described in detail below.

The compounds of the present inventions are potent inhibitors of MEK and show tumor regression effect with promisingly less side effects.

DETAILED DESCRIPTION OF THE INVENTION

The present invention relates to heteroaryl compounds of formula I, their pharmaceutically acceptable salts, their combinations with suitable medicament and pharmaceutical compositions thereof. The present invention also includes processes of preparation of the compounds and their use in methods of treatment. The compounds are of formula (I) below:

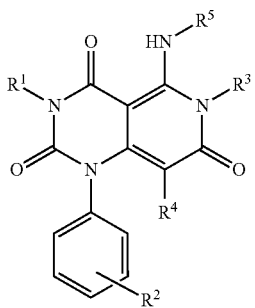

(I)

wherein:

$R^1$ is selected from the group consisting of hydrogen, substituted- or unsubstituted-alkyl, substituted- or unsubstituted-alkenyl, substituted- or unsubstituted-alkynyl, substituted- or unsubstituted-cycloalkyl, substituted- or unsubstituted-cycloalkenyl, substituted- or unsubstituted-aryl, substituted- or unsubstituted-heteroaryl, and substituted- or unsubstituted-heterocyclyl;

$R^2$ is selected from the group consisting of —(C($R^c$)($R^d$))$_m$—C(=O)—N($R^6$)$R^7$, —C(=O)N($R^8$)$R^9$, and —O—(C($R^c$)($R^d$))$_m$—C(=O)—N($R^6$)$R^7$;

$R^3$ is selected from the group consisting of hydrogen, substituted- or unsubstituted-alkyl, and substituted- or unsubstituted-cycloalkyl;

$R^4$ is selected from the group consisting of hydrogen, halogen, substituted- or unsubstituted-alkyl, and substituted- or unsubstituted-cycloalkyl;

$R^5$ is substituted- or unsubstituted-aryl, wherein the substituents are selected from the group consisting of $R^a$ and $R^b$;

$R^6$ and $R^7$ are each independently selected from the group consisting of hydrogen, substituted- or unsubstituted-alkyl, substituted- or unsubstituted-cycloalkyl, and substituted- or unsubstituted-heterocyclyl; or $R^6$ and $R^7$ taken together with the nitrogen to which they are attached form a substituted- or unsubstituted-heterocyclyl;

$R^8$ and $R^9$ are each independently selected from the group consisting of hydrogen, substituted- or unsubstituted-cycloalkyl, and substituted- or unsubstituted-heterocyclyl, or $R^8$ and $R^9$ taken together with the nitrogen to which they are attached form a substituted- or unsubstituted-heterocyclyl; with the provisos that both $R^8$ and $R^9$ cannot be hydrogen at the same time; and when $R^8$ and $R^9$ are not a part of a heterocycle formed together with the nitrogen to which they are attached, at least one of the $R^8$ and $R^9$ is substituted- or unsubstituted-cycloalkyl, or substituted- or unsubstituted-heterocyclyl;

$R^a$ and $R^b$ are each independently selected from the group consisting of hydrogen, halogen and haloalkyl;

$R^c$ and $R^d$ are independently selected from the group consisting of hydrogen, halogen, hydroxyl, and substituted- or unsubstituted-alkyl; or $R^c$ and $R^d$ taken together with the carbon to which they are attached form a substituted- or unsubstituted-cycloalkyl;

m is an integer selected from the group consisting of 1, 2, 3, and 4;

When the alkyl group or alkenyl group is substituted, the alkyl group or alkenyl group is substituted with 1 to 4 substituents independently selected from the group consisting of oxo, halogen, nitro, cyano, perhaloalkyl, cycloalkyl, aryl, heteroaryl, heterocyclyl, —SO$_2$R$^{10a}$, —C(=O)OR$^{10a}$, —OC(=O)R$^{10a}$, —C(=O)N(H)R$^{10}$, —OR$^{10b}$, —C(=O)N(alkyl)R$^{10}$, —N(H)C(=O)R$^{10a}$, —N(H)R$^{10}$, —N(alkyl)R$^{10}$—N(H)C(=O)N(H)R$^{10}$, —N(H)C(=O)N(alkyl)R$^{10}$, —NH—SO$_2$-alkyl and —NH—SO$_2$-cycloalkyl.

When the cycloalkyl group or cycloalkenyl group is substituted, the cycloalkyl group or cycloalkenyl group is substituted with 1 to 3 substituents independently selected from the group consisting of oxo, halogen, nitro, cyano, alkyl, alkenyl, perhaloalkyl, hydroxyalkyl, aryl, heteroaryl, heterocyclyl, —OR$^{10b}$, —SO$_2$R$^{10a}$, —C(=O)R$^{10a}$, —C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, and —N(H)C(=O)N(alkyl)R$^{10}$, —NH—SO$_2$-alkyl and —NH—SO$_2$-cycloalkyl.

When the aryl group is substituted, the aryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, —O— perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl and —NH—SO$_2$-cycloalkyl.

When the heteroaryl group is substituted, the heteroaryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, —O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl and —NH—SO$_2$-cycloalkyl.

When the heterocyclyl group is substituted, the heterocyclyl group is substituted with 1 to 3 substituents. When the substituents are on a ring carbon of the 'heterocycle', the substituents are independently selected from the group consisting of halogen, nitro, cyano, oxo, alkyl, alkenyl, perhaloalkyl, cycloalkyl, cycloalkenyl, aryl, heteroaryl, heterocyclyl, —OR$^{10b}$, —C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, and —N(H)C(=O)N(alkyl)R$^{10}$. When the heterocyclic group is substituted on a ring nitrogen of the 'heterocycle', the substituents are independently selected from the group consisting of alkyl, alkenyl, cycloalkyl, cycloalkenyl, aryl, heteroaryl, —SO$_2$R$^{10a}$, —C(=O)R$^{10a}$, —C(=O)OR$^{10a}$, —C(=O)N(H)R$^{10}$, —C(=O)N(alkyl)R$^{10}$, —NH—SO$_2$-alkyl and —NH—SO$_2$-cycloalkyl. When the heterocyclic group is substituted on a ring sulphur of the 'heterocycle', is the sulphur is substituted with 1 or 2 oxo groups.

R$^{10}$ is selected from the group consisting of hydrogen, alkyl, alkenyl, cycloalkyl, cycloalkenyl, aryl, heteroaryl, and heterocyclyl;

R$^{10a}$ is selected from the group consisting of alkyl, alkenyl, perhaloalkyl, cycloalkyl, cycloalkenyl, aryl, heteroaryl and heterocyclyl; and R$^{10b}$ is selected from the group consisting of hydrogen, alkyl, alkenyl, perhaloalkyl, cycloalkyl, cycloalkenyl, aryl, heteroaryl and heterocyclyl.

In certain embodiments, R$^1$ is selected from the group consisting of hydrogen, substituted- or unsubstituted-alkyl, substituted- or unsubstituted-alkenyl, substituted- or unsubstituted-heterocyclyl, and substituted- or unsubstituted-cycloalkyl.

In other embodiments, R$^1$ is selected from the group consisting of hydrogen, methyl, ethyl, isopropyl, allyl, difluoromethyl, cyclopropyl, 3-oxetanyl, —CH$_2$COOH, —CH$_2$COOC$_2$H$_5$, —CH$_2$CH(OH)CH$_2$(OH), and —C$_2$H$_4$OH.

In certain embodiments, R$^3$ and R$^4$ are substituted- or unsubstituted-alkyl.

In other embodiments, R$^3$ and R$^4$ are methyl.

In certain embodiments, R$^5$ is substituted- or unsubstituted-phenyl, wherein the substituents are independently selected from R$^a$ and R$^b$.

In certain embodiments, R$^a$ and R$^b$ are independently selected from the group consisting of hydrogen and halogen.

In other embodiments, R$^a$ and R$^b$ are independently fluorine or iodine.

In certain embodiments, R$^c$ and R$^d$ are independently selected from the group consisting of hydrogen, substituted- or unsubstituted-alkyl, halogen, and hydroxyl, or R$^c$ and R$^d$ taken together with the carbon to which they are attached form a substituted- or unsubstituted-cycloalkyl ring.

In other embodiments, R$^c$ and R$^d$ are independently selected from the group consisting of hydrogen, methyl, fluoro and hydroxyl; or R$^c$ and R$^d$ taken together with the carbon to which they are attached form a cyclopropyl ring.

In certain embodiments, m is 1 or 2.

In certain embodiments, R$^6$ and R$^7$ are independently selected from the group consisting of hydrogen, substituted- or unsubstituted-alkyl, substituted- or unsubstituted-cycloalkyl, and substituted- or unsubstituted-heterocyclyl; or R$^6$ and R$^7$ taken together with the nitrogen atom to which they are attached form a substituted- or unsubstituted-heterocycle.

In other embodiments, R$^6$ and R$^7$ are independently selected from the group consisting of hydrogen, methyl, cyclopropyl, and 3-oxetane; or R$^6$ and R$^7$ taken together with the nitrogen atom to which they are attached form azetidinyl or 3-hydroxyazetidinyl.

In certain embodiments, R$^8$ and R$^9$ are independently selected from the group consisting of hydrogen, substituted- or unsubstituted-cycloalkyl and substituted- or unsubstituted-heterocyclyl, or R$^8$ and R$^9$ taken together with the nitrogen to which they are attached form a substituted- or unsubstituted-heterocycle; with the provisos that both R$^8$ and R$^9$ are not hydrogen at the same time, and when R$^8$ and R$^9$ are not a part of a heterocycle formed together with the nitrogen to which they are attached, at least one of the R$^8$ and R$^9$ is substituted- or unsubstituted-cycloalkyl or substituted- or unsubstituted-heterocyclyl.

In other embodiments, R$^8$ and R$^9$ are independently selected from the group consisting of hydrogen, cyclopropyl, cyclopropyl substituted with —C(=O)NH$_2$ or —CH$_2$OH, 3-oxetanyl, tetrahydrofuran-3-yl, and tetrahydro-2H-pyranyl, or R$^8$ and R$^9$ together with the nitrogen to which they are attached form 1,1-dioxidothiazolidinyl, 1,1-dioxidothiomorpholinyl, morpholinyl, azetidinyl, 1-pyrrolidinyl, piperazinyl, 4-methylpiperazinyl, 3-hydroxypyrrolidinyl or 4-hydroxypiperidinyl; with the provisos that both R$^8$ and R$^9$ are not hydrogen at the same time, and when R$^8$ and R$^9$ are not a part of a heterocycle formed together with the nitrogen to which they are attached, at least one of the R$^8$ and R$^9$ is substituted- or unsubstituted-cycloalkyl or substituted- or unsubstituted-heterocyclyl.

In one embodiment, the present invention is a compound of formula Ia:

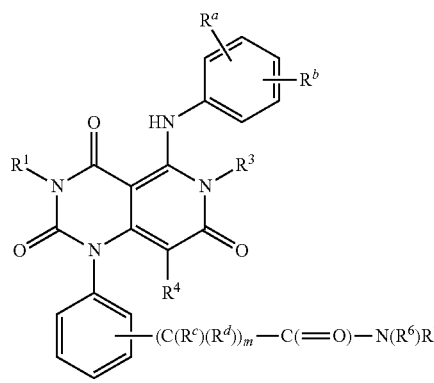

(Ia)

wherein:
R$^1$, R$^3$, R$^4$, R$^6$, R$^7$, R$^a$, R$^b$, R$^c$, R$^d$ and 'm' are as defined in formula (I).

In another embodiment, the present invention is a compound of formula (Ib):

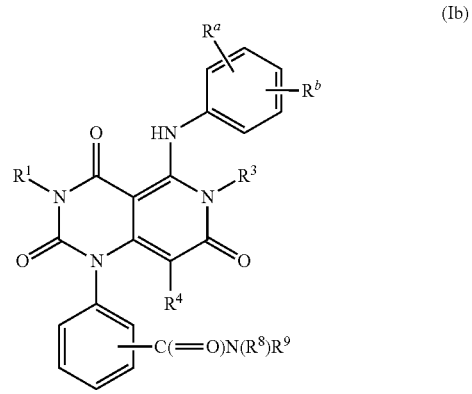

(Ib)

wherein:

R¹, R³, R⁴, R⁸, R⁹, Rᵃ and Rᵇ are as defined in formula (I); with the provisos that both R⁸ and R⁹ cannot be hydrogen at the same time, and at least one of the R⁸ and R⁹ is selected from the group consisting of substituted- or unsubstituted-aryl, substituted- or unsubstituted-cycloalkyl, substituted- or unsubstituted-cycloalkenyl, substituted- or unsubstituted-heterocyclyl; or R⁸ and R⁹ taken together with the nitrogen to which they are attached form a substituted- or unsubstituted-heterocycle.

In another embodiment, the present invention is a compound of formula (Ic):

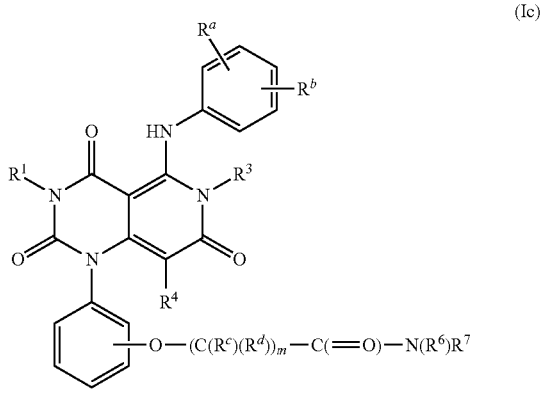

(Ic)

wherein: R¹, R³, R⁴, R⁶, R⁷, Rᵃ, Rᵇ, Rᶜ, Rᵈ and 'm' are as defined in formula (I).

General terms used in any of the formulae herein can be defined as follows; however, the meaning stated should not be interpreted as limiting the scope of the term per se.

The term "alkyl", as used herein, means a straight or branched hydrocarbyl chain containing from 1 to 20 carbon atoms. Preferably, the alkyl group contains 1 to 10 carbon atoms. More preferably, alkyl group contains up to 6 carbon atoms. Examples of alkyl groups include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkenyl" as used herein, means an 'alkyl' group as defined hereinabove containing 2 to 20 carbon atoms and containing at least one double bond. Representative examples of alkenyl include, but are not limited to, pent-2-enyl, hex-3-enyl, allyl, vinyl, and the like.

When the alkyl or alkenyl groups are substituted alkyl or substituted alkenyl groups, the alkyl or alkenyl groups are substituted with 1 to 4 substituents selected independently from the group consisting of oxo, halogen, nitro, cyano, haloalkyl, cycloalkyl, aryl, heteroaryl, heterocyclyl, —OR¹⁰ᵇ, —SO₂R¹⁰ᵃ, —C(=O)R¹⁰ᵃ, —C(=O)OR¹⁰ᵃ, —OC(=O)R¹⁰ᵃ, —C(=O)N(H)R¹⁰, —C(=O)N(alkyl)R¹⁰, —N(H)C(=O)R¹⁰ᵃ, —N(H)R¹⁰, —N(alkyl)R¹⁰, —N(H)C(=O)N(H)R¹⁰, —N(H)C(=O)N(alkyl)R¹⁰, —NH—SO₂-alkyl and —NH—SO₂-cycloalkyl; wherein, R¹⁰ is selected from the group consisting of hydrogen, alkyl, alkenyl, cycloalkyl, cycloalkenyl, aryl, heteroaryl, and heterocyclyl; R¹⁰ᵃ is selected from the group consisting of alkyl, alkenyl, haloalkyl, perhaloalkyl, cycloalkyl, cycloalkenyl, aryl, heteroaryl, heterocyclyl; R¹⁰ᵇ is selected from the group consisting of hydrogen, alkyl, alkenyl, haloalkyl, perhaloalkyl, cycloalkyl, cycloalkenyl, aryl, heteroaryl, and heterocyclyl.

The term "haloalkyl" means alkyl, as the case may be, substituted with one or more halogen atoms, where alkyl groups are as defined above. The term "halo" is used herein interchangeably with the term "halogen" and means F, Cl, Br or I. Examples of "haloalkyl" include but are not limited to trifluoromethyl, difluoromethyl, 2,2,2-trifluoroethyl, pentafluoroethyl, pentachloroethyl, 4,4,4-trifluorobutyl, 4,4-difluorocyclohexyl, chloromethyl, dichloromethyl, trichloromethyl, 1-bromoethyl and the like. The term "perhaloalkyl" group is defined hereinabove wherein all the hydrogen atoms of the said alkyl group are substituted with halogen, exemplified by trifluoromethyl, pentafluoroethyl and the like.

The term "hydroxyalkyl" means alkyl, as the case may be, substituted with one or more hydroxyl group(s), where alkyl groups are as defined above. The term "hydroxy" as used herein means "—OH". Examples of "hydroxyalkyl" include but are not limited to —CH₂OH, —CH₂CH₂OH, —CH(OH)CH₂OH and the like.

The term "cycloalkyl" as used herein, means a monocyclic, bicyclic, or tricyclic non-aromatic ring system containing from 3 to 14 carbon atoms, preferably monocyclic cycloalkyl ring containing 3 to 6 carbon atoms. Examples of monocyclic ring systems include cyclopropyl, cyclobutyl, cyclopentyl, cyclohexyl, cycloheptyl, and cyclooctyl. Bicyclic ring systems include monocyclic ring system fused across a bond with another cyclic system which may be an alicyclic ring or an aromatic ring. Bicyclic rings also include spirocyclic systems wherein the second ring gets annulated on a single carbon atom. Bicyclic ring systems are also exemplified by a bridged monocyclic ring system in which two non-adjacent carbon atoms of the monocyclic ring are linked by an alkylene bridge. Examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, bicyclo[3.3.2]decane, bicyclo[3.1.0]hexane, bicyclo[410]heptane, bicyclo[3.2.0]heptanes, octahydro-1H-indene, spiro[2.5]octane, spiro[4.5]decane, spiro[bicyclo[4.1.0]heptane-2,1'-cyclopentane], hexahydro-2'H-spiro[cyclopropane-1,1'-pentalene]. Tricyclic ring systems are the systems wherein the bicyclic systems as described about are further annulated with third ring, which may be alicyclic ring or aromatic ring. Tricyclic ring systems are also exemplified by a bicyclic ring system in which two non-adjacent carbon atoms of the bicyclic ring are linked by a bond or an alkylene bridge. Examples of tricyclic-ring systems include, but are not limited to, tricyclo[3.3.1.0.³·⁷]nonane and tricyclo[3.3.1.1³·⁷]decane (adamantane).

The term "cycloalkenyl" as used herein, means a cycloalkyl group as defined above containing at least one double bond.

When the cycloalkyl or cycloalkenyl groups are substituted cycloalkyl or substituted cycloalkenyl groups, the cycloalkyl and cycloalkenyl groups are substituted with 1 to 3 substituents selected independently from the group consisting of oxo, halogen, nitro, cyano, hydroxyl, hydroxyalkyl, alkyl, alkenyl, perhaloalkyl, aryl, heteroaryl, heterocyclyl, —OR¹⁰ᵇ, —SO₂R¹⁰ᵃ, —C(=O)R¹⁰ᵃ, —C(=O)OR¹⁰ᵃ, —OC(=O)R¹⁰ᵃ, —C(=O)N(H)R¹⁰, —C(=O)N(alkyl)R¹⁰, —N(H)C(=O)R¹⁰ᵃ, —N(H)R¹⁰, —N(alkyl)R¹⁰, —N(H)C(=O)N(H)R¹⁰, —N(H)C(=O)N(alkyl)R¹⁰, —NH—SO₂-alkyl and —NH—SO₂-cycloalkyl; wherein, R¹⁰ is selected from the group consisting of hydrogen, alkyl, alkenyl, cycloalkyl, cycloalkenyl, aryl, heteroaryl, and heterocyclyl; R¹⁰ᵃ is selected from the group consisting of alkyl, alkenyl, perhaloalkyl, cycloalkyl, cycloalkenyl, aryl, heteroaryl, heterocyclyl; $R^{10b}$ is selected from the group consisting of hydrogen, alkyl, alkenyl, perhaloalkyl, cycloalkyl, cycloalkenyl, aryl, heteroaryl, and heterocyclyl.

The term "aryl" refers to a monocyclic, bicyclic or tricyclic aromatic hydrocarbon ring system. Examples of aryl groups include phenyl, naphthyl, anthracenyl, fluorenyl, indenyl, azulenyl, and the like. Aryl group also includes partially saturated bicyclic and tricyclic aromatic hydrocarbons such as tetrahydro-naphthalene.

When the aryl group is a substituted aryl group, the aryl group is substituted with 1 to 3 substituents selected independently from the group consisting of halogen, nitro, cyano, hydroxy, alkyl, alkenyl, perhaloalkyl, cycloalkyl, cycloalkenyl, heterocycle, —O-alkyl, —O— perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl and —NH—SO$_2$-cycloalkyl;

The term "heteroaryl" refers to a 5-14 membered monocyclic, bicyclic, or tricyclic ring system having 1-4 ring heteroatoms selected from O, N, or S, and the remainder ring atoms being carbon (with appropriate hydrogen atoms unless otherwise indicated), wherein at least one ring in the ring system is aromatic. Heteroaryl groups may be optionally substituted with one or more substituents. In one embodiment, 0, 1, 2, 3, or 4 atoms of each ring of a heteroaryl group may be substituted by a substituent. Examples of heteroaryl groups include, but not limited to pyridyl, 1-oxo-pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, benzoxazolyl, benzofuranyl, indolizinyl, imidazopyridyl, tetrazolyl, benzimidazolyl, benzothiazolyl, benzothiadiazolyl, benzoxadiazolyl, indolyl, azaindolyl, imidazopyridyl, quinazolinyl, purinyl, pyrrolo[2,3]pyrimidinyl, pyrazolo[3,4]pyrimidinyl, and benzo(b)thienyl, 2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 2,3-dihydro-benzo[1,4]dioxin-6-yl, 2,3-dihydro-benzo[1,4]dioxin-5-yl, 2,3-dihydro-benzofuran-5-yl, 2,3-dihydro-benzofuran-4-yl, 2,3-dihydro-benzofuran-6-yl, 2,3-dihydro-benzofuran-6-yl, 2,3-dihydro-1H-indol-5-yl, 2,3-dihydro-1H-indol-4-yl, 2,3-dihydro-1H-indol-6-yl, 2,3-dihydro-1H-indol-7-yl, benzo[1,3]dioxol-4-yl, benzo[1,3]dioxol-5-yl, 1,2,3,4-tetrahydroquinolinyl, 1,2,3,4-tetrahydroisoquinolinyl, 2,3-dihydrobenzothien-4-yl, 2-oxoindolin-5-yl and the like.

When the heteroaryl group is a substituted heteroaryl group, the heteroaryl group is substituted with 1 to 3 substituents selected from the group consisting of halogen, nitro, cyano, hydroxy, alkyl, alkenyl, perhaloalkyl, cycloalkyl, cycloalkenyl, heterocycle, —O-alkyl, O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl and —NH—SO$_2$-cycloalkyl.

The term "heterocycle" or "heterocyclic" as used herein, means a 'cycloalkyl' group wherein one or more of the carbon atoms replaced by —O—, —S—, —S(O$_2$)—, —S(O)—, —N(R$^m$)—, —Si(R$^m$)R$^n$—, wherein, R$^m$ and R$^n$ are independently selected from the group consisting of hydrogen, alkyl, aryl, heteroaryl, cycloalkyl, and heterocyclyl. The heterocycle may be connected to the parent molecular moiety through any carbon atom or any nitrogen atom contained within the heterocycle. Examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1.1-dioxidothiomorpholinyl (thiomorpholine sulfone), thiopyranyl, and trithianyl. Examples of bicyclic heterocycle include, but are not limited to 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl and 1,2,3,4-tetrahydroquinolinyl. The term heterocycle also include bridged heterocyclic systems such as azabicyclo[3.2.1]octane, azabicyclo[3.3.1]nonane and the like.

When the heterocyclic group is substituted, it may be substituted either on a ring carbon atom or on a ring hetero atom. When it substituted on a ring carbon atom, it is substituted with 1-3 substituents independently selected from the group consisting of halogen, nitro, cyano, oxo, alkyl, alkenyl, perhaloalkyl, cycloalkyl, cycloalkenyl, aryl, heteroaryl, heterocyclyl, —OR$^{10b}$, —C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, and —N(H)C(=O)N(alkyl)R$^{10}$. When the 'heterocyclic' group is substituted on a ring nitrogen, it is substituted with a substituent selected from the group consisting of alkyl, alkenyl, cycloalkyl, cycloalkenyl, aryl, heteroaryl, —SO$_2$R$^{10a}$, —C(=O)R$^{10a}$, —C(=O)OR$^{10a}$, —C(=O)N(H)R$^{10}$, —C(=O)N(alkyl)R$^{10}$, —NH—SO$_2$-alkyl and —NH—SO$_2$-cycloalkyl. When the heterocyclic group is substituted on a ring sulphur of 'heterocycle', it is substituted with 1 or 2 oxo group.

The term 'oxo' means a divalent oxygen (=O) attached to the parent group. For example oxo attached to carbon forms a carbonyl, oxo substituted on cyclohexane forms a cyclohexanone, and the like.

The term 'annulated' means the ring system under consideration is either annulated with another ring at a carbon atom of the cyclic system or across a bond of the cyclic system as in the case of fused or spiro ring systems.

The term 'bridged' means the ring system under consideration contain an alkylene bridge having 1 to 4 methylene units joining two non adjacent ring atoms.

It should be understood that the formulas (I), (Ia), (Ib) and (Ic) structurally encompasses all stereoisomers, tautomers and pharmaceutically acceptable salts that may be contemplated from the chemical structure of the genera described herein.

A compound, its stereoisomers, racemates, tautomers and pharmaceutically acceptable salt thereof as described hereinabove wherein the compound of general formula I, (Ia), (Ib) and (Ic) can be selected from the group consisting of:

3-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide (Compound 1)

N-cyclopropyl-3-(5-((2-fluoro-4-iodophenyl)amino)-6,8-dimethyl-2,4,7-trioxo-3,4,6,7-tetrahydropyrido[4,3-d]pyrimidin-1(2H)-yl)benzamide (Compound 2)

1-(3-(azetidine-1-carbonyl)phenyl)-5-((2-fluoro-4-iodophenyl)amino)-6,8-dimethylpyrido[4,3-d]pyrimidine-2,4,7(1H,3H,6H)-trione (Compound 3)

N-cyclopropyl-2-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide (Compound 4)

2-(3-(5-((2-fluoro-4-iodophenyl)amino)-6,8-dimethyl-2,4,7-trioxo-3,4,6,7-tetrahydro pyrido[4,3-d]pyrimidin-1(2H)-yl)phenoxy)-N-methylacetamide (Compound 5)

N-cyclopropyl-2-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenoxy)acetamide (Compound 6)

5-((2-fluoro-4-iodophenyl)amino)-6,8-dimethyl-1-(3-(morpholine-4-carbonyl)phenyl)pyrido[4,3-d]pyrimidine-2,4,7(1H,3H,6H)-trione (Compound 7)

1-(3-(1,1-dioxidothiomorpholine-4-carbonyl)phenyl)-5-((2-fluoro-4-iodophenyl)amino)-6,8-dimethylpyrido[4,3-d]pyrimidine-2,4,7(1H,3H,6H)-trione (Compound 8)

2-(3-(5-((2-fluoro-4-iodophenyl)amino)-6,8-dimethyl-2,4,7-trioxo-3,4,6,7-tetrahydro pyrido[4,3-d]pyrimidin-1(2H)-yl)phenyl)-2-methylpropanamide (Compound 9)

2-(3-(5-((2-fluoro-4-iodophenyl)amino)-6,8-dimethyl-2,4,7-trioxo-3,4,6,7-tetrahydro pyrido[4,3-d]pyrimidin-1(2H)-yl)phenyl)-N,N-dimethylacetamide (Compound 10)

2,2-difluoro-2-(3-(5-((2-fluoro-4-iodophenyl)amino)-6,8-dimethyl-2,4,7-trioxo-3,4,7,8-tetrahydropyrido[2,3-d]pyrimidin-1(2H)-yl)phenyl)acetamide (Compound 11)

N-(1-carbamoylcyclopropyl)-3-(5-((2-fluoro-4-iodophenyl)amino)-6,8-dimethyl-2,4,7-trioxo-3,4,6,7-tetrahydropyrido[4,3-d]pyrimidin-1(2H)-yl)benzamide (Compound 12)

3-(5-((2-fluoro-4-iodophenyl)amino)-6,8-dimethyl-2,4,7-trioxo-3,4,6,7-tetrahydropyrido[4,3-d]pyrimidin-1(2H)-yl)-N-(tetrahydro-2H-pyran-4-yl)benzamide (Compound 13)

2-(3-(5-((2-fluoro-4-iodophenyl)amino)-6,8-dimethyl-2,4,7-trioxo-3,4,6,7-tetrahydro pyrido[4,3-d]pyrimidin-1(2H)-yl)phenyl)-2-hydroxyacetamide (Compound 14)

3-(3-(5-((2-fluoro-4-iodophenyl)amino)-6,8-dimethyl-2,4,7-trioxo-3,4,6,7-tetrahydro pyrido[4,3-d]pyrimidin-1(2H)-yl)phenyl)-N-methylpropanamide (Compound 15)

2-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenoxy)acetamide (Compound 16)

1-(3-(1,1-dioxidothiazolidine-3-carbonyl)phenyl)-5-((2-fluoro-4-iodophenyl)amino)-6,8-dimethylpyrido[4,3-d]pyrimidine-2,4,7(1H,3H,6H)-trione (Compound 17)

5-((2-fluoro-4-iodophenyl)amino)-1-(3-(4-hydroxypiperidine-1-carbonyl)phenyl)-6,8-dimethylpyrido[4,3-d]pyrimidine-2,4,7(1H,3H,6H)-trione (Compound 18)

N-cyclopropyl-3-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide (Compound 19)

2-(3-(5-((2-fluoro-4-iodophenyl)amino)-6,8-dimethyl-2,4,7-trioxo-3,4,6,7-tetrahydro pyrido[4,3-d]pyrimidin-1(2H)-yl)phenoxy)-2-methylpropanamide (Compound 20)

5-((2-fluoro-4-iodophenyl)amino)-6,8-dimethyl-1-(3-(4-methylpiperazine-1-carbonyl)phenyl)pyrido[4,3-d]pyrimidine-2,4,7(1H,3H,6H)-trione (Compound 21)

5-((2-fluoro-4-iodophenyl)amino)-1-(3-(3-hydroxypyrrolidine-1-carbonyl)phenyl)-6,8-dimethylpyrido[4,3-d]pyrimidine-2,4,7(1H,3H,6H)-trione (Compound 22)

5-((2-fluoro-4-iodophenyl)amino)-6,8-dimethyl-1-(3-(piperazine-1-carbonyl)phenyl)pyrido[4,3-d]pyrimidine-2,4,7(1H,3H,6H)-trione (Compound 23)

1-(3-(azetidine-1-carbonyl)phenyl)-3-cyclopropyl-5-((2-fluoro-4-iodophenyl)amino)-6,8-dimethylpyrido[4,3-d]pyrimidine-2,4,7(1H,3H,6H)-trione (Compound 24)

N-cyclopropyl-2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenoxy)acetamide (Compound 25)

2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide (Compound 26)

3-cyclopropyl-5-((2-fluoro-4-iodophenyl)amino)-6,8-dimethyl-1-(3-(pyrrolidine-1-carbonyl)phenyl)pyrido[4,3-d]pyrimidine-2,4,7(1H,3H,6H)-trione (Compound 27)

2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-2-methylpropanamide (Compound 28)

2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N,N-dimethylacetamide (Compound 29)

2-(3-(3-cyclopropyl-5-((2-fluoro-4-iodophenyl)amino)-6,8-dimethyl-2,4,7-trioxo-3,4,7,8-tetrahydropyrido[2,3-d]pyrimidin-1(2H)-yl)phenyl)-2,2-difluoroacetamide (Compound 30)

2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N-(oxetan-3-yl)acetamide (Compound 31)

2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-2-hydroxyacetamide (Compound 32)

3-cyclopropyl-5-((2-fluoro-4-iodophenyl)amino)-1-(3-(2-(3-hydroxyazetidin-1-yl)-2-oxo ethyl)phenyl)-6,8-dimethylpyrido[4,3-d]pyrimidine-2,4,7(1H,3H,6H)-trione (Compound 33)

3-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide (Compound 34)

2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenoxy)acetamide (Compound 35)

3-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N-methylpropanamide (Compound 36)

N-cyclopropyl-3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)benzamide (Compound 37)

3-cyclopropyl-1-(3-(1,1-dioxidothiazolidine-3-carbonyl)phenyl)-5-((2-fluoro-4-iodophenyl)amino)-6,8-dimethylpyrido[4,3-d]pyrimidine-2,4,7(1H,3H,6H)-trione (Compound 38)

3-cyclopropyl-1-(3-(1,1-dioxidothiomorpholine-4-carbonyl)phenyl)-5-((2-fluoro-4-iodophenyl)amino)-6,8-dimethylpyrido[4,3-d]pyrimidine-2,4,7(1H,3H,6H)-trione (Compound 39)

N-cyclopropyl-3-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide (Compound 40)

N-cyclopropyl-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenoxy)acetamide (Compound 41)

2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)acetamide (Compound 42)

2-(3-(5-((2-fluoro-4-iodophenyl)amino)-3,6,8-trimethyl-2,4,7-trioxo-3,4,6,7-tetra hydropyrido[4,3-d]pyrimidin-1(2H)-yl)phenyl)-2-methylpropanamide (Compound 43)

2-(3-(5-((2-fluoro-4-iodophenyl)amino)-3,6,8-trimethyl-2,4,7-trioxo-3,4,6,7-tetra hydropyrido[4,3-d]pyrimidin-1(2H)-yl)phenyl)-N,N-dimethylacetamide (Compound 44)

2,2-difluoro-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)acetamide (Compound 45)

1-(3-(2-(azetidin-1-yl)-2-oxoethyl)phenyl)-5-((2-fluoro-4-iodophenyl)amino)-3,6,8-trimethylpyrido[4,3-d]pyrimidine-2,4,7(1H,3H,6H)-trione (Compound 46)

2-(3-(5-((2-fluoro-4-iodophenyl)amino)-3,6,8-trimethyl-2,4,7-trioxo-3,4,6,7-tetrahydro pyrido[4,3-d]pyrimidin-1(2H)-yl)phenyl)-2-hydroxyacetamide (Compound 47)

5-((2-fluoro-4-iodophenyl)amino)-1-(3-(2-(3-hydroxyazetidin-1-yl)-2-oxoethyl)phenyl)-3,6,8-trimethylpyrido[4,3-d]pyrimidine-2,4,7(1H,3H,6H)-trione (Compound 48)

3-(5-((2-fluoro-4-iodophenyl)amino)-3,6,8-trimethyl-2,4,7-trioxo-3,4,6,7-tetra hydropyrido[4,3-d]pyrimidin-1(2H)-yl)-N-(oxetan-3-yl)benzamide (Compound 49)

2-(3-(5-((2-fluoro-4-iodophenyl)amino)-3,6,8-trimethyl-2,4,7-trioxo-3,4,6,7-tetrahydro pyrido[4,3-d]pyrimidin-1(2H)-yl)phenyl)-N-(oxetan-3-yl)acetamide (Compound 50)

3-(5-((2-fluoro-4-iodophenyl)amino)-3,6,8-trimethyl-2,4,7-trioxo-3,4,6,7-tetrahydro pyrido[4,3-d]pyrimidin-1(2H)-yl)-N-(tetrahydrofuran-3-yl)benzamide (Compound 51)

3-(5-((2-fluoro-4-iodophenyl)amino)-3,6,8-trimethyl-2,4,7-trioxo-3,4,6,7-tetrahydro pyrido[4,3-d]pyrimidin-1(2H)-yl)-N-(tetrahydro-2H-pyran-4-yl)benzamide (Compound 52)

3-(5-((2-fluoro-4-iodophenyl)amino)-3,6,8-trimethyl-2,4,7-trioxo-3,4,6,7-tetrahydro pyrido[4,3-d]pyrimidin-1(2H)-yl)-N-(1-(hydroxymethyl)cyclopropyl)benzamide (Compound 53)

N-cyclopropyl-3-(5-((2-fluoro-4-iodophenyl)amino)-3,6,8-trimethyl-2,4,7-trioxo-3,4,6,7-tetrahydropyrido[4,3-d]pyrimidin-1(2H)-yl)benzamide (Compound 54)

N-cyclopropyl-3-(5-((2-fluoro-4-iodophenyl)amino)-3-(2-hydroxyethyl)-6,8-dimethyl-2,4,7-trioxo-3,4,6,7-tetrahydropyrido[4,3-d]pyrimidin-1(2H)-yl)benzamide (Compound 55)

1-(3-(azetidine-1-carbonyl)phenyl)-5-((2-fluoro-4-iodophenyl)amino)-3,6,8-trimethylpyrido[4,3-d]pyrimidine-2,4,7(1H,3H,6H)-trione (Compound 56)

2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenoxy)acetamide (Compound 57)

N-cyclopropyl-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)acetamide (Compound 58)

N-cyclopropyl-2-(3-(3-ethyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide (Compound 59)

2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenoxy)-N-methylacetamide (Compound 60)

3-(3-(3-ethyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide (Compound 61)

N-cyclopropyl-3-(3-ethyl-5-((2-fluoro-4-iodophenyl)amino)-6,8-dimethyl-2,4,7-trioxo-3,4,6,7-tetrahydropyrido[4,3-d]pyrimidin-1(2H)-yl)benzamide (Compound 62)

5-((2-fluoro-4-iodophenyl)amino)-3,6,8-trimethyl-1-(3-(morpholine-4-carbonyl)phenyl)pyrido[4,3-d]pyrimidine-2,4,7(1H,3H,6H)-trione (Compound 63)

ethyl 2-(1-(3-(cyclopropylcarbamoyl)phenyl)-5-((2-fluoro-4-iodophenyl)amino)-6,8-dimethyl-2,4,7-trioxo-1,2,6,7-tetrahydropyrido[4,3-d]pyrimidin-3 (4H)-yl)acetate (Compound 64)

1-(3-(1,1-dioxidothiomorpholine-4-carbonyl)phenyl)-5-((2-fluoro-4-iodophenyl)amino)-3,6,8-trimethylpyrido[4,3-d]pyrimidine-2,4,7(1H,3H,6H)-trione (Compound 65)

1-(3-(1,1-dioxidothiomorpholine-4-carbonyl)phenyl)-3-ethyl-5-((2-fluoro-4-iodophenyl)amino)-6,8-dimethylpyrido[4,3-d]pyrimidine-2,4,7(1H,3H,6H)-trione (Compound 66)

2-(3-(3-ethyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N,N-dimethylacetamide (Compound 67)

3-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)propanamide (Compound 68)

N-cyclopropyl-3-(5-((2-fluoro-4-iodophenyl)amino)-3-isopropyl-6,8-dimethyl-2,4,7-trioxo-3,4,6,7-tetrahydropyrido[4,3-d]pyrimidin-1(2H)-yl)benzamide (Compound 69)

3-(3-allyl-5-((2-fluoro-4-iodophenyl)amino)-6,8-dimethyl-2,4,7-trioxo-3,4,6,7-tetrahydropyrido[4,3-d]pyrimidin-1(2H)-yl)-N-cyclopropylbenzamide (Compound 70)

2-(3-(5-((2-fluoro-4-iodophenyl)amino)-6,8-dimethyl-3-(oxetan-3-yl)-2,4,7-trioxo-3,4,6,7-tetrahydropyrido[4,3-d]pyrimidin-1(2H)-yl)phenoxy)acetamide (Compound 71)

N-cyclopropyl-3-(3-(difluoromethyl)-5-((2-fluoro-4-iodophenyl)amino)-6,8-dimethyl-2,4,7-trioxo-3,4,6,7-tetrahydropyrido[4,3-d]pyrimidin-1(2H)-yl)benzamide (Compound 72)

N-cyclopropyl-3-(3-(2,3-dihydroxypropyl)-5-((2-fluoro-4-iodophenyl)amino)-6,8-dimethyl-2,4,7-trioxo-3,4,6,7-tetrahydropyrido[4,3-d]pyrimidin-1(2H)-yl)benzamide (Compound 73)

2-(1-(3-(cyclopropylcarbamoyl)phenyl)-5-((2-fluoro-4-iodophenyl)amino)-6,8-dimethyl-2,4,7-trioxo-1,2,6,7-tetrahydropyrido[4,3-d]pyrimidin-3(4H)-yl)acetic acid (Compound 74)

(R)-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)-2-hydroxyacetamide (Compound 75)

(S)-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)-2-hydroxyacetamide (Compound 76)

1-(3-(5-((2-fluoro-4-iodophenyl)amino)-6,8-dimethyl-1-2,4,7-trioxo-3,4,6,7-tetra hydropyrido[4,3-d]pyrimidin-1(2H)-yl)phenyl)cyclopropanecarboxamide (Compound 77)

1-(3-(3-cyclopropyl-5-((2-fluoro-4-iodophenyl)amino)-6,8-dimethyl-2,4,7-trioxo-3,4,6,7-tetra hydropyrido[4,3-d]pyrimidin-1(2H)-yl)phenyl)cyclopropanecarboxamide (Compound 78) and 1-(3-(5-((2-fluoro-4-iodophenyl)amino)-3,6,8-trimethyl-2,4,7-trioxo-3,4,6,7-tetrahydro pyrido[4,3-d]pyrimidin-1(2H)-yl)phenyl)cyclopropanecarboxamide (Compound 79)

The present disclosure provides a method for inhibiting MEK enzymes comprising contacting said MEK enzyme with a composition comprising a compound of I, Ia, Ib, Ic, their tautomeric forms, their stereoisomers or their pharmaceutically acceptable salts, sufficient to inhibit said enzyme, wherein said enzyme inhibited MEK kinase, which occurs within cell.

The invention also provides a method of treatment of a MEK mediated disorder in an individual suffering from said disorder, comprising administering to said individual an effective amount of a composition comprising a compound of formula I, Ia, Ib, Ic, their tautomeric forms, their stereoisomers or their pharmaceutically acceptable salts. The method of treatment may also be combined with an additional therapy such as radiation therapy, chemotherapy, or combination thereof.

MEK mediated disorders, as stated above, include inflammatory diseases, infections, autoimmune disorders, stroke, ischemia, cardiac disorder, neurological disorders, fibrogenetic disorders, proliferative disorders, hyperproliferative disorders, tumors, leukemias, neoplasms, cancers, carcinomas, metabolic diseases and malignant diseases.

The invention further provides a method for the treatment or prophylaxis of a proliferative disease in an individual comprising administering to said individual an effective amount of a composition comprising a compound of formula I, Ia, Ib, Ic, their tautomeric forms, their stereoisomers or their pharmaceutically acceptable salts. The proliferative disease includes cancer, psoriasis, restenosis, autoimmune disease, or atherosclerosis.

The invention also provides a method for the treatment or prophylaxis of an inflammatory disease in an individual comprising administering to said individual an effective amount of a composition comprising a compound of formula I, Ia, Ib, Ic, their tautomeric forms, their stereoisomers or their pharmaceutically acceptable salts. The inflammatory disease includes rheumatoid arthritis or multiple sclerosis.

The invention also provide a method for degrading, inhibiting the growth of or killing cancer cells comprising contacting the cells with an amount of a composition effective to degrade, inhibit the growth of or kill cancer cells, the composition comprising a compound of formula I, Ia, Ib, Ic, their tautomeric forms, their stereoisomers or their pharmaceutically acceptable salts.

The invention also provide a method of inhibiting tumor size increase, reducing the size of a tumor, reducing tumor proliferation or preventing tumor proliferation in an individual in need thereof comprising administering to said individual an effective amount of a composition to inhibit tumor size increase, reduce the size of a tumor, reduce tumor proliferation or prevent tumor proliferation, the composition comprising a compound of formula I, Ia, Ib, Ic, their tautomeric forms, their stereoisomers or their pharmaceutically acceptable salts.

The MEK-ERK pathway is activated in numerous inflammatory conditions (Kyriakis and Avruch 1996, Vol. 271, No. 40, pp. 24313-24316; Hammaker et al., J Immunol 2004; 172; 1612-1618), including rheumatoid arthritis, inflammatory bowel disease and COPD.

The present invention describes the inhibitors of MEK kinase for treatment of disorders that are driven by hyperactivation, abnormal activation, constitutive activation, gain-of-function mutation of the MEK kinase and/or its substrate kinases that include but are not limited to ERK. Such disorders encompass hyperproliferative disorders that include but are not limited to psoriasis, keloids, hyperplasia of the skin, benign prostatic hyperplasia (BPH), solid tumors such as cancers of the respiratory tract (including but not limited to small cell and non-small cell lung carcinomas), brain (including but not limited to glioma, medulloblastoma, ependymoma, neuroectodermal and pineal tumors), breast (including but not limited to invasive ductal carcinoma, invasive lobular carcinoma, ductal- and lobular carcinoma in situ), reproductive organs (including but not limited to prostate cancer, testicular cancer, ovarian cancer, endometrial cancer, cervical cancer, vaginal cancer, vulvar cancer, and sarcoma of the uterus), digestive tract (including but not limited to esophageal, colon, colorectal, gastric, gall blabber, pancreatic, rectal, anal, small intestine and salivary gland cancers), urinary tract (including but not limited to bladder, ureter, kidney, renal, urethral and papillary renal cancers), eye (including but not limited to intraocular melanoma, and retinoblastoma), liver (including but not limited to hepatocellular carcinoma, and cholangiocarcinoma), skin (including but not limited to melanoma, squamous cell carcinoma, Kaposi's sarcoma, Merkel cell skin cancer, non-melanoma skin cancer), head and neck (including but not limited to laryngeal, nasopharyngeal, hypopharyngeal, oropharyngeal cancer, lip and oral cavity cancer and squamous cell cancer), thyroid, parathyroid, and their metastases. The hyperrproliferative disorders also include, leukemias (including but not limited to acute lymphoblastic leukemia, acute myeloid leukemia, chronic melogenous leukemia, chronic lymphocytic leukemia, and hairy cell leukemia), sarcomas (including but not limited to soft tissue sarcoma, osteosarcoma, lymphosarcoma, rhabdomyosarcoma), and lymphomas (including but not limited to non-Hodgkin's lymphoma, AIDS-related lymphoma, cutaneous T cell lymphoma, Burkitt's lymphoma, Hodgkin's disease, and lymphoma of the central nervous system).

The present invention describes the inhibitors of MEK kinase for treatment of certain disorders involving aberrant regulation of the mitogen extracellular kinase activity including but not limited to hepatomegaly, heart failure, cardiomegaly, diabetes, stroke, Alzheimer's disease, cystic fibrosis, septic shock or asthma.

The present invention describes the inhibitors of MEK kinase for treatment of diseases and disorders associated with aberrant, abnormal and/or excessive angiogenesis. Such disorders associated with angiogenesis include but are not limited to, tumor growth and metastases, ischemic retinal vein occlusion, diabetic retinopathy, macular degeneration, neovascular glaucoma, psoriasis, inflammation, rheumatoid arthritis, vascular graft restenosis, restenosis and in-stent restenosis.

The compounds mentioned in this invention can be used as a single (sole) therapeutic agent or in combination with other active agents, including chemotherapeutic agents and anti-inflammatory agents. Such combinations include but are not limited to combining the MEK kinase inhibitors with anti-mitotic agents, anti-antiangiogenic agents, alkylating agents, anti-hyperproliferative agents, antimetabolites, DNA-intercalating agents, cell cycle inhibitors, kinase inhibitors, growth factor inhibitors, enzyme inhibitors, topoisomerase inhibitors, biological response modifiers or anti-hormones.

The term 'room temperature' denotes any temperature ranging between about 20° C. to about 40° C., except and otherwise it is specifically mentioned in the specification.

The intermediates and the compounds of the present invention may be obtained in pure form in a manner known per se, for example, by distilling off the solvent in vacuum and re-crystallizing the residue obtained from a suitable solvent, such as pentane, diethyl ether, isopropyl ether, chloroform, dichloromethane, ethyl acetate, acetone or their combinations or subjecting it to one of the purification methods, such as column chromatography (e.g., flash chromatography) on a suitable support material such as alumina or silica gel using eluent such as dichloromethane, ethyl acetate, hexane, methanol, acetone and their combinations. Preparative LC-MS method is also used for the purification of molecules described herein.

Salts of compound of formula I can be obtained by dissolving the compound in a suitable solvent, for example in a chlorinated hydrocarbon, such as methyl chloride or chloroform or a low molecular weight aliphatic alcohol, for example, ethanol or isopropanol, which was then treated with the desired acid or base as described in Berge S. M. et al. "Pharmaceutical Salts, a review article in Journal of Pharmaceutical sciences volume 66, page 1-19 (1977)" and in handbook of pharmaceutical salts properties, selection, and use by P. H. Einrich Stahland Camille G. wermuth, Wiley—VCH (2002). Lists of suitable salts can also be found in *Remington's Pharmaceutical Sciences,* 18th ed., Mack Publishing Company, Easton, Pa., 1990, p. 1445, and *Journal of Pharmaceutical Science,* 66, 2-19 (1977). For example, the salt can be of an alkali metal (e.g., sodium or potassium), alkaline earth metal (e.g., calcium), or ammonium.

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, potassium hydroxide. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The stereoisomers of the compounds of formula I of the present invention may be prepared by stereospecific syntheses or resolution of racemic compound using an optically active amine, acid or complex forming agent, and separating the diastereomeric salt/complex by fractional crystallization or by column chromatography.

The compounds of formula I of the present invention can exist in tautomeric forms, such as keto-enol tautomers. Such tautomeric forms are contemplated as an objective of this invention and such tautomers may be in equilibrium or predominant in one of the forms.

The prodrugs can be prepared in situ during the isolation and purification of the compounds, or by separately reacting the purified compound with a suitable derivatizing agent. For example, hydroxy groups can be converted into esters via treatment with a carboxylic acid in the presence of a catalyst. Examples of cleavable alcohol prodrug moieties include substituted or unsubstituted, branched or unbranched lower alkyl ester moieties, e.g., ethyl esters, lower alkenyl esters, di-lower alkylamino lower-alkyl esters, e.g., dimethylaminoethyl ester, acylamino lower alkyl esters, acyloxy lower alkyl esters (e.g., pivaloyloxymethyl ester), aryl esters, e.g., phenyl ester, aryl-lower alkyl esters, e.g., benzyl ester, substituted- or unsubstituted, e.g., with methyl, halo, or methoxy substituents aryl and aryl-lower alkyl esters, amides, lower-alkyl amides, di-lower alkyl amides, and hydroxy amides.

The term "prodrug" denotes a derivative of a compound, which derivative, when administered to warm-blooded animals, e.g. humans, is converted into the compound (drug). The enzymatic and/or chemical hydrolytic cleavage of the compounds of the present invention occurs in such a manner that the proven drug form (parent carboxylic acid drug) is released, and the moiety or moieties split off remain non-toxic or are metabolized so that nontoxic metabolic products are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

The inhibitors mentioned in the present invention can be combined with anti-inflammatory agents or agents that show therapeutic benefit for conditions including but not limited to hepatomegaly, heart failure, cardiomegaly, diabetes, stroke, Alzheimer's disease, cystic fibrosis, septic shock or asthma, diabetic retinopathy, ischemic retinal vein occlusion, macular degeneration, neovascular glaucoma, psoriasis, inflammation, rheumatoid arthritis, restenosis, in-stent restenosis, and vascular graft restenosis.

The term "aberrant kinase activity" refers to any abnormal expression or activity of the gene encoding the kinase or of the polypeptide it encodes. Examples of such aberrant kinase activity include but are not limited to over-expression of the gene or polypeptide, gene amplification, mutations that produce constitutively active or hyperactive kinase activity, gene mutations, deletions, substitutions, additions, and the like.

Thus the present invention further provides a pharmaceutical composition, containing the compounds of the general formula (I) as defined above, its tautomeric forms, its stereoisomers, its pharmaceutically acceptable salts in combination with the usual pharmaceutically acceptable carriers, diluents, excipients, and the like.

The pharmaceutically acceptable carrier or excipient is preferably one that is chemically inert to the compound of the invention and one that has no detrimental side effects or toxicity under the conditions of use. Such pharmaceutically acceptable carriers or excipients include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting.

The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride, with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

A compound of the present invention, alone or in combination with other suitable components, can be made into aerosol formulations to be administered via inhalation. A compound or epimer of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

The concentration of the compound in the pharmaceutical formulations can vary, e.g., from less than about 1% to about 10%, to as much as about 20% to about 50% or more by weight, and can be selected primarily by fluid volumes, and viscosities, in accordance with the particular mode of administration selected.

For example, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* (17$^{th}$ ed., Mack Publishing Company, Easton, Pa., 1985).

It will be appreciated by one of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The compounds of the invention can be administered in a dose sufficient to treat the disease, condition or disorder. Such doses are known in the art (see, for example, the *Physicians' Desk Reference* (2004)). The compounds can be administered using techniques such as those described in, for example, Wasserman et al., *Cancer*, 36, pp. 1258-1268 (1975) and *Physicians' Desk Reference*, 58th ed., Thomson PDR (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 µg to about 50 mg of at least one compound of the invention per kg body weight of the individual. For a 70 kg patient, dosages of from about 10 µg to about 200 mg of the compound of the invention would be more commonly used, depending on a patient's physiological response.

By way of example and not intending to limit the invention, the dose of the pharmaceutically active agent(s) described herein for methods of treating or preventing a disease or condition as described above can be about 0.001 to about 1 mg/kg body weight of the subject per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for the described methods can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the disclosed methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

In accordance with the invention, the term subject includes an "animal" which in turn includes a mammal such as, without limitation, the order Rodentia, such as mice, and the order Lagomorpha, such as rabbits. In one aspect, the mammals are from the order Carnivora, including Felines (cats) and Canines (dogs). In another aspect, the mammals are from the order Artiodactyla, including Bovines (cows) and Swine (pigs) or of the order Perssodactyla, including Equines (horses). In a further aspect, the mammals are of the order Primates, Ceboids, or Simoids (monkeys) or of the order Anthropoids (humans and apes). In yet another aspect, the mammal is human.

General Method of Preparation

The compounds of general formula (I) where all the symbols are as defined earlier can be prepared by methods given in below schemes or examples illustrated herein below.

However, the disclosure should not be construed to limit the scope of the invention arriving at compound of formula (I) disclosed hereinabove.

Scheme 1 (R$^1$ is H)

Compound of formula (I) where R$^1$ is H, can be prepared as depicted in Scheme 1, details of which are given below.

Scheme 1

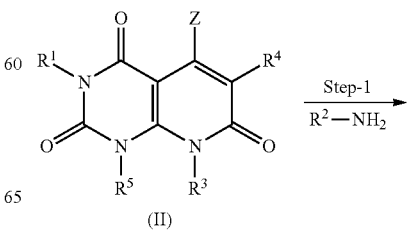

(II)

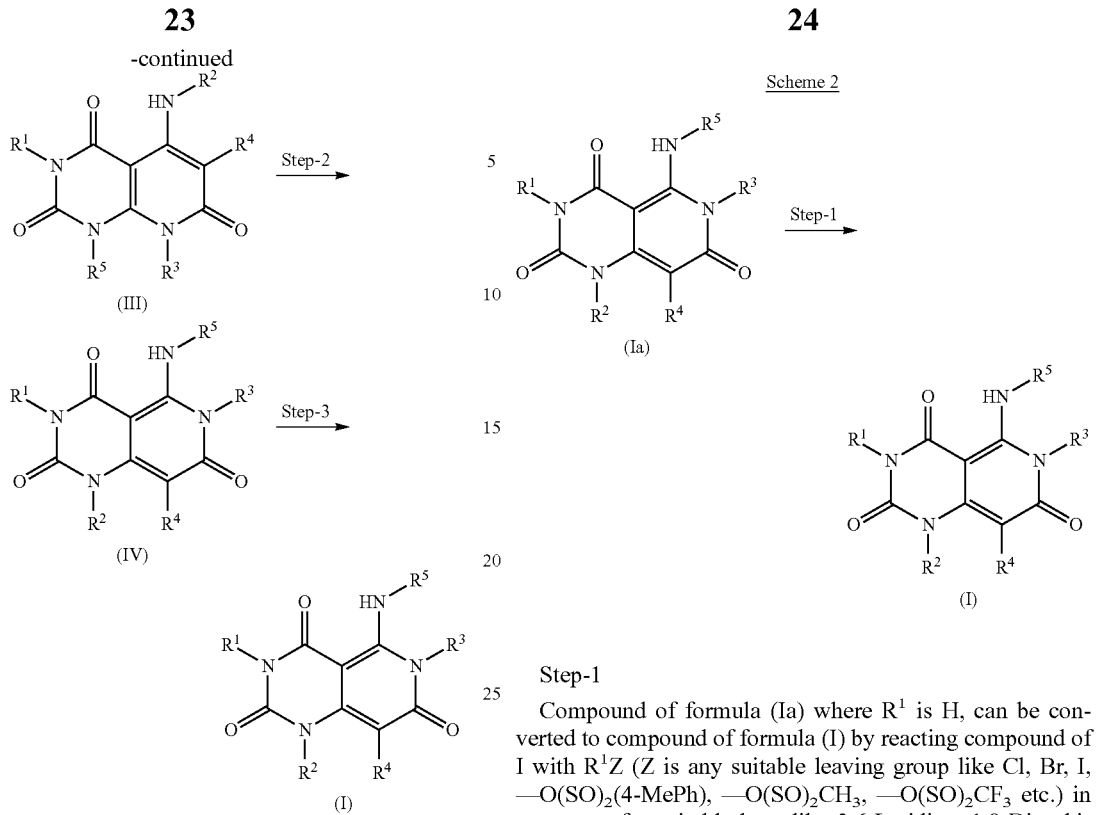

(III)

(IV)

(I)

Step-1

Compound of formula (II) where $R^1$ is N-protecting group, can be converted to compound of formula (III) by reacting compound of (II) (Prepared as per reference WO2005121142) (Z is any suitable leaving group like Cl, Br, I, —O(SO)$_2$(4-MePh), —O(SO)$_2$CH$_3$, —O(SO)$_2$CF$_3$ etc.) with $R^2NH_2$ in presence of a suitable base like 2,6-Lutidine, 1,8-Diazabicyclo[5.4.0]undec-7-ene (DBU), K$_2$CO$_3$, Cs$_2$CO$_3$, NaH, KH, n-BuLi, lithium bis(trimethylsilyl)amide (LiHMDS) etc., in a solvent like THF, DMF, DMSO etc., at temperature ranging from about −78° C. to about 150° C.

Step-2

Compound of formula-(III) where $R^1$ is N-protecting group, can be converted to compound of formula-(IV) by reacting compound of formula (III) with suitable base such as NaOMe, K$_2$CO$_3$ etc. in a solvent like Methanol, Ethanol, THF, DMF etc. at temperature ranging from about −78° C. to about 150° C.

Step-3

Compound of formula-(IV) where $R^1$ is N-protecting group, can be converted to compound of formula-(I) by reacting compound of formula (IV) with suitable N-deprotection agents such as AlCl$_3$, Pd—C/H$_2$ etc. in a solvent like Anisole, Toluene, Xylene, THF, DMF, DMSO etc. at temperature ranging from about −78° C. to about 150° C.

Scheme-2:

Compound of formula (I), where $R^1$ is selected from the group consisting of substituted- or unsubstituted-alkyl, substituted- or unsubstituted-alkenyl, substituted- or unsubstituted-alkynyl, substituted- or unsubstituted-cycloalkyl, substituted- or unsubstituted-cycloalkenyl, substituted- or unsubstituted-aryl, substituted- or unsubstituted-heteroaryl, and substituted- or unsubstituted-heterocyclyl, can be prepared as depicted in Scheme 2, details of which are given below Scheme 2

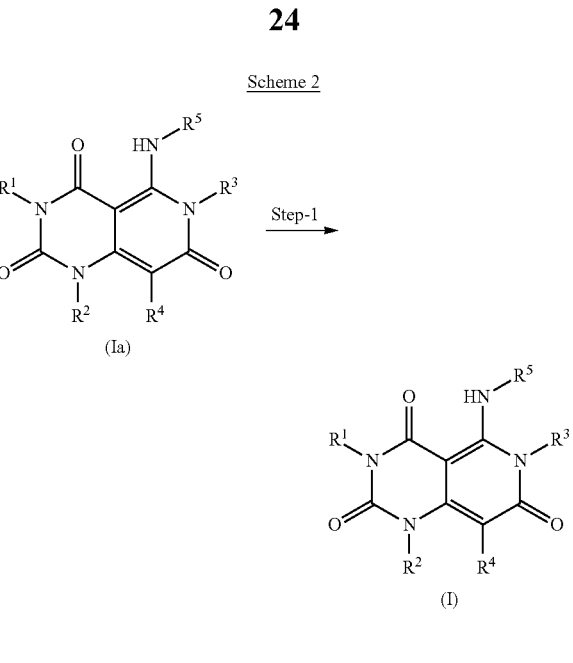

(Ia)

(I)

Step-1

Compound of formula (Ia) where $R^1$ is H, can be converted to compound of formula (I) by reacting compound of I with $R^1Z$ (Z is any suitable leaving group like Cl, Br, I, —O(SO)$_2$(4-MePh), —O(SO)$_2$CH$_3$, —O(SO)$_2$CF$_3$ etc.) in presence of a suitable base like 2,6-Lutidine, 1,8-Diazabicyclo[5.4.0]undec-7-ene (DBU), K$_2$CO$_3$, Cs$_2$CO$_3$, NaH, KH, n-BuLi, lithium bis(trimethylsilyl)amide (LiHMDS) etc., in a solvent like THF, DMF, DMSO etc., at temperature ranging from about −78° C. to about 150° C.

Scheme-3:

Compound of formula (I) where $R^1$ is selected from the group consisting of substituted- or unsubstituted-alkyl, substituted- or unsubstituted-alkenyl, substituted- or unsubstituted-alkynyl, substituted- or unsubstituted-cycloalkyl, substituted- or unsubstituted-cycloalkenyl, substituted- or unsubstituted-aryl, substituted- or unsubstituted-heteroaryl, and substituted- or unsubstituted-heterocyclyl, can be prepared as depicted in Scheme 3, details of which are given below Scheme 3

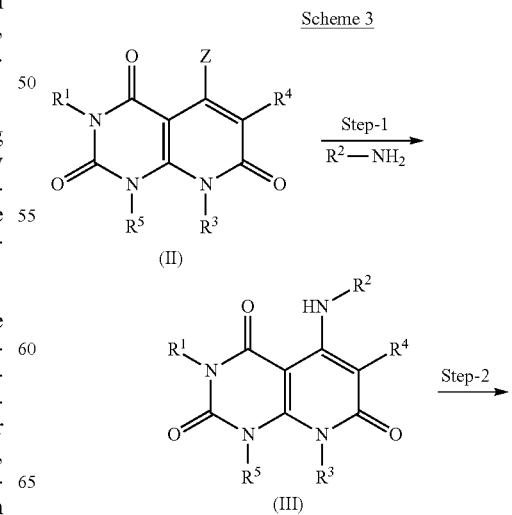

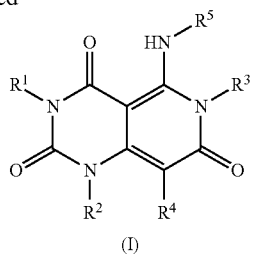

(I)

Step-1

Compound of formula (II) where R¹ is selected from the group consisting of substituted- or unsubstituted-alkyl, substituted- or unsubstituted-alkenyl, substituted- or unsubstituted-alkynyl, substituted- or unsubstituted-cycloalkyl, substituted- or unsubstituted-cycloalkenyl, substituted- or unsubstituted-aryl, substituted- or unsubstituted-heteroaryl, and substituted- or unsubstituted-heterocyclyl, can be converted to compound of formula (III) by reacting compound of II (Z is any suitable leaving group like Cl, Br, I, —O(SO)₂(4-MePh), —O(SO)₂CH₃, —O(SO)₂CF₃ etc.) with R²NH₂ in presence of a suitable base like 2,6-Lutidine, 1,8-Diazabicyclo[5.4.0]undec-7-ene (DBU), K₂CO₃, Cs₂CO₃, NaH, KH, n-BuLi, lithium bis(trimethylsilyl)amide (LiHMDS) etc., in a solvent like THF, DMF, DMSO and the like, at temperature ranging from about −78° C. to about 150° C.

Step-2

Compound of formula-(III) where R¹ is selected from the group consisting of substituted- or unsubstituted-alkyl, substituted- or unsubstituted-alkenyl, substituted- or unsubstituted-alkynyl, substituted- or unsubstituted-cycloalkyl, substituted- or unsubstituted-cycloalkenyl, substituted- or unsubstituted-aryl, substituted- or unsubstituted-heteroaryl, and substituted- or unsubstituted-heterocyclyl, can be converted to compound of formula-(I) by reacting compound of formula (III) with suitable base such as NaOMe, K₂CO₃ etc. in a solvent like Methanol, Ethanol, THF, DMF etc. at temperature ranging from about −78° C. to about 150° C.

The intermediates and the compounds of the present invention are obtained in pure form in a manner known per se, for example by distilling off the solvent in vacuum and re-crystallizing the residue obtained from a suitable solvent, such as pentane, diethyl ether, isopropyl ether, chloroform, dichloromethane, ethyl acetate, acetone or their combinations or subjecting it to one of the purification methods, such as column chromatography (e.g. flash chromatography) on a suitable support material such as alumina or silica gel using eluent such as dichloromethane, ethyl acetate, hexane, methanol, acetone and their combinations. Preparative LC-MS method is also used for the purification of molecules described herein.

Salts of compound of formula I are obtained by dissolving the compound in a suitable solvent, for example in a chlorinated hydrocarbon, such as methyl chloride or chloroform or a low molecular weight aliphatic alcohol, for example, ethanol or isopropanol, which was then treated with the desired acid or base as described in Berge S. M. et al. "Pharmaceutical Salts, a review article in Journal of Pharmaceutical sciences volume 66, page 1-19 (1977)" and in handbook of pharmaceutical salts properties, selection, and use by P. H. Einrich Stahland Camille G. wermuth, Wiley-VCH (2002).

The stereoisomers of the compounds of formula I of the present invention may be prepared by stereospecific syntheses or resolution of the achiral compound using an optically active amine, acid or complex forming agent, and separating the diastereomeric salt/complex by fractional crystallization or by column chromatography.

The following examples are provided to further illustrate the present invention and therefore should not be construed in any way to limit the scope of the present invention. All ¹HNMR spectra were determined in the solvents indicated and chemical shifts are reported in δ units downfield from the internal standard tetramethylsilane (TMS) and interproton coupling constants are reported in Hertz (Hz).

EXAMPLES

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques, generally using a mobile phase with suitable polarity. The following abbreviations are used in the text: DMSO-d6: Hexadeuterodimethyl sulfoxide; DMSO: Dimethylsulfoxide, CDI: 1,1'-Carbonyldiimidazole, DMF: N,N-dimethyl formamide, DMA: Dimethylacetamide, HBTU: 2-(1H-Benzotriazole-1-yl)-1,1,3,3-tetra methyluronium hexafluorophosphate, THF: Tetrahydrofuran, DCM: Dichloromethane, EDC: 1-Ethyl-3-(3-dimethylaminopropyl)carbodiimide, HATU: O-(7-Azabenzotriazol-1-yl)-N,N,N',N'-tetramethyluronium hexafluorophosphate, DIPEA: N,N-Diisopropyl ethyl amine, HOBT: 1-Hydroxy-1H-benzotriazole, J: Coupling constant in units of Hz, RT or rt: room temperature (22-26° C.), Aq.: aqueous, AcOEt: ethyl acetate, equiv. or eq.: equivalents and hr. or h: hour(s);

The following examples demonstrate preparation of few representative compounds embodied in formula (I); however, the same should not be construed as limiting the scope of the invention.

Intermediates

Intermediate-i: Preparation of (3-aminophenyl)(azetidin-1-yl)methanone

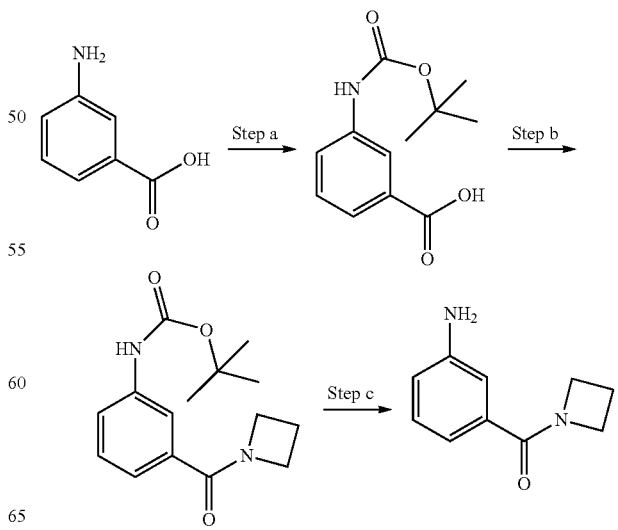

Step a: Synthesis of 3-((tert-butoxycarbonyl)amino)benzoic acid

To a stirred solution of 3-aminobenzoic acid (5 g, 36.5 mmol) in water (40.0 ml) was added aq. solution of sodium hydroxide (2.187 g, 54.7 mmol) followed by (BOC)₂O (10.16 ml, 43.8 mmol) in dioxane (20.0 ml) under ice cooling. The mixture was stirred under ice cooling for 30 min and further at room temperature for 12 hrs. To the reaction mixture ethyl acetate (50.0 ml) was added and the aq. layer was separated. The aq. layer was acidified up to pH 4 using 2N HCl and precipitated crystals were collected by filtration (7.2 gm).

$^1$H NMR (400 MHz, DMSO-d$_6$) δ 12.80 (brs, 1H), 9.54 (s, 1H), 8.14 (s, 1H), 7.62 (dd, 1H, J=0.8 Hz, J=8 Hz), 7.54-7.52 (m, 1H), 7.35 (t, 1H, J=7.6 Hz), 1.48 (s, 9H).

Step b: Synthesis of tert-butyl (3-(azetidine-1-carbonyl)phenyl) carbamate

To a stirred solution of 3-((tert-butoxycarbonyl)amino) benzoic acid (1.5 g, 6.32 mmol) in DMF (15 ml) were added N,N-diisopropyl ethylamine (2.208 ml, 12.64 mmol) and o-Benzotriazol-1-yl-tetramethyluronium hexafluorophosphate (2.398 g, 6.32 mmol) followed by azetidine hydrochloride (1.183 g, 12.64 mmol) at room temperature, under nitrogen atmosphere. The reaction was stirred at room temperature for 24 h and monitored by TLC. To the reaction mixture, water (25.0 ml) was added and extracted with ethyl acetate (30 ml×3). The aqueous layer was re-extracted with ethyl acetate. All organic layers were combined and washed with cold water (20.0 ml) and brine (20 ml); dried over sodium sulphate and solvent was evaporated under vacuum to get the titled compound (1.1 gm).

$^1$H NMR (400 MHz, DMSO-d$_6$) δ 9.48 (s, 1H), 7.74-7.73 (m, 1H), 7.56-7.52 (m, 1H), 7.31 (t, 1H, J=8 Hz), 7.19-7.16 (m, 1H), 4.25 (t, 2H, J=8 Hz), 4.01 (t, 2H, J=7.6), 2.32-2.22 (m, 2H), 1.47 (s, 9H). ESI-MS: [m/z: 277.09 (M+1)].

Step c: Synthesis of (3-aminophenyl)(azetidin-1-yl)methanone

To a stirred solution of tert-butyl (3-(azetidine-1-carbonyl)phenyl) carbamate (600 mg, 2.171 mmol) in DCM (5.0 ml) was added trifluoroacetic acid (0.167 ml, 2.171 mmol) at 0° C. under nitrogen atmosphere. Reaction was stirred at room temperature for 1 hr. Solvent evaporated up to dryness and the residual solid was dissolved in DCM (20 ml) and washed with saturated solution of NaHCO₃. DCM layer was dried over sodium sulphate and evaporated under vacuum. Resulting solid was washed with pentane and ether to give the titled compound (310 mg).

$^1$H NMR (400 MHz, DMSO-d$_6$) δ 7.04 (t, 1H, J=8 Hz), 6.80 (t, 1H, J=2 Hz), 6.70-6.67 (m, 1H), 6.65-6.62 (m, 1H), 5.24 (s, 2H), 4.25 (t, 2H, J=7.6 Hz), 3.98 (t, 2H, J=7.6 Hz), 2.24-2.18 (m, 2H). GCMS: 176.13 [M+].

Intermediate-ii: Synthesis of 2-(3-aminophenyl)-N-cyclopropylacetamide

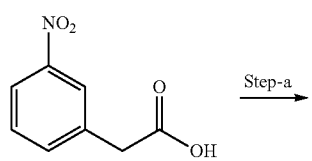

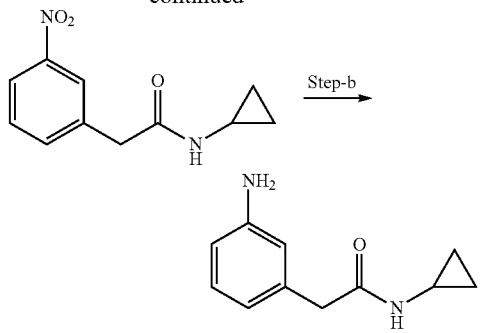

Step a: Synthesis of N-cyclopropyl-2-(3-nitrophenyl)acetamide

To a stirred solution of 2-(3-nitrophenyl)acetic acid (2.5 g, 13.80 mmol) in DMF (20 ml) was added HBTU (4.19 g, 16.56 mmol), N,N-diisopropyl ethylamine (4.82 ml, 27.6 mmol) followed by addition of cyclopropylamine (1.946 ml, 27.6 mmol) at room temperature under nitrogen atmosphere. Reaction mixture was stirred at room temperature for 16 hrs, the reaction mixture was diluted with water (80.0 mL) and extracted with ethyl acetate (20.0 ml×3). Combined organic layers were washed with cold water (20.0 ml) and brine (10.0 ml); dried over sodium sulphate. The solvent was evaporated under vacuum to give the crude compound which was purified by column chromatography to afford titled compound (2.41 gm).

$^1$H NMR (400 MHz, DMSO-d$_6$) δ 8.25 (d, 1H, J=2.4 Hz), 8.12-8.09 (m, 1H), 7.67 (d, 1H, J=7.6 Hz), 7.60 (t, 1H, J=7.6 Hz), 3.52 (s, 2H), 2.63-2.58 (m, 1H), 0.63-0.55 (m, 2H), 0.41-0.37 (m, 2H). GCMS: 221.09 [M+]

Step b: Synthesis of 2-(3-aminophenyl)-N-cyclopropylacetamide

To a stirred solution of N-cyclopropyl-2-(3-nitrophenyl) acetamide (2.4 g, 10.90 mmol) in methanol (25.0 ml) was added slurry of Pd/C (10%, 0.232 g), To the above reaction mixture, triethylsilane (8.70 ml, 54.5 mmol) was added slowly drop wise at room temperature (reaction was exothermic) and then the reaction mixture was stirred at room temperature for 1 hr. The reaction mixture was filtered through celite bed and the filtrate was evaporated under vacuum. The residue was triturated in hexane, the solid obtained was filtered and dried under vacuum to give the product (1.95 gm).

$^1$H NMR (400 MHz, DMSO-d$_6$) δ 8.03 (s, 1H), 6.90 (t, 1H, J=7.6 Hz), 6.49-6.35 (m, 1H), 5.02 (s, 2H), 3.15 (s, 2H), 2.60-2.59 (m, 1H), 0.69-0.58 (m, 2H), 0.48-0.38 (m, 2H). GCMS: 190.11 [M+].

Intermediate-iii: Synthesis of 2-(3-aminophenoxy)-N-cyclopropylacetamide

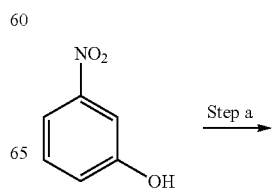

-continued

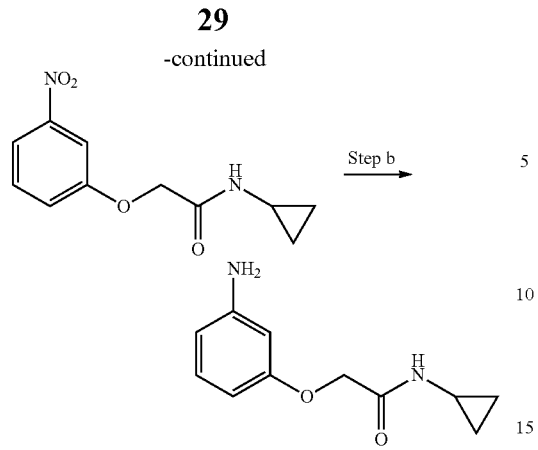

Step a: Synthesis of N-cyclopropyl-2-(3-nitrophenoxy)acetamide

A mixture of 3-nitrophenol (4 g, 28.8 mmol), 2-chloro-N-cyclopropylacetamide (4.61 g, 34.5 mmol), $K_2CO_3$ (7.95 g, 57.5 mmol) and 18-CROWN-6 (0.228 g, 0.863 mmol) in N,N-Dimethylformamide (30.0 ml) was stirred under $N_2$ atmosphere for 18 hrs at 50° C. After cooling to RT, the reaction mixture was partitioned between EtOAc (250 ml) and water (250 ml). Aq. phase was re-extracted with EtOAc (200 ml). Combined organic layer was washed with brine (100 ml), dried over sodium sulphate and the solvent was evaporated under vacuum. Crude residue was purified by flash chromatography to obtain N-cyclopropyl-2-(3-nitrophenoxy)acetamide (4.21 gm).

$^1$H NMR (400 MHz, DMSO-$d_6$) δ 7.85-7.82 (m, 1H), 7.76-7.74 (m, 1H), 7.59 (t, J=8.4 Hz, 1H), 7.44-7.41 (m, 1H), 4.60 (s, 2H), 2.72-2.66 (m, 1H), 0.67-0.60 (m, 2H), 0.50-0.46 (m, 2H). GCMS: 236.14 [M+].

Step b: Synthesis of 2-(3-aminophenoxy)-N-cyclopropylacetamide

Triethylsilane (27.0 ml, 169 mmol) was added dropwise to a suspension of N-cyclopropyl-2-(3-nitrophenoxy)acetamide (4 g, 16.93 mmol) and Pd/C (10%, 400 mg) in MeOH (50 ml). Resulting suspension was stirred at RT for 20 min. and filtered through celite. The filtrate was evaporated under vacuum and triturated in hexane to obtain the crystals which were collected by filtration to afford 2-(3-aminophenoxy)-N-cyclopropylacetamide (2.86 gm).

$^1$H NMR (400 MHz, DMSO-$d_6$) δ 6.89 (t, J=8.0 Hz, 1H), 6.18-6.12 (m, 2H), 6.07-6.04 (m, 1H), 5.21 (brs, 1H), 5.08 (s, 2H), 4.29 (s, 2H), 2.70-2.66 (m, 1H), 0.62-0.59 (m, 2H), 0.50-0.45 (m, 1H). GCMS: 206.11 [M+].

Intermediate-iv: Synthesis of (3-aminophenyl)(1,1-dioxidothiazolidin-3-yl)methanone

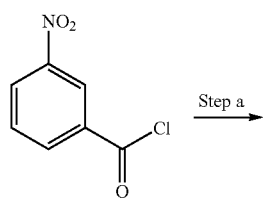

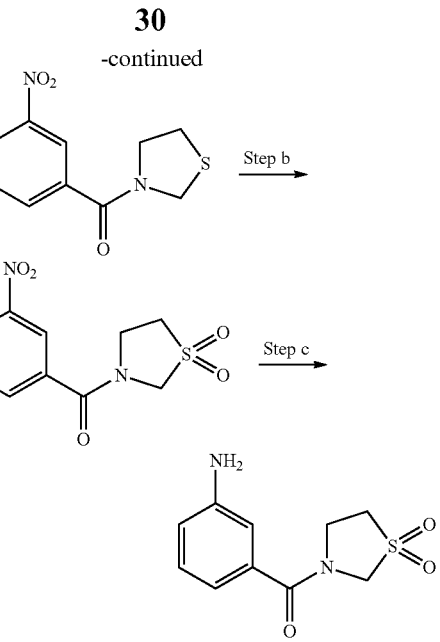

Step a: Synthesis of (3-nitrophenyl)(thiazolidin-3-yl)methanone

To a stirred solution of 3-nitrobenzoyl chloride (5.00 g, 26.9 mmol) in DCM (50 ml), thiazolidine (3.60 g, 40.4 mmol) was added at 0° C. Triethylamine, (7.51 ml, 53.9 mmol) was added dropwise into the reaction mixture over 5 min and the reaction mixture was stirred at RT for 1 hr. Reaction mixture was diluted with cold water. Organic phase was separated and aq. phase was extracted using DCM (3×10.0 ml). Combined organic layer was washed with brine (100 ml), dried over sodium sulphate and the solvent was evaporated under vacuum to afford the title compound (5.0 gm).

$^1$HNMR (400 MHz, DMSO-d6), δ 8.35-8.31 (m, 2H), 8.01-7.98 (m, 1H), 7.79 (t, 1H, J=8 Hz), 4.65-4.52 (m, 2H), 3.84-3.70 (m, 2H), 3.08-2.97 (m, 2H). GCMS: 237.96 [M+].

Step b: Synthesis of (1,1-dioxidothiazolidin-3-yl)(3-nitrophenyl)methanone

To a stirred solution of (3-nitrophenyl)(thiazolidin-3-yl)methanone (4 g, 16.79 mmol) in acetic acid (30 ml), $H_2O_2$(12 ml, 30% solution) was added, the resulting mixture was stirred at 100° C. for 3 hrs. The mixture was concentrated under vacuum and the residue was treated MeOH. Resulting solid was filtered off and dried under vacuum to afford the titled compound (3 gm).

$^1$HNMR (400 MHz, DMSO-d6), δ 8.39-8.32 (m, 2H), 7.99-7.97 (m, 1H), 7.79 (t, 1H J=7.6 Hz), 4.69 (s, 2H), 4.20-3.90 (m, 2H), 3.51-3.47 (m, 2H). ESI-MS: [m/z: 270.08 (M+1)].

Step c: Synthesis of (3-aminophenyl)(1,1-dioxidothiazolidin-3-yl)methanone

A solution of (1,1-dioxidothiazolidin-3-yl)(3-nitrophenyl)methanone (3 g, 11.10 mmol) in MeOH (30 ml) and 10% Pd—C (300 mg) was stirred under $H_2$ (1 atm) for overnight. Reaction mixture was filtered through celite pad and the filtrate was evaporated under vacuum to afford the titled compound (2.3 gm).

¹HNMR (400 MHz, DMSO-d6), δ 7.12-7.08 (m, 1H), 6.84-6.70 (m, 1H), 6.61-6.59 (d, 1H, J=8 Hz), 5.35 (s, 2H), 4.60 (s, 2H), 4.05-4.00 (m, 2H), 3.45-3.41 (m, 2H). ESI-MS: [m/z=241.71 (M+1)].

Intermediate-v: Synthesis of (3-aminophenyl)(1,1-dioxidothiomorpholino) methanone

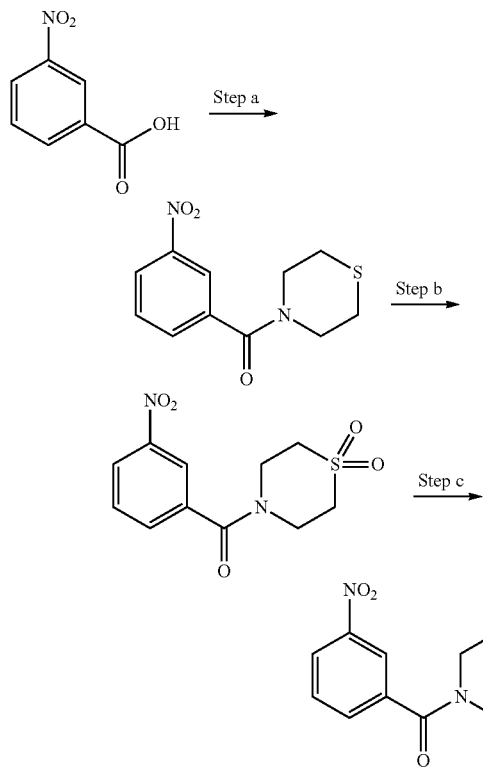

Step a: Synthesis of (3-nitrophenyl)(thiomorpholino)methanone

To a suspension of 3-nitrobenzoic acid (6.5 g, 38.9 mmol) in DCM (50 ml) was added oxalyl chloride (5 ml, 58.1 mmol) and DMF (0.5 ml, 6.46 mmol), respectively. The resulting mixture was stirred at room temperature until a clear solution was formed. The solvent was removed under vacuum. 3-Nitrobenzoyl chloride thus obtained was dissolved in DCM (50 ml), Et₃N (10.13 ml, 72.7 mmol) and thiomorpholine (5 g, 48.5 mmol) were added at 0° C. Reaction mixture was gradually allowed to reach to room temperature and stirred for 2 hrs. The reaction mixture was concentrated under vacuum and cold water was added to the residue, the solid obtained was filtered and dried under vacuum to give the product (9.2 gm).

¹HNMR (400 MHz, DMSO-d6), δ 8.30-8.28 (m, 1H), 8.26-8.22 (m, 1H), 7.87-7.84 (m, 1H), 7.74 (t, 1H, J=8 Hz), 3.88 (brs, 2H), 3.52 (brs, 2H), 2.71 (brs, 2H), 2.60 (brs, 2H). ESI-MS: [m/z=252.7 (M+1)].

Step b: Synthesis of (1,1-dioxidothiomorpholino) (3-nitrophenyl) methanone

To a stirred solution of (3-nitrophenyl)(thiomorpholino) methanone (12 g, 47.6 mmol) in acetic acid (80 ml) was added H₂O₂(45 ml, 30% solution), reaction mixture was heated at 90° C. for 3 hr. Solvents were evaporated under vacuum, the residue was dissolved in DCM:MeOH (20:20 mL) and passed through a celite bed. The filtrate was concentrated under vacuum to obtain the crude product (7.3 gm).

¹HNMR (400 MHz, DMSO-d6), δ 8.41-8.40 (m, 1H), 8.33-8.30 (m, 1H), 7.94-7.91 (m, 1H), 7.76 (t, 1H, J=8 Hz), 4.03 (brs, 2H), 3.66 (brs, 2H), 3.33-3.16 (m, 4H). ESI-MS: [m/z=284.6 (M+1)].

Step c: Synthesis of (3-aminophenyl) (1,1-dioxidothiomorpholino)methanone

To a stirred solution of (1,1-dioxidothiomorpholino)(3-nitrophenyl)methanone (3.5 g, 12.31 mmol) in MeOH (20 ml) was added Pd—C (10%, 350 mg) followed by slow addition of triethylsilane (8.5 ml) at RT. Reaction was stirred at RT for 1 h. Reaction mixture was filtered through celite and washed with methanol (50 ml). Filtrate was concentrated under vacuum and triturated in hexane to get crude product (2.8 gm).

¹HNMR (400 MHz, DMSO-d6), δ 7.08-7.05 (t, 1H, J=7.6 Hz), 6.63-6.56 (m, 3H), 5.28 (s, 2H), 3.94-3.73 (m, 4H), 3.16 (brs, 4H). GCMS: 254.09 [M+]

Intermediate-vi: Synthesis of 2-(3-aminophenyl)-2-methylpropanamide

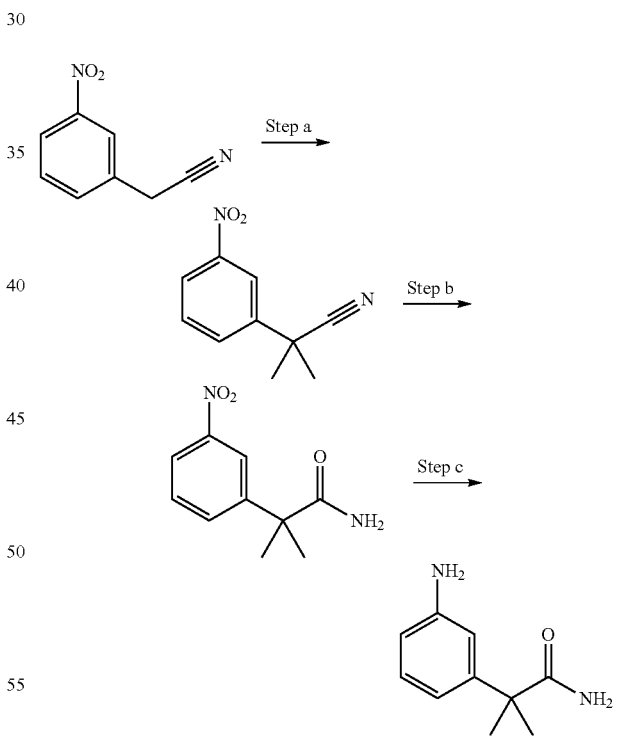

Step a: Synthesis of 2-methyl-2-(3-nitrophenyl)propanenitrile

To an ice-cold slurry of 50% NaH (6.84 g, 171 mmol) in anhydrous THF (30.0 ml) was slowly added a solution of 2-(3-nitrophenyl) acetonitrile (4.2 g, 25.9 mmol) in anhydrous THF (30 ml). After 30 min, methyl iodide (12.63 ml, 202 mmol) was slowly added. The reaction mixture was allowed to warm to room temperature and stirred overnight. It was then quenched with ice-water. The reaction mixture was then extracted with ethyl acetate, the organic layer was separated and washed with water, dried over anhydrous sodium sulphate; filtered and concentrated to get crude oil. The crude oil was purified by column chromatography over silica gel by eluting with ethyl acetate/hexane (5:95) gave 2-methyl-2-(3-nitrophenyl) propanenitrile (2.1 g).

$^1$HNMR (400 MHz, CDCl3), δ 8.33-8.32 (m, 1H), 8.24-8.21 (m, 1H), 7.92-7.89 (m, 1H), 7.63 (t, J=8.00 Hz, 1H), 1.82 (s, 6H). GCMS: 190.11[M+]

Step b: Synthesis of 2-methyl-2-(3-nitrophenyl)propanamide

To a solution of 2-methyl-2-(3-nitrophenyl)propanenitrile (1.5 g, 7.89 mmol) in 2-propanol was added benzyltriethyl ammonium chloride (0.054 g, 0.237 mmol) and 25% aq. KOH solution (5.0 ml). Resulting solution was stirred for 5 min. and H$_2$O$_2$(2.5 ml, 30% aq. solution) was added (slow addition). Reaction mixture was heated at 75° C. for 4 hr. Solvent was evaporated under vacuum and residue was suspended in water (200 ml). Precipitate was filtered and dried to obtain 2-methyl-2-(3-nitrophenyl) propanamide (0.98 gm).

$^1$HNMR (400 MHz, DMSO-d6), δ 8.15-8.10 (m, 2H), 7.80 (d, J=7.6 Hz, 1H), 7.64 (t, J=8.00 Hz, 1H), 7.11 (brs., 1H), 7.05 (brs., 1H) 1.50 (s, 6H).

Step c: Synthesis of 2-(3-aminophenyl)-2-methylpropanamide

To a stirred solution of 2-methyl-2-(3-nitrophenyl) propanamide (0.9 g, 4.32 mmol) in methanol was added Pd—C (10%, 0.23 g) followed by slow addition of triethylsilane (6.90 ml, 43.2 mmol) at RT. Reaction was stirred at same temperature for 25 min. The reaction mixture was filtered through celite bed and washed with methanol (50 ml). Filtrate was collected and concentrated under vacuum to obtain 2-(3-aminophenyl)-2-methylpropanamide (0.611 g).

$^1$HNMR (400 MHz, DMSO-d6), δ 6.93 (t, J=8.0 Hz, 1H), 6.78 (brs., 1H), 6.72 (brs., 1H), 6.55-6.47 (m, 2H), 6.41-6.38 (m, 1H), 4.98 (s, 2H), 1.35 (s, 6H). GCMS: 178.15 [M+].

Intermediate-vii: Synthesis of 2-(3-aminophenyl)-2,2-difluoroacetamide

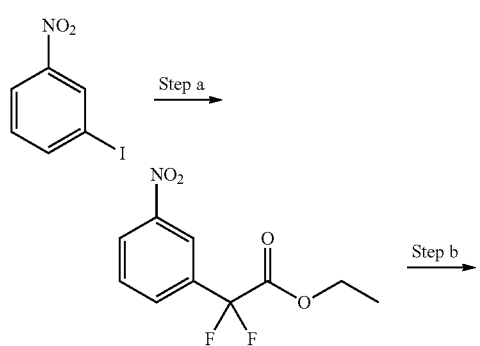

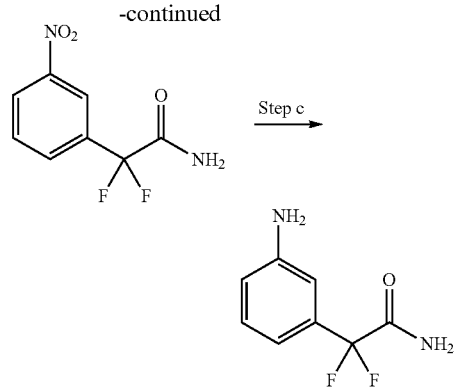

Step a: Synthesis of Ethyl 2,2-difluoro-2-(3-nitrophenyl)acetate

To a solution of 1-iodo-3-nitrobenzene (1.450 g, 5.82 mmol) and ethyl 2-bromo-2,2-difluoroacetate (1.3 g, 6.40 mmol) in anhydrous DMSO (10 ml) was added Copper powder (0.740 g, 11.64 mmol). The mixture was purged with N$_2$ and heated at 70° C. in a sealed vial for 17 h. After being cooled to room temperature, the reaction mixture was poured into 20% aqueous NH$_4$Cl solution (100 mL) and was extracted with EtOAc (2×100 mL). The organic extract was washed with brine (2×30 mL), dried over Na$_2$SO$_4$ and concentrated. The residue was purified by flash chromatography to obtain ethyl 2, 2-difluoro-2-(3-nitrophenyl) acetate (0.714 g).

$^1$HNMR (400 MHz, DMSO-d6), δ 8.47 (d, J=6.8 Hz, 1H), 8.33 (s, 1H), 8.09 (dd, J=0.8 & 8 Hz, 1H), 7.89 (t, J=8.4 Hz, 1H), 4.3 (q, J=9.2 Hz, 2H), 1.24 (t, J=6.4 Hz, 3H). GCMS: 245.15 [M+].

Step b: Synthesis of 2,2-difluoro-2-(3-nitrophenyl) acetamide

A solution of ethyl 2, 2-difluoro-2-(3-nitrophenyl) acetate (0.701 g, 2.86 mmol) in Methanolic ammonia (7M, 20.0 ml) was taken in sealed tube. Resulting mixture was heated at 75° C. for 3 hrs. The reaction mixture was concentrated under vacuum and cold water was added to obtain the precipitate. Solid was filtered to obtain 2, 2-difluoro-2-(3-nitrophenyl) acetamide (0.515 g).

$^1$HNMR (400 MHz, DMSO-d6), δ 8.55 (brs., 1H), 8.44-8.37 (m, 2H), 8.18 (brs., 1H), 8.04 (d, J=7.6 Hz, 1H), 7.86 (t, J=8 Hz, 1H). GCMS: 215.98 [M+]

Step c: Synthesis of 2-(3-aminophenyl)-2,2-difluoroacetamide

To a stirred solution of 2,2-difluoro-2-(3-nitrophenyl) acetamide (0.5 g, 2.313 mmol) in methanol (20 ml) was added Pd—C (100 mg) followed by slow addition of triethylsilane (3.7 ml, 23.13 mmol) at RT. The reaction was stirred at same temperature for 30 min. The reaction mixture was filtered through celite bed and washed with methanol (50 ml). Filtrate was collected and concentrated under vacuum to get 2-(3-aminophenyl)-2, 2-difluoroacetamide (0.301 g).

$^1$HNMR (400 MHz, DMSO-d6), δ 8.21 (brs., 1H), 7.90 (brs., 1H), 7.11 (t, J=7.6 Hz, 1H), 6.75 (s, 1H), 6.67 (d, J=7.6 Hz, 2H), 5.42 (s, 2H). GCMS: 186.01 [M+].

Intermediate-viii: Synthesis of 2-(3-aminophenyl)-N,N-dimethylacetamide

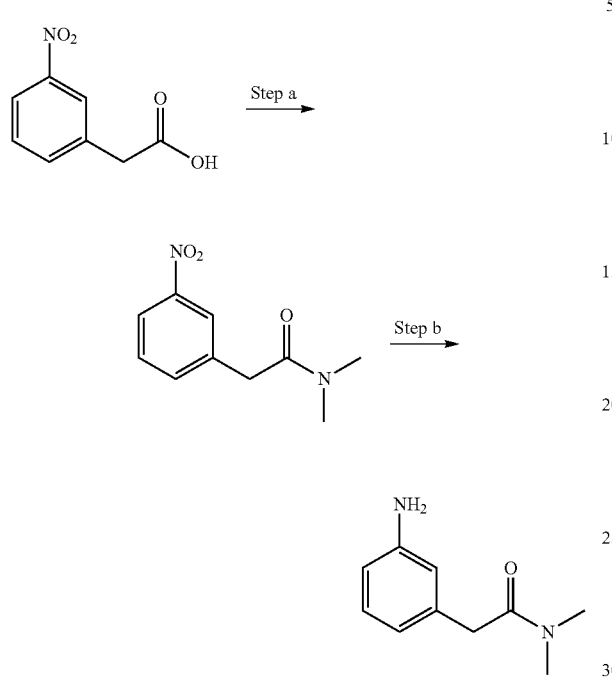

Step a: Synthesis of N,N-dimethyl-2-(3-nitrophenyl)acetamide

To a stirred solution of 2-(3-nitrophenyl) acetic acid (0.2 g, 1.104 mmol) in THF (6 ml) was added CDI (0.269 g, 1.656 mmol). resulting mixture was heated at 50° C. for 1 hr, cooled to room temperature and then dimethyl amine hydrochloride (0.108 g, 1.325 mmol) and Et$_3$N (0.15 ml, 1.104 mmol) were added sequentially. Resulting reaction mixture was stirred for 24 h at ambient temperature. Solvents were evaporated under vacuum. The residue was purified by flash chromatography to obtain N,N-dimethyl-2-(3-nitrophenyl) acetamide (0.192, 84% yield).

$^1$HNMR (400 MHz, DMSO-d6), δ 8.11-8.08 (m, 2H), 7.68-7.58 (m, 2H), 3.89 (s, 2H), 3.05 (s, 3H), 2.85 (s, 3H). GCMS: 208.12 [M+].

Step b: Synthesis of 2-(3-aminophenyl)-N,N-dimethylacetamide

To a stirred solution of N,N-dimethyl-2-(3-nitrophenyl) acetamide (1.6 g, 7.68 mmol) in methanol (20 ml) was added 10% Pd—C (0.327 g) followed by slow addition of triethylsilane (12.3 ml, 77 mmol) at RT. Reaction was stirred at same temperature for 30 min. The reaction mixture was filtered through celite bed. The filtrate was concentrated to get 2-(3-aminophenyl)-N, N-dimethylacetamide (1.21 g, 88% yield).

$^1$HNMR (400 MHz, DMSO-d6), δ 6.92 (t, J=7.6 Hz, 1H), 6.43-6.34 (m, 3H), 5.05 (s, 2H), 3.49 (s, 2H), 2.95 (s, 3H), 2.81 (s, 3H). GCMS: 178.15 [M+].

Intermediate-ix: Synthesis of 3-(3-aminophenyl)-N-methylpropanamide

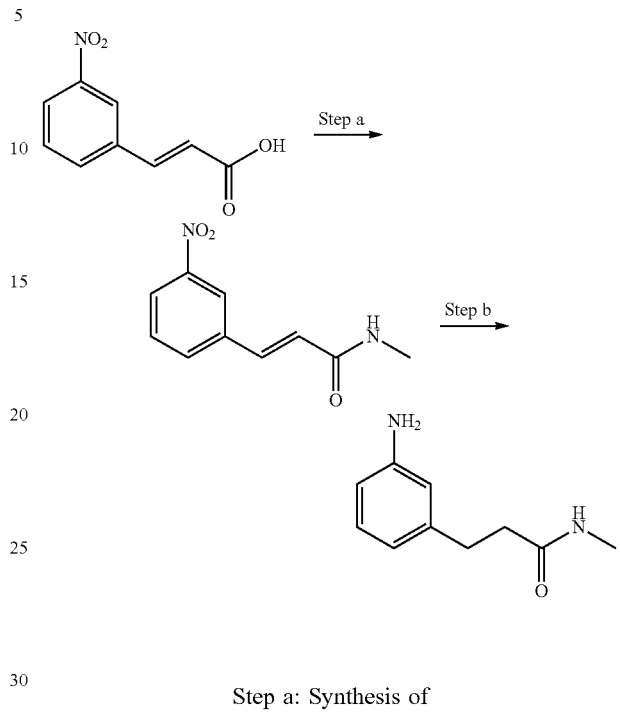

Step a: Synthesis of N-methyl-3-(3-nitrophenyl)acrylamide

To a solution of 3-nitrocinnamic acid (5.0 g) in dry Toluene (100 ml), oxalyl chloride (11.33 ml) was carefully added, followed by dry DMF (0.1 mL). The resulting yellow solution was refluxed for 3 hrs and then evaporated to dryness, to get the 3-nitro cinnamoyl chloride as a solid residue, This solid residue was dissolved in THF, the resulting solution was cooled at 0° C., and 2M methylamine (13 ml) was added to the reaction mixture, the reaction mixture was stirred for 30 min. Solvents were evaporated under vacuum, the crude material was re-crystallised from diethylether to afford the title compound (4 gm).

$^1$HNMR (400 MHz, DMSO-d6), δ 8.38 (s, 1H), 8.26-8.25 (d, 1H J=4.4 Hz), 8.20-8.18 (m, 1H), 8.02-8.00 (d, 1H J=7.6 Hz), 7.72-7.68 (m, 1H) 7.56-7.52 (d, 1H J=16 Hz), 6.85-6.81 (d, 1H, J=15.6 Hz), 2.71-2.70 (d, 3H J=4.4 Hz). GCMS: 207.05 [M+].

Step b: Synthesis of 3-(3-aminophenyl)-methyl propanamide

To a stirred solution of N-methyl-3-(3-nitrophenyl)acrylamide (4 g, 19.40 mmol) and Pd—C (10%, 200 mg) in MeOH (30.0 ml) was added triethylsilane (31 ml, 194 mmol) dropwise at room temperature over a period of 1 hr. Reaction progress was monitored by TLC. After completion of reaction, reaction mixture was filtered through celite bed. The filtrate was concentrated under vacuum to give the title compound (2.5 gm).

$^1$HNMR (400 MHz, DMSO-d6), δ 7.76-7.75 (d, 1H, J=4 Hz), 6.96-6.88 (m, 1H), 6.38-6.32 (m, 3H), 5.10 (s, 2H), 2.62-2.58 (t, 2H J=6.8 Hz), 2.55-2.54 (d, 3H J=4.4 Hz) 2.32-2.25 (t, 2H J=6.9 Hz). GCMS: 177.88 [M+].

Intermediate-x: Synthesis of (3-aminophenyl)(4-hydroxypiperidin-1-yl)methanone

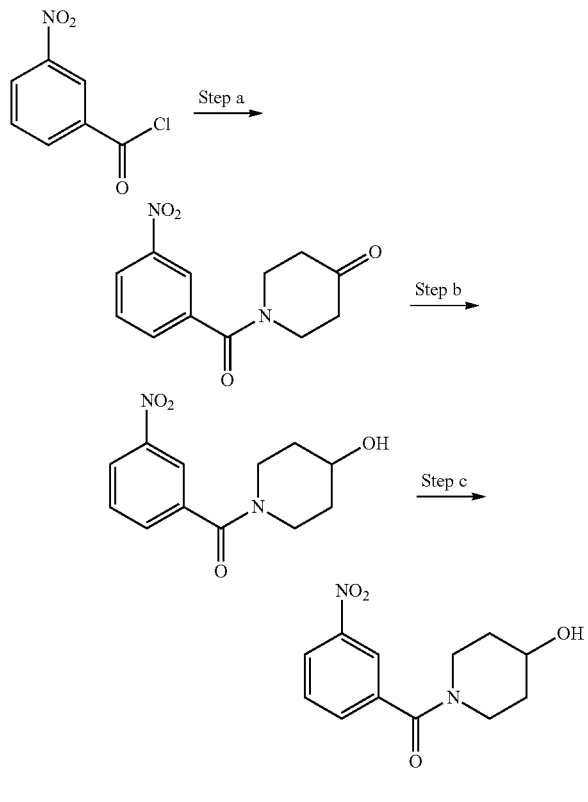

Step a: Synthesis of (4-hydroxypiperidin-1-yl)(3-nitrophenyl) methanone

To a stirred solution of 3-nitrobenzoyl chloride (10.0 g, 53.9 mmol) in DCM (10 ml) was added piperidin-4-one hydrochloride (10.96 g, 81.0 mmol) and triethylamine (22.53 ml, 162.0 mmol). The reaction mixture was stirred at room temperature for 30 min and evaporated to dryness. The crude material was treated with diethyl ether, solid obtained was filtered and dried under vacuum to give the title compound (9.0 gm).

$^1$HNMR (400 MHz, CDCl$_3$), δ 8.35-8.32 (m, 2H), 7.82 (d, 1H, J=7.6 Hz), 7.69-7.65 (m, 1H), 4.12 (bs, 2H), 3.77 (bs, 2H), 2.55 (bs, 4H). GCMS: 248.11 [M+].

Step-b: Synthesis of (4-hydroxypiperidin-1-yl)(3-nitrophenyl)methanone

To a stirred solution of 1-(3-nitrobenzoyl) piperidin-4-one (1.5 g, 6.04 mmol) in THF: Methanol (20 mL, 1:1), was added sodium borohydride (0.229 g, 6.04 mmol) at room temp. Reaction mixture was stirred at room temperature for 30 min. and diluted with water (20.0 ml), extracted with ethyl acetate (3×30.0 ml). Combined organic layer was dried over sodium sulphate and the solvents were removed under vacuum to obtain the title compound. (1 gm).

$^1$HNMR (400 MHz, DMSO-d6), δ 8.30-8.27 (m, 1H), 8.17-8.16 (m, 1H), 7.85-7.83 (m, 1H), 7.74 (t, 1H, J=7.6 Hz), 4.81 (bs, 1H), 3.98 (bs, 1H), 3.77-3.72 (m, 1H), 3.42 (bs, 1H), 3.28 (bs, 1H), 3.13 (bs, 1H), 1.68 (bs, 1H), 1.53 (bs, 1H) 1.42 (bs, 1H) 1.35 (bs, 1H). GCMS: 250.19 [M+].

Step-c: Synthesis of (3-aminophenyl)(4-hydroxypiperidin-1-yl) methanone

To a stirred solution of (4-hydroxypiperidin-1-yl)(3-nitrophenyl)methanone (1 g, 4.00 mmol) and Pd—C (10%, 0.425 g) in Methanol (10 ml) was added triethylsilane (3.19 ml, 19.98 mmol) dropwise at room temperature. The reaction mixture was filtered through celite bed. The filtrate was concentrated under vacuum to give the title compound. (0.8 gm)

$^1$HNMR (400 MHz, DMSO-d6), δ 7.03 (t, 1H, J=8 Hz), 6.58 (dd, 1H, J=8.0 and 1.6 Hz), 6.51-6.50 (m, 1H), 6.42 (d, 1H, J=7.2 Hz), 5.23 (s, 1H), 4.78 (d, 1H, J=3.6 Hz), 3.98 (bs, 1H), 3.73-3.69 (m, 1H), 3.50 (bs, 1H), 3.13 (bs, 2H), 1.70 (bs, 2H), 1.30 (bs, 2H). GCMS: 220.15 [M+].

Intermediate-xi: Synthesis of 3-Amino-N-(oxetan-3-yl)benzamide

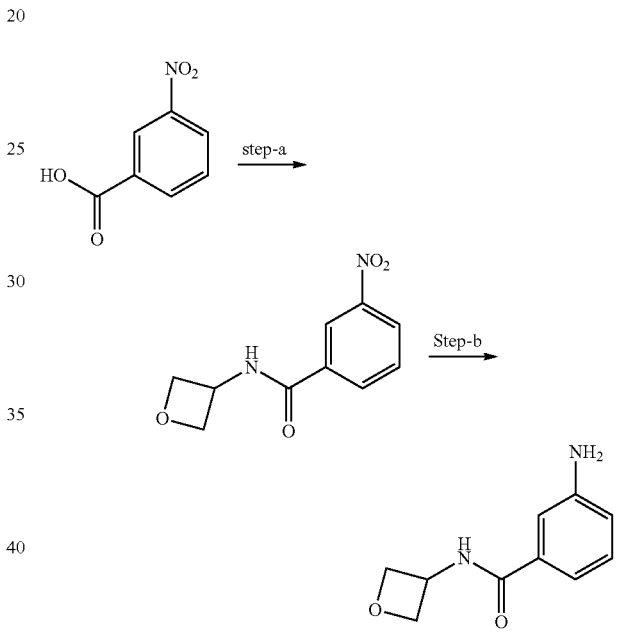

Step-a: Synthesis of 3-Nitro-N-(oxetan-3-yl)benzamide

3-Nitrobenzoic acid (0.50 g, 2.99 mmol), oxetan-3-amine (0.219 g, 2.99 mmol) were taken in pyridine (0.5 ml) and under nitrogen atmosphere and EDC.HCl (0.574 g, 2.99 mmol) was added. The reaction mixture was stirred at room temperature for 10 hrs. After completion of reaction, the reaction mixture was diluted with water (5 ml) and extracted with ethyl acetate (2×5 ml). Combined organic layer was dried over sodium sulfate and concentrated under vacuum to afford the title compound (600 mg).

$^1$HNMR (400 MHz, CDCl$_3$): δ 8.64 (t, 1H, J=2 Hz), 8.43-8.40 (m, 1H), 8.21-8.18 (m, 1H), 7.85 (bs, 1H), 7.70 (t, 1H, J=8 Hz), 5.33-5.23 (m, 1H), 5.07 (t, 2H, J=7.2 Hz), 4.66 (t, 2H, J=6.8 Hz).

Step-b: Synthesis of 3-Amino-N-(oxetan-3-yl)benzamide

To a stirred solution of 3-Nitro-N-(oxetan-3-yl) benzamide (0.06 g, 0.270 mmol) in methanol (5 ml) was added Pd/C (2.87 mg) and the reaction mixture was stirred under hydrogen atmosphere for 20 min. The reaction mixture was diluted with methanol (10 ml) and the mixture was filtered through celite, and the filtrate was concentrated under vacuum to afford the title compound (48 mg).

¹HNMR (400 MHz, CDCl₃): δ 7.25-7.21 (m, 1H), 7.15-7.14 (m, 1H), 7.09-7.07 (m, 1H), 6.85-6.82 (m, 1H), 6.55 (bs, 1H), 5.29-5.08 (m, 1H), 5.06-4.98 (m, 2H), 4.64-4.60 (m, 2H), 3.95-3.85 (bs, 2H). GCMS: 192 (M+).

Intermediate-xii: Synthesis of
3-Amino-N-(tetrahydrofuran-3-yl) benzamide

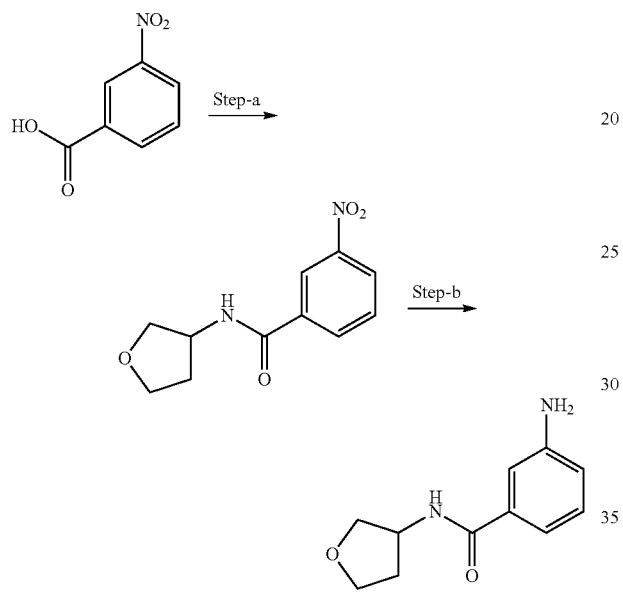

Step-a: Synthesis of
3-Nitro-N-(tetrahydrofuran-3-yl) benzamide

Tetrahydrofuran-3-amine (0.1 g, 1.148 mmol) and 3-nitrobenzoic acid (0.192 g, 1.148 mmol) were taken in pyridine (2 ml), to the mixture EDC.HCl (0.220 g, 1.148 mmol) was added, the reaction mixture was stirred under nitrogen for 10 hrs at room temperature. The reaction mixture was diluted with cold water (15 ml), extracted with ethyl acetate (2×10 ml). Combined organic layer was washed with satd. aq. sod bicarbonate and dil HCl, the organic layer was dried over sodium sulfate and concentrated under vacuum to afford the title product (240 mg).

¹HNMR (400 MHz, CDCl₃): □ 8.62-8.61 (m, 1H), 8.39-8.36 (m, 1H), 8.19-8.17 (m, 1H), 7.67 (t, 1H, J=8 Hz), 6.62 (d, 1H, J=6 Hz), 4.79-4.75 (m, 1H), 4.08-4.00 (m, 1H), 3.93-3.83 (m, 3H), 2.44-2.37 (m, 1H), 2.01-1.98 (m, 1H).

Step-b: Synthesis of
3-Amino-N-(tetrahydrofuran-3-yl) benzamide

3-Nitro-N-(tetrahydrofuran-3-yl) benzamide (0.24 g, 1.016 mmol) was taken in methanol (5 ml), added Pd—C (10%, 0.108 g) and the reaction mixture was stirred under hydrogen atmosphere for 2 hr at room temperature. After completion of the reaction, the reaction mixture was filtered and the filtrate was concentrated under vacuum to afford the crude product, which was purified by column chromatography eluting with 0-100% ethyl acetate in hexane to obtain the title compound (180 mg).

¹HNMR (400 MHz, CDCl₃): □ 7.21 (t, 1H, J=7.6 Hz), 7.13-7.12 (m, 1H), 7.05-7.03 (m, 1H), 6.82-6.80 (m, 1H), 6.24 (bs, 1H), 4.74-4.71 (m, 1H), 4.04-3.77 (m, 6H), 2.39-2.32 (m, 1H), 1.94-1.91 (m, 1H). GCMS: 206 (M+).

Intermediate-xiii: Synthesis of
2-(3-aminophenyl-2-hydroxyacetamide

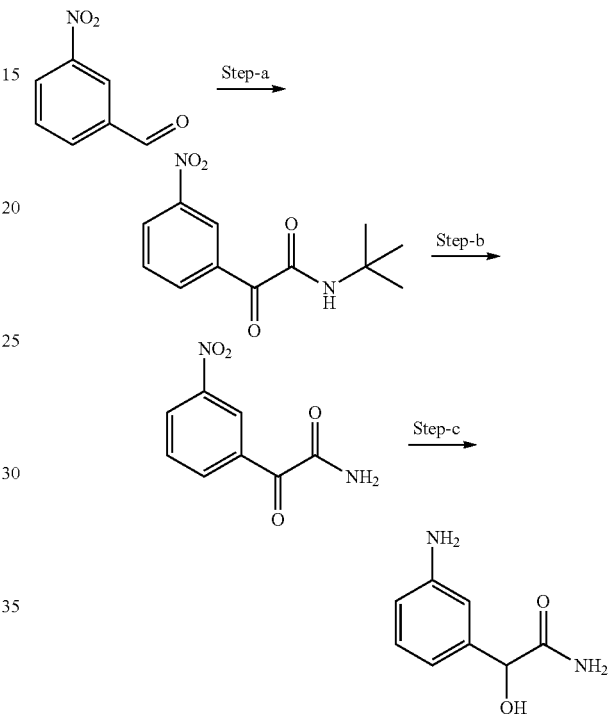

Step-a: Synthesis of (Tert-butyl)-2-(3-nitrophenyl)-2-oxoacetamide

Under nitrogen atmosphere, zinc chloride (8.12 g, 59.6 mmol) and molecular sieve (200 mg) were taken in THF (10 ml) at room temperature. To the above mixture 3-nitrobenzaldehyde (3.00 g, 19.85 mmol), N-methylhydroxylamine hydrochloride (2.65 g, 31.8 mmol) and sodium bicarbonate (2.67 g, 31.8 mmol) were added. The mixture was stirred at room temperature for 30 min., followed by addition of 2-isocyano-2-methylpropane (3.30 g, 39.7 mmol) and acetic acid (3.58 g, 59.6 mmol) and the reaction mixture was stirred for 48 hrs. Water (50 ml) was added and the mixture was extracted with ethyl acetate (2×50 ml). Combined organic layer was washed with aq. satd. sodium bicarbonate solution and water and dried over sodium sulfate. The mixture was concentrated under vacuum and the crude product obtained was purified by column chromatography to afford the yellow oil (2.4 gm).

¹HNMR (400 MHz, CDCl₃): □ 9.18 (t, 1H, J=2 Hz), 8.73-8.70 (m, 1H), 8.49-8.45 (m, 1H), 7.69 (t, 1H, J=8.0 Hz), 7.03 (bs, 1H), 1.48 (s, 9H).

Step-b: Synthesis of
2-(3-nitrophenyl)-2-oxoacetamide

Under nitrogen atmosphere, (tert-butyl)-2-(3-nitrophenyl)-2-oxoacetamide (1.50 g, 5.99 mmol) was taken in toluene (10 ml) at room temperature, tert-butyldimethylsilyl trifluoromethane sulfonate (1.378 ml, 5.99 mmol) was added and the reaction mixture was heated at 100° C. for 8 hrs. The reaction mixture was concentrated under vacuum and satd. sodium bicarbonate solution was added, the mixture was extracted with ethyl acetate (3×20 ml). Combined organic layer was dried over sodium sulfate and the mixture was concentrated under vacuum to afford the crude product, which was purified by column chromatography to afford yellow solid product (440 mg).

$^1$HNMR (400 MHz, CDCl$_3$): ☐ 9.20 (t, 1H, J=2 Hz), 8.74-8.72 (m, 1H), 8.52-8.49 (m, 1H), 7.73 (bs, 1H), 7.03 (bs, 1H), 5.78 (bs, 1H).

Step-c: Synthesis of
2-(3-aminophenyl-2-hydroxyacetamide

To a mixture of 2-(3-nitrophenyl)-2-oxoacetamide (1.00 g, 5.15 mmol), ammonium formate (0.974 g, 15.45 mmol) and methanol (20 ml) at 0° C., was added Pd/C (10%, 0.17 g) and the reaction mixture was stirred at room temperature for 18 hrs. The reaction mixture filtered through celite, the filtrate was concentrated under vacuum. The residue was taken in ethyl acetate and filtered through celite and concentrated under vacuum to afford the yellow solid product (330 mg).

$^1$HNMR (400 MHz, DMSO-d6): ☐ 7.24 (s, 1H), 7.12 (s, 1H), 6.93 (t, 1H, J=7.6 Hz), 6.6 (s, 1H), 6.55 (d, 1H, J=7.6 Hz), 6.44 (dd, 1H, J=1.2 and 5.2 Hz), 5.78 (d, 1H, J=4 Hz), 5.01 (bs, 1H), 4.64 (d, 1H, J=3.2 Hz). GCMS: 166 [M+].

Intermediate-xiv

Synthesis of
3-Amino-N-(tetrahydro-2H-pyran-4-yl)benzamide

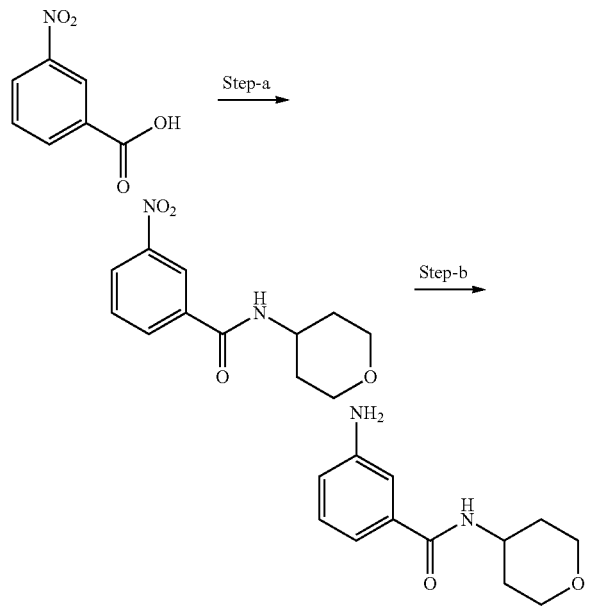

Step-a: Synthesis of
3-Nitro-N-(tetrahydro-2H-pyran-4-yl)benzamide

Under nitrogen atmosphere, 3-nitrobenzoic acid (1.00 g, 5.98 mmol) was taken in THF (20 ml) and the mixture was cooled to 0° C. followed by addition of N-methylmorpholine (0.855 ml, 7.78 mmol) and ethyl chloroformate (6.58 mmol). The reaction mixture was stirred for 30 min at 0° C. and tetrahydro-2H-pyran-4-amine (0.6 ml, 5.98 mmol) was added and the reaction mixture was stirred at room temperature for 30 min. The reaction mixture was concentrated under vacuum and the residue was taken in ethyl acetate (20 ml), washed with water and brine, dried over sodium sulfate and concentrated under vacuum to afford the solid product (1.2 gm).

Step-b: Synthesis of
3-Amino-N-(tetrahydro-2H-pyran-4-yl)benzamide

To a mixture of 3-Nitro-N-(tetrahydro-2H-pyran-4-yl) benzamide (360 mg, 1.439 mmol), ammonium formate (272 mg, 4.32 mmol) in methanol (20 ml) at 0° C., was added Pd/C (10%, 0.04 g) and the reaction mixture was stirred at 60° C. for 1 hrs. The reaction mixture was cooled to room temperature and filtered through celite, the filtrate was concentrated under vacuum. The residue was taken in ethyl acetate and the organic layer was washed with water and brine, dried over sodium sulfate and concentrated under vacuum to afford the title compound (300 mg).

$^1$HNMR (400 MHz, DMSO-d$_6$): ☐ 7.21 (t, 1H, J=8 Hz), 7.14-7.13 (m, 1H), 7.05 (d, 1H, J=7.6 Hz), 6.82-6.80 (m, 1H), 5.94 (d, 1H, J=6 Hz), 4.22-4.18 (m, 1H), 4.03-4.00 (m, 2H), 3.98-3.80 (bs, 2H), 3.55 (t, 2H, J=9.6 Hz), 2.03-2.00 (m, 2H), 1.55-1.44 (m, 2H).

Intermediate-xv: Synthesis of 2-(3-Aminophenyl)-1-(azetidin-1-yl)ethanone

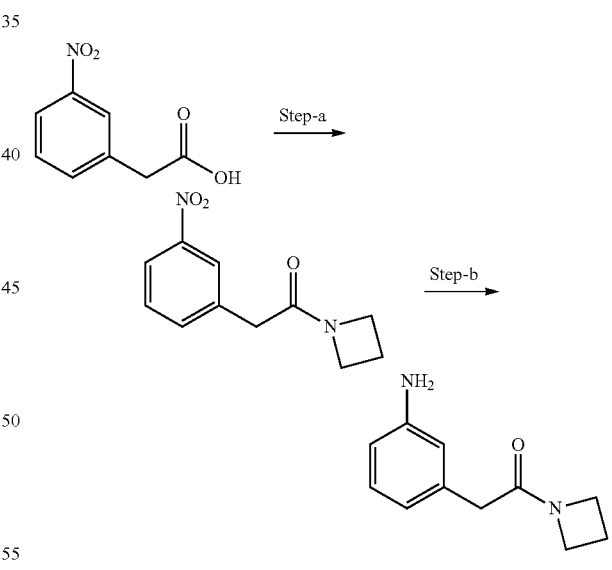

Step-a: Synthesis of 1-(Azetidin-1-yl)-2-(3-nitrophenyl)ethanone

THF (30 mL) was added to a mixture of 2-(3-Nitrophenyl)acetic acid (1 g, 5.52 mmol) and CDI (1.34 g, 8.28 mmol), the mixture was stirred for 2 hrs at 0° C. followed by addition of triethylamine (2.308 ml, 16.56 mmol) and azetidine hydrochloride (1.0-3 g, 11.04 mmol). The reaction mixture was stirred for 12 hrs at room temperature and then concentrated under vacuum. The crude residue was purified by column chromatography using 0-50% ethyl acetate in hexanes as eluent to afford the title product (0.53 g).

Step-b: Synthesis of 2-(3-Aminophenyl)-1-(azetidin-1-yl)ethanone 1-(Azetidin-1-yl)-2-(3-nitrophenyl)ethanone (0.5 g, 2.27 mmol) was taken in methanol (20 ml) and at 0° C., Pd—C (10%, 0.05 g) was added. The reaction mixture was stirred under hydrogen atmosphere at room temperature for 5 hrs. The reaction mixture was filtered through celite and the filtrate was concentrated under vacuum to afford the title product (0.34 gm).

Intermediate-xvi: Synthesis of 2-(3-Aminophenyl)-N-(oxetan-3-yl)acetamide

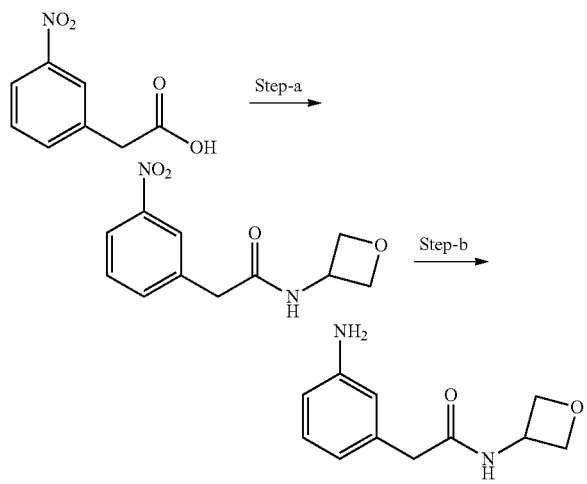

Step-a: Synthesis of 2-(3-Nitrophenyl)-N-(oxetan-3-yl)acetamide

THF (30 mL) was added to a mixture of 2-(3-Nitrophenyl)acetic acid (0.8 g, 4.42 mmol), CDI (1.07 g, 8.28 mmol), the mixture was stirred for 2 hrs at 0° C. followed by addition of triethylamine (1.8 ml, 13.25 mmol) and oxetan-3-amine (0.484 g, 6.62 mmol). The reaction mixture was stirred for 12 hrs at room temperature and then concentrated under vacuum. The crude residue was purified by column chromatography using 0-50% ethyl acetate in hexanes as eluent to afford the title product (0.5 g).

Step-b: Synthesis of 2-(3-Aminophenyl)-N-(oxetan-3-yl)acetamide 2-(3-Nitrophenyl)-N-(oxetan-3-yl)acetamide (0.5 g, 2.11 mmol) was taken in methanol (20 ml) and at 0° C., 10% Pd—C (0.5 g) was added. The reaction mixture was stirred under hydrogen atmosphere at room temperature for 5 hrs. The reaction mixture was filtered through celite and the filtrate was concentrated under vacuum to afford the title product (0.42 gm).

Intermediate-xvii: Synthesis of 2-(3-aminophenyl)-1-(3-hydroxyazetidin-1-yl)ethanone

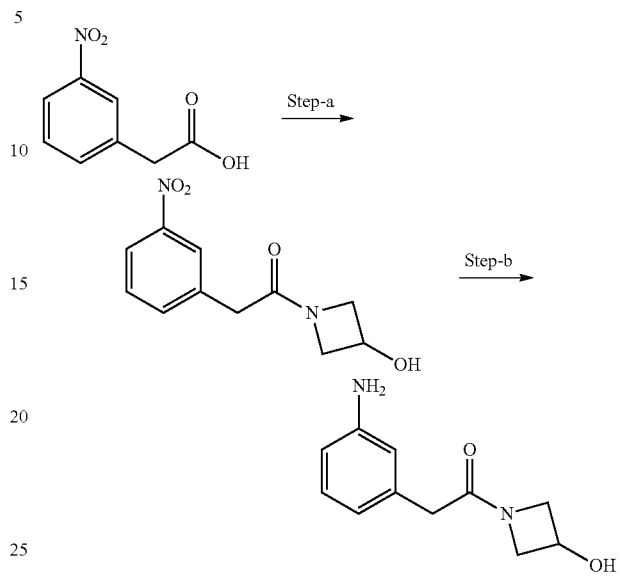

Step-a: Synthesis of 1-(3-Hydroxyazetidin-1-yl)-2-(3-nitrophenyl)ethanone

THF (30 mL) was added to a mixture of 2-(3-Nitrophenyl)acetic acid (0.5 g, 2.76 mmol), CDI (0.671 g, 4.14 mmol), the mixture was stirred for 2 hrs at 0° C. followed by addition of triethylamine (1.2154 ml, 8.28 mmol) and azetidin-3-ol hydrochloride (0.756 g, 6.90 mmol). The reaction mixture was stirred for 12 hrs at room temperature and then concentrated under vacuum. The crude residue was purified by column chromatography using 0-50% ethyl acetate in hexanes as eluent to afford the title product (0.51 g).

Step-b: Synthesis of 2-(3-aminophenyl)-1-(3-hydroxyazetidin-1-yl)ethanone 1-(3-hydroxyazetidin-1-yl)-2-(3-nitrophenyl)ethanone (0.5 g, 2.117 mmol) was taken in methanol (20 ml) and at 0° C., Pd—C (10%, 0.5 g) was added. The reaction mixture was stirred under hydrogen atmosphere at room temperature for 5 hrs. The reaction mixture was filtered through celite and the filtrate was concentrated under vacuum to afford the title product (0.42 gm).

Intermediate xviii: Synthesis of 3-(3-aminophenyl)-N-cyclopropylpropanamide

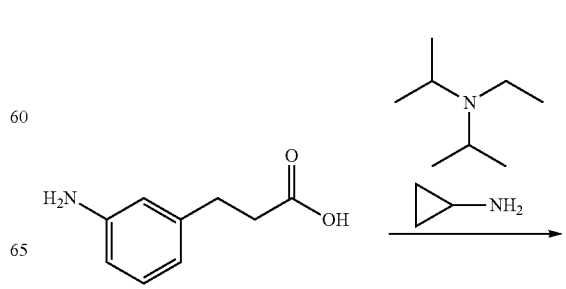

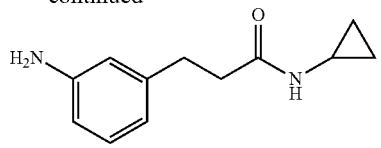

To a stirred solution of 3-(3-aminophenyl)propanoic acid (1 g, 6.05 mmol) in 10 ml DMF, N-ethyl-N-isopropylpropan-2-amine (1.174 g, 9.08 mmol), cyclopropanamine (0.415 g, 7.26 mmol) were added, resulting clear solution was stirred at room temperature, HATU (3.45 g, 9.08 mmol) was added and the resulting mixture was stirred for 24 h at room temperature. Reaction Mixture was diluted with cold water and extraction with Ethyl Acetate (3×30 ml). The Combined organic layer was dried over sodium sulphate and evaporated under reduced pressure to give the crude compound, the crude compound was purified by column chromatography to afford the pure title compound (500 mg).

$^1$H NMR (400 MHz, DMSO-$d_6$) δ (ppm): 7.89-7.85 (m, 1H), 6.92-6.83 (m, 1H), 6.38-6.30 (m, 3H), 4.94 (brs, 2H), 2.68-2.63 (m, 1H), 2.57-2.51 (m, 2H), 2.25-2.21 (m, 2H), 0.59-0.55 (m, 2H), 0.35-0.32 (m, 2H)

ESI-MS (m/z): 205.0 [M+1]

Intermediate xix: Synthesis of 3-Amino-N-(1-carbamoylcyclopropyl)benzamide

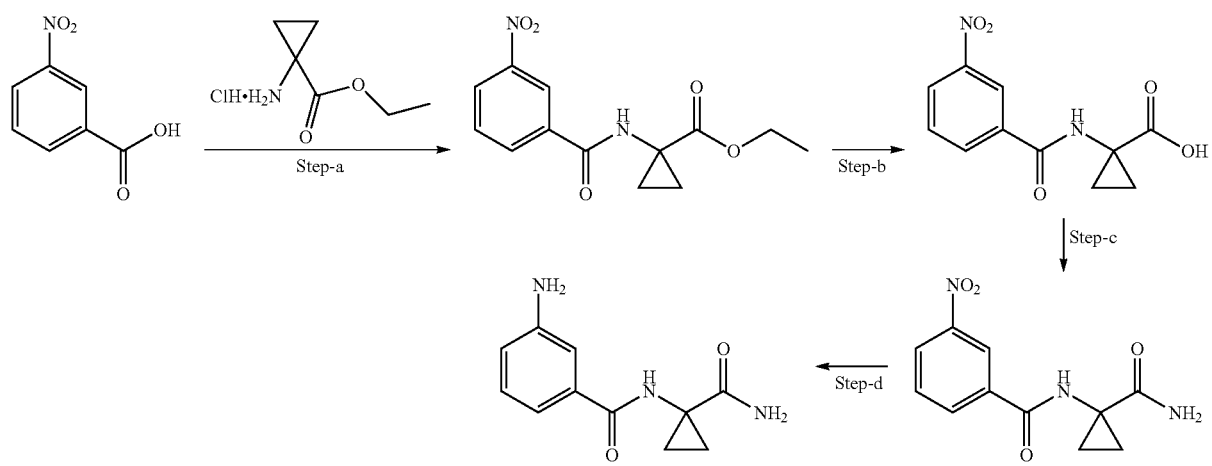

Step-a: Synthesis of Ethyl 1-(3-nitrobenzamido)cyclopropanecarboxylate

To the suspension of 3-nitrobenzoic acid (1 g, 5.98 mmol) in pyridine (10 ml) ethyl 1-aminocyclopropanecarboxylate hydrochloride (1.090 g, 6.58 mmol) was added followed by EDC.HCl (1.721 g, 8.98 mmol) under nitrogen. Reaction mixture was stirred at room temperature for 3 hrs. Reaction mixture was diluted with cold water (100 ml) and extracted with ethyl acetate (2×25 ml). Separated organic layer was washed with brine and water, dried over sodium sulfate and concentrated under vacuum till dryness to obtain product (1.26 g, 76%).

$^1$H NMR (400 MHz, CDCl$_3$) δ (ppm): 8.59 (bs, 1H), 8.41-8.38 (m, 1H), 8.20-8.18 (m, 1H), 7.68 (t, 1H, J=8 Hz), 6.82 (bs, 1H), 4.19 (q, 2H, J=7.2 Hz), 1.70-1.34 (m, 2H), 1.37-1.33 (m, 2H), 1.26 (t, 3H, J=7.2 Hz).

ESI-MS (m/z): 279.58 (M+1)

Step-b: Synthesis of 1-(3-Nitrobenzamido)cyclopropanecarboxylic acid

To the solution of ethyl 1-(3-nitrobenzamido)cyclopropanecarboxylate (0.5 g, 1.797 mmol) in ethanol 10 ml, sodium hydroxide (aq) (5 ml, 25.00 mmol) was added and stirred at room temperature for 10 hr. Reaction mixture was diluted with water (20 ml), and acidified by adding 5N HCl. Obtained white precipitates were filtered. The residue was dried by azetrope with toluene (0.38 g, 85%).

$^1$HNMR (400 MHz, CDCl$_3$) δ (ppm): 12.51 (s, 1H), 9.38 (s, 1H), 8.69 (t, 1H, J=1.2 Hz), 8.41-8.39 (dd, 1H, J=1.2 and 8 Hz), 8.29 (d, 1H, J=7.6 Hz), 7.79 (t, 1H, J=8 Hz), 1.64-1.13 (m, 2H), 1.45-1.42 (m, 2H).

Step-c: Synthesis of N-(1-carbamoylcyclopropyl)-3-nitrobenzamide

To the suspension of 1-(3-nitrobenzamido)cyclopropanecarboxylic acid (0.38 g, 1.519 mmol) in dichloromethane (5 ml), oxalyl chloride (0.199 ml, 2.278 mmol) was added followed by DMF (0.024 ml, 0.304 mmol). Reaction mixture was stirred at room temperature for 3 hr. After complete dissolution of the compound, cold aqueous ammonia (5 ml) was added under cooling. Allowed and stirred the content at room temperature for 1 hr. concentrated the reaction mixture to remove dichloromethane and the obtained slurry was filtered to obtain titled compound (0.28 g, 74%).

Step-d: Synthesis of 3-Amino-N-(1-carbamoylcyclopropyl)benzamide

To the suspension of N-(1-carbamoylcyclopropyl)-3-nitrobenzamide (0.28 g, 1.123 mmol) in methanol (5 ml), Pd—C (0.05 g) was added under nitrogen and stirred the reaction mixture under hydrogen atmosphere at room temperature. After 2 hr, reaction mixture was filtered and concentrated under vacuum to afford solid compound (0.2 g, 81%).

ESI-MS (m/z): 220.83 (M+1)

Intermediate xx: Synthesis of 3-Amino-N-(1-(hydroxymethyl)cyclopropyl) benzamide

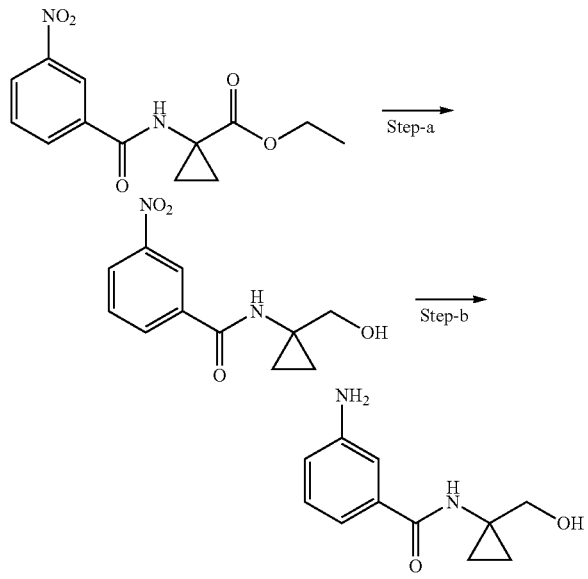

Step-a: Synthesis of N-(1-(Hydroxymethyl)cyclopropyl)-3-nitrobenzamide

To the suspension of ethyl 1-(3-nitrobenzamido)cyclopropanecarboxylate (0.400 g, 1.438 mmol) in tetrahydrofuran 10 ml, LiBH4 (0.063 g, 2.88 mmol) was added and heated the content at 45° C. for 15 hr. Reaction mixture was quenched with saturated ammonium chloride and extracted with ethyl acetate (2×10 ml). Organic layer was dried over sodium sulfate and concentrated under vacuum which was further purified by column chromatography eluting ethyl acetate (0-70%) in hexane (0.05 g, 14%).

$^1$H NMR (400 MHz, DMSO-$d_6$) δ (ppm): 9.08 (s, 1H), 8.69 (t, 1H, J=1.6 Hz), 8.38-8.35 (m, 1H), 8.30-8.27 (m, 1H), 7.75 (t, 1H, J=7.6 Hz), 4.80 (t, 1H, J=6 Hz), 3.53 (d, 2H, J=5.6 Hz), 0.77-0.72 (m, 4H).

ESI-MS (m/z): 237 (M+1)

Step-b: Synthesis of 3-Amino-N-(1-(hydroxymethyl)cyclopropyl)benzamide

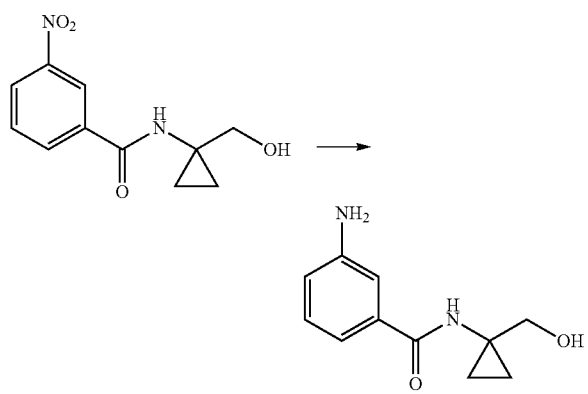

To the solution of N-(1-(hydroxymethyl)cyclopropyl)-3-nitrobenzamide (0.135 g, 0.571 mmol) in methanol Pd—C (50% wet) (0.015 g) was added and stirred at room temperature under hydrogen for 2 hr. Reaction mixture was filtered through celite and concentrated to afford product (01 g, 85%).

$^1$H NMR (400 MHz, DMSO-$d_6$) δ (ppm): 8.39 (bs, 1H), 7.05-7.00 (m, 2H), 6.95-6.93 (m, 1H), 6.67-6.64 (m, 1H), 5.18 (s, 2H), 4.73 (t, 1H, J=6 Hz), 3.50 (d, 2H, J=5.6 Hz), 0.75-0.64 (m, 4H). GCMS: 206.98 (M+)

Intermediate xxi: Synthesis of (3-aminophenyl)(morpholino)methanone

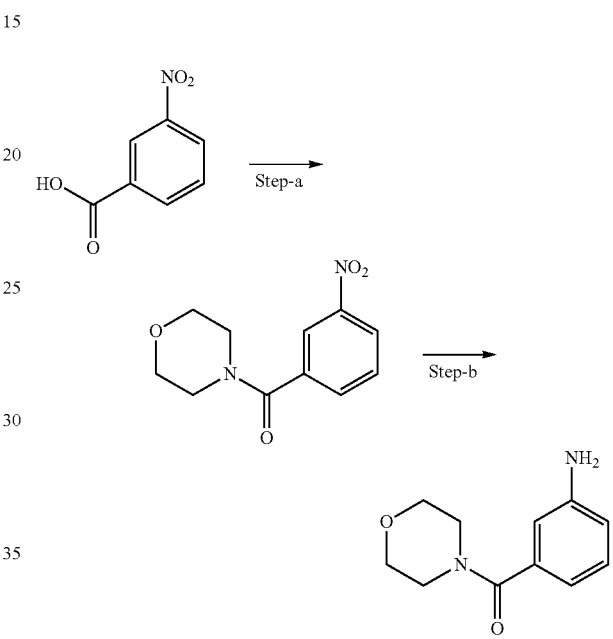

Step-a Preparation of morpholino(3-nitrophenyl)methanone

To stirred solution of 3-nitrobenzoic acid (5 g, 29.9 mmol) in DCM: DMF (30 ml, 29:1) was added oxalyl chloride (3.14 ml, 35.9 mmol) dropwise at RT. Resulting reaction mixture was stirred for 1 h. The mixture was concentrated and the residue was dissolved in DCM (25 ml), the reaction mixture was cooled to 0° C. and triethylamine (6.26 ml, 44.9 mmol) and morpholine (3.13 ml, 35.9 mmol) were added and the reaction mixture was stirred for 1 h. The reaction mixture was concentrated under vacuum and the residue was diluted with cold water, the solid separated out was filtered and washed with n-hexanes and dried under vacuum to give the product (4.9 g).

$^1$HNMR (400 MHz, DMSO), δ (ppm): 8.32-8.29 (m, 1H), 8.23-8.22 (m, 1H), 7.89-7.86 (m, 1H), 7.75 (t, J=8.00 Hz, 1H), 3.65-3.55 (m, 8H). GCMS-236.22 (M+).

Step-b Preparation of (3-aminophenyl)(morpholino)methanone

To a solution of morpholino(3-nitrophenyl)methanone (2 g, 8.47 mmol) in Ethyl acetate (40 ml) was added tin(II) chloride dehydrate (7.64 g, 33.9 mmol). Resulting reaction mixture was stirred at RT for 17 h. The reaction mixture was nutralized with NaOH (2N), the mixture was filtered and the filtrate was extracted with Ethyl acetate (250 ml×2). The combined organic layer was washed with brine, dried over sodium sulphate and concentrated under vacuum to give the title product (1.4 g).
GCMS-206.24

Intermediate xxii: Synthesis of 2-(3-aminophenoxy)-2-methylpropanamide

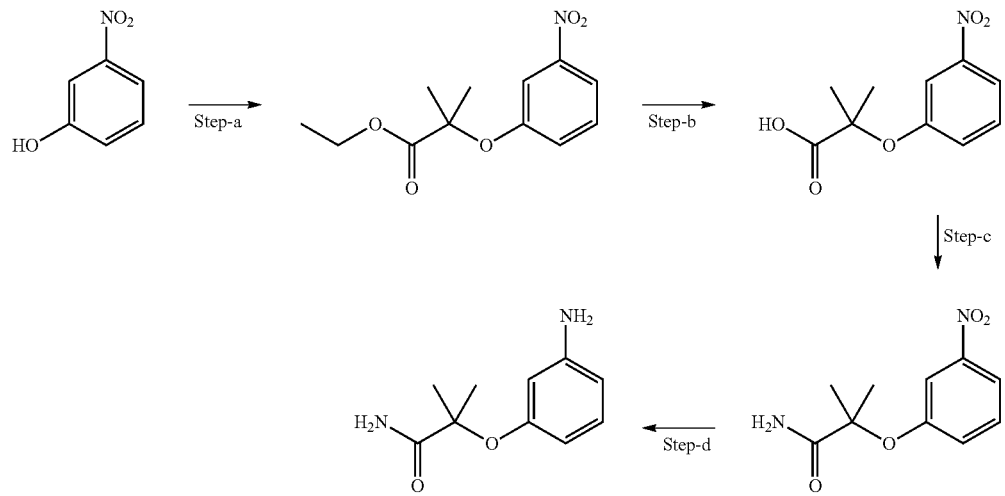

Step-a: Preparation of ethyl 2-methyl-2-(3-nitrophenoxy)propanoate

To a solution of 3-nitrophenol (7.5 g, 53.9 mmol) and ethyl 2-bromo-2-methylpropanoate (12.62 g, 64.7 mmol) in DMF (25 ml) was added $K_2CO_3$ (14.90 g, 108 mmol). After stirring at rt for 16 hr, the reaction mixture was concentrated under vacuum. The residue was diluted with water and extracted with ethyl acetate (3×30 ml), the combined organic layer was washed with NaOH solution (10%, 75 mL), water (75 mL) and brine, dried over sodium sulphate and concentrated under vacuum to give the title product (6.7 g).
$^1$HNMR (400 MHz, DMSO), δ (ppm): 7.89-7.86 (m, 1H), 7.60-7.54 (m, 2H), 7.30-7.28 (m, 1H), 4.18-4.01 (m, 2H), 1.59 (s, 6H), 1.21-1.14 (m, 3H). GCMS-253.25.

Step-b: Preparation of 2-methyl-2-(3-nitrophenoxy)propanoic acid

The mixture of ethyl 2-methyl-2-(3-nitrophenoxy)propanoate (3.5 g, 13.82 mmol) and $LiOH.H_2O$ (2.320 g, 55.3 mmol) in Tetrahydrofuran (7 ml), MeOH (7 ml) and Water (7 ml) was stirred at room temperature for 4 hr. The reaction mixture was concentrated under vacuum and the residue was neutralised with 1N HCl, solid separated was filtered and treated with pentane to afford the title product (2.68 g).
$^1$HNMR (400 MHz, DMSO), δ (ppm): 13.40 (bs, 1H), 7.86 (dd, J=1.6 & 8.0 Hz, 1H), 7.60-7.56 (m, 2H), 7.31 (dd, J=2 & 8.4 Hz, 1H), 1.57 (s, 6H). GCMS-225.19 (M+)

Step-c: Preparation of 2-methyl-2-(3-nitrophenoxy)propanamide

The mixture of 2-methyl-2-(3-nitrophenoxy)propanoic acid (1 g, 4.44 mmol) and CDI (1.080 g, 6.66 mmol) in Tetrahydrofuran (10 ml) was stirred at room temperature for 3 hr, ammonia (2.0 M in Methanol, 10 ml) was added, and the mixture was stirred at room temperature for 1 hr. The reaction mixture was concentrated under vacuum and the residue was treated with pentane to afford the title product (0.914 g).
$^1$HNMR (400 MHz, DMSO), δ (ppm): 7.88-7.85 (m, 1H), 7.70-7.56 (m, 2H), 7.40 (bs, 1H), 7.36-7.32 (m, 1H), 7.01 (bs, 1H), 1.49 (s, 6H). GCMS-224.21 (M+).

Step-d: Preparation of 2-(3-aminophenoxy)-2-methylpropanamide

To a stirred solution of 2-methyl-2-(3-nitrophenoxy)propanamide (0.910 g, 4.06 mmol) in MeOH (15 ml) was added Pd—C (10%, 0.346 g) and triethylsilane (6.48 ml, 40.6 mmol) (slow addition) at room temperature. The reaction mixture was stirred at same temperature for 30 min. and filtered through celite, washed with methanol (50 ml). The Filtrate was concentrated under vacuum to get the crude compound. The crude compound was purified by flash chromatography to give the title product (0.516 g).
$^1$HNMR (400 MHz, DMSO), δ (ppm): 7.39 (bs, 1H), 7.19 (bs, 1H), 6.86 (t, J=8.00 Hz, 1H), 6.21-6.18 (m, 1H), 6.14-6.13 (m, 1H), 6.06-6.04 (m, 1H), 5.03 (s, 2H), 1.38 (s, 6H). GCMS-194.23 (M+).

Intermediate xxiii: Synthesis of (3-aminophenyl)(4-methylpiperazin-1-yl)methanone

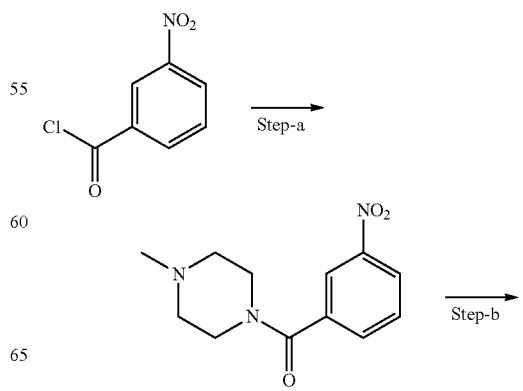

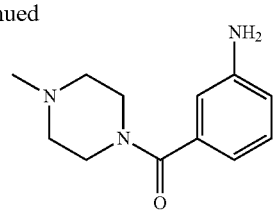

Step-a Preparation of (4-methylpiperazin-1-yl)(3-nitrophenyl)methanone

To a solution of 3-nitrobenzoyl chloride (4.5 g, 24.25 mmol) in THF (30 ml) was added 1-methylpiperazine (8.50 g, 85 mmol). The reaction was stirred for 20 min at room temperature. The reaction mixture was diluted with 50 mL water and extracted with ethyl acetate (2×100 mL). The combined organic layer was washed with brine (50 mL). The brine was back extracted with ethyl acetate (2×50 mL) and all the organic layers were combined, dried over magnesium sulphate, filtered, and concentrated under vacuum give the title product (5.2 g).

$^1$HNMR (400 MHz, DMSO), δ (ppm): 8.32-8.29 (m, 1H), 8.19-8.18 (m, 1H), 7.86-7.84 (m, 1H), 7.77-7.72 (m, 1H), 3.64 (bs, 2H), 3.30 (bs, 2H), 2.38-2.27 (m, 2H), 2.19 (s, 3H). GCMS-249.26 (M+).

Step-b Preparation of (3-aminophenyl)(4-methylpiperazin-1-yl)methanone

To a stirred solution of (4-methylpiperazin-1-yl)(3-nitrophenyl)methanone (5.5 g, 22.06 mmol) in MeOH (50 ml) was added Pd—C (10%, 0.470 g) followed by triethylsilane (14.10 ml, 88 mmol) (slow addition) at RT. The reaction mixture was stirred at same temperature for 25 min and filtered through celite, washed with methanol (50 ml). The Filtrate was concentrated under vacuum to get the title product (4.11 g).

$^1$HNMR (400 MHz, DMSO), δ (ppm): 7.05 (t, J=8.0 Hz, 1H) 6.61-6.58 (m, 1H), 6.53-6.52 (m, 1H), 6.45-6.43 (m, 1H), 5.25 (s, 2H), 3.55-3.32 (m, 4H), 2.50-2.28 (m, 4H), 2.18 (s, 3H). GCMS-219.28 (M+).

The following intermediates given in table 1 were prepared according to the preparation procedures depicted in the following references accordingly.

TABLE-1

| No. | Aniline | Reference |
|---|---|---|
| xxiv | ![structure] | Bulletin of the Korean Chemical Society, 2011 vol. 32, #12 p. 4444-4446 |
| xxv | ![structure] | WO2006/129100 A1, |
| xxvi | ![structure] | Bioorganic and Medicinal Chemistry Letters, 2010, vol. 20, #3 p. 1169-1172 |
| xxvii | ![structure] | Journal of Medicinal Chemistry, 1996, vol. 39, #26 p. 5236-5245 |
| xxviii | ![structure] | Bioorganic and Medicinal Chemistry, 2008, vol. 16, #3 p. 1206-1217 |
| xxix | ![structure] | US2009/82379 A1 |

Intermediate xxx: Synthesis of 1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl 4-methylbenzenesulfonate

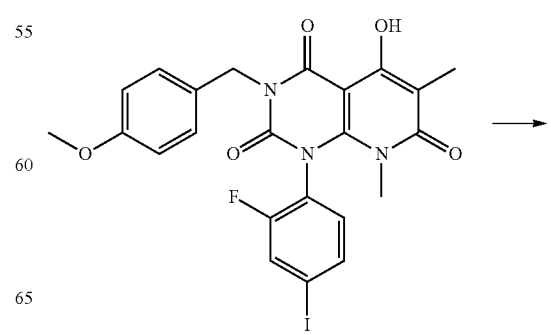

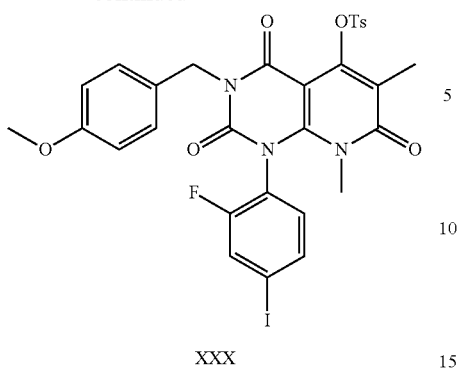

XXX

Under nitrogen atmosphere, to a solution of 1-(2-fluoro-4-iodophenyl)-5-hydroxy-3-(4-methoxybenzyl)-6,8-dimethylpyrido[2,3-d]pyrimidine-2,4,7(1H,3H,8H)-trione (41 g, 72.8 mmol) (Prepared as per reference WO2005121142) in acetonitrile (300 ml), triethylamine (30.4 ml, 218 mmol) and trimethylamine hydrochloride (3.48 g, 36.4 mmol) were added slowly followed by addition of p-toluensulfonylchloride (27.8 g, 146 mmol) in acetonitrile (300 ml) at 0° C., and the mixture was stirred under ice cooling for 1 hr, and then at room temperature for 24 h. To the reaction mixture was added methanol (220 ml), and the mixture was stirred at room temperature for 1 h. The precipitated crystals were collected by filtration, dried under vacuum to afford the titled compound (40.5 g, 78%)

$^1$H NMR (400 MHz, DMSO-d$_6$) δ: 7.95 (dd, J=1.6 and 9.6 Hz, 1H), 7.84 (d, J=8.4 Hz, 2H), 7.72 (dd, J=1.2 and 8.4 Hz, 2H), 7.46 (d, J=8.4 Hz, 2H), 7.35 (t, J=8.4 Hz, 1H), 7.23 (d, J=8.8 Hz, 2H), 6.86 (d, J=8.8 Hz, 2H), 4.92 (d, J=16 Hz, 1H), 4.77 (d, J=16 Hz, 1H), 3.71 (s, 3H), 2.76 (s, 3H), 2.42 (s, 3H), 1.53 (s, 3H).

MS (ESI): 717.9.

Intermediate xxxi: Synthesis of
1-(3-aminophenyl)cyclopropanecarboxamide
Scheme

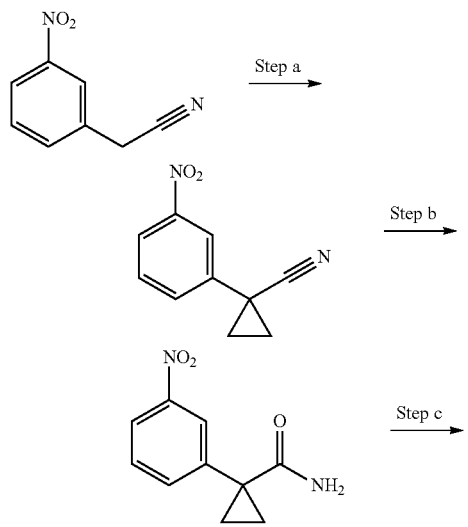

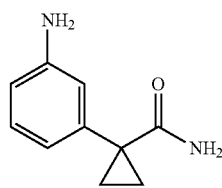

Step a: Synthesis of
1-(3-nitrophenyl)cyclopropanecarbonitrile

A solution of 2-(3-nitrophenyl)acetonitrile (2.5 g, 15.42 mmol) and 1,2-dibromoethane (1.329 ml, 15.42 mmol) in DMSO/Et$_2$O (1:1, 10 ml) was added dropwise to a suspension of NaH (1.233 g, 30.8 mmol) in DMSO (Volume: 10 ml, Ratio: 1.000), keeping the temperature at 0° C. Resulting mixture was stirred at ambient temperature for 24 h under N2 atm. The reaction mixture was quenched by addition of IPA (2 ml) and water; partitioned between water (300 ml) and EtOAc (300 ml). The aq. phase was re-extracted with EtOAc (300 ml). Combined organic layers were dried over sodium sulphate and concentrated in vacuo. The residue was purified by flash chromatography to afford 1-(3-nitrophenyl)cyclopropanecarbonitrile (1.799 g, 9.56 mmol).

$^1$H NMR (400 MHz, DMSO-d$_6$) δ 8.19-8.16 (m, 1H), 8.07-8.06 (m, 1H), 7.79-7.75 (m, 1H), 7.58 (t, J=8.4 Hz, 1H), 1.91-1.84 (m, 2H), 1.56-1.48 (m, 2H).

GCMS: 188.01 [M+]

Step b: Synthesis of
1-(3-nitrophenyl)cyclopropanecarboxamide

To a solution of 1-(3-nitrophenyl)cyclopropanecarbonitrile (1.6 g, 8.50 mmol) in 2-Propanol (50 ml) was added triethylbenzylammonium chloride (0.058 g, 0.255 mmol) and 25% aq KOH solution (5 ml). Resulting solution was stirred for 5 min. and H$_2$O$_2$(10 ml, 98 mmol, ca. 30% solution in water) was added. Reaction mixture was heated at 50° C. for 4 h. Solvent was evaporated in vacuo and residue was suspended in water (200 ml). Precipitate was filtered and dried to obtain 1-(3-nitrophenyl)cyclopropane carboxamide (1.104 g, 5.36 mmol, 63% yield).

$^1$H NMR (400 MHz, DMSO-d$_6$) δ 8.31-8.13 (m, 2H), 7.80-7.78 (m, 1H), 7.64-7.60 (m, 1H), 7.11 (s, 1H), 6.58 (s, 1H), 1.42-1.35 (m, 2H), 1.08-1.03 (m, 2H).

GCMS: 206.04 [M+]

Step c: Synthesis of
1-(3-aminophenyl)cyclopropanecarboxamide

Triethylsilane (7.75 ml, 48.5 mmol) was added dropwise to a suspension of 1-(3-nitrophenyl)cyclopropanecarboxamide (1 g, 4.85 mmol) and Pd/C (10%, 250 mg) in MeOH (20 ml). Resulting suspension was stirred at RT for 20 min. and filtered through celite. The filtrate was evaporated and triturated in hexane to obtain the crystals which were collected by filtration to afford the title compound (0.68 g).

$^1$H NMR (400 MHz, DMSO-d$_6$) δ 7.04 (brs, 1H), 6.98 (t, J=8.0 Hz, 1H), 6.60-6.56 (m, 1H), 6.49-6.45 (m, 2H), 5.90 (brs, 1H), 5.09 (s, 2H), 1.26-1.23 (m, 2H), 0.88-0.85 (m, 2H).

GCMS: 176.07 [M+]

Example-1: Synthesis of 3-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide (Compound 1)

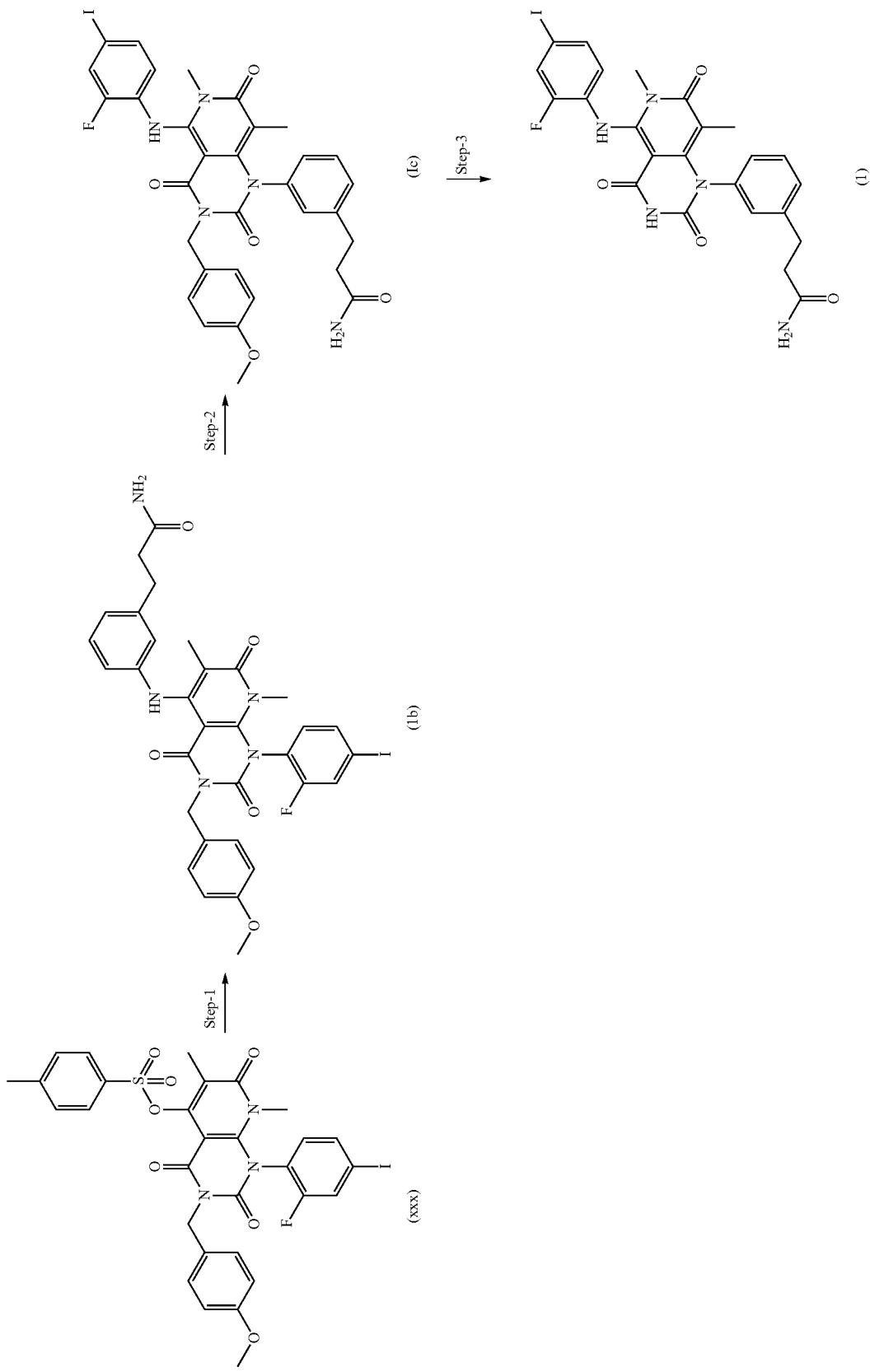

Step-1: Synthesis of 3-(3-((1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl)amino)phenyl) propanamide (1b)

To a stirred solution of 1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl 4-methylbenzene sulfonate (xxx) (2 gm, 2.79 mmol) in DMA (5 ml) was added 2,6-lutidine (0.597 g, 5.57 mmol) and 3-(3-aminophenyl)propanamide (intermediate xxvi) (0.915 gm, 5.57 mmole). The reaction mixture was heated at 130° C. for 16 h. The reaction mixture was cooled to room temperature and added water until a solid precipitate was obtained. The solid was filtered, washed with water and small amount of MeOH. The solid was purified by silica gel column chromatography, eluting with DCM: Methanol (9:1), to yield the titled compound (1b) (1.7 g) [m/z=710.20 (M+1)].
$^1$HNMR (400 MHz, DMSO-$d_6$) δ 10.2 (s, 1H), 7.97 (dd, 2.0 and 9.6 Hz, 1H), 7.75 (dd, 1.2 and 8.4 Hz, 1H), 7.37 (t, J=8 Hz, 1H), 7.28 (d, J=8.8 Hz, 3H), 7.20 (t, J=8 Hz, 1H), 6.86 (m, 3H), 6.76 (m, 3H), 5.00 (m, 2H), 3.70 (s, 3H), 2.75 (m, 5H), 2.33 (t, J=7.2 Hz, 2H), 1.50 (s, 3H).

Step-2: Synthesis of 3-(3-(5-((2-fluoro-4-iodophenyl)amino)-3-(4-methoxybenzyl)-6,8-dimethyl-2,4,7-trioxo-3,4,6,7-tetrahydropyrido[4,3-d]pyrimidin-1(2H)-yl)phenyl) propanamide (1c)

To a solution of 3-(3-((1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl)amino)phenyl) propanamide (1b) (1.7 gm, 2.396 mmol) in THF (8 ml) was added sodium methoxide (30% solution in MeOH) (0.431 mg, 2.396 mmol) at 0° C. The reaction mixture was stirred at room temperature for 2 hr and quenched by addition of 2N HCl solution. The resulting mixture was concentrated under vacuum and residue was re-crystallized in IPA, methanol and water to yield the titled compound (Ic) (1.5 g, 88%) [m/z=710.20 (M+1)].
$^1$H NMR (400 MHz, DMSO-$d_6$) δ 11.11 (s, 1H), 7.78 (dd, J=2 Hz and 10.4 Hz, 1H), 7.52 (dd, J=1.2 Hz and 9.6 Hz, 1H), 7.35 (t, J=8 Hz, 2H), 7.22 (m, 5H), 6.98 (t, J=8.8 Hz, 1H), 6.84 (d, J=8.8 Hz, 2H), 6.79 (s, 1H), 4.96 (s, 2H), 3.67 (s, 3H), 3.14 (s, 3H), 2.78 (m, 2H), 2.42 (m, 2H), 1.22 (s, 3H).

Step-3: Synthesis of 3-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide (1)

Aluminium chloride (2.82 g, 21.14 mmol) was added in small portions to a solution of 3-(3-(5-((2-fluoro-4-iodophenyl)amino)-3-(4-methoxybenzyl)-6,8-dimethyl-2,4,7-trioxo-3,4,6,7-tetrahydropyrido[4,3-d]pyrimidin-1(2H)-yl)phenyl)propanamide (1c) (1.500 g, 2.114 mmol) in anisole (15 ml). The resulting reaction mixture was stirred at room temperature for 24 h, then quenched by addition of MeOH (15 ml) and 2N HCl (0.5 ml). The resulting mixture was concentrated under vacuum and the residue thus obtained was purified by silica gel column chromatography to yield the titled compound (1) (0.450 g, 44%) [m/z=590.1 (M+1)].
$^1$HNMR (400 MHz, DMSO-$d_6$) δ 11.57 (s, 1H), 11.22 (s, 1H), 7.78 (dd, J=2&10.4 Hz, 1H), 7.55 (d, J=8.4 Hz, 1H), 7.35 (t, J=7.6 Hz, 1H), 7.31 (brs, 1H), 7.26 (brs, 1H), 7.24-7.21 (m, 2H), 6.94 (t, J=8.4 Hz, 1H), 6.78 (brs, 1H), 3.06 (s, 3H), 2.82 (t, J=7.6 Hz, 2H), 2.36 (t, J=6.4 Hz, 2H), 1.19 (s, 3H).

The compounds given below in Table 2: were prepared by procedure similar to the one described above in Example 1 with the above stated intermediates with appropriate variations in reactants, reaction conditions and quantities of reagents.

TABLE 2

| Cmpd. No. | Intermed. No. | Name | Analytical data |
|---|---|---|---|
| 2 | xxiv | N-cyclopropyl-3-(5-((2-fluoro-4-iodophenyl)amino)-6,8-dimethyl-2,4,7-trioxo-3,4,6,7-tetrahydropyrido[4,3-d]pyrimidin-1(2H)-yl)benzamide | $^1$H NMR (400 MHz, DMSO-$d_6$) δ 11.62 (s, 1H), 11.21 (s, 1H), 8.52 (d, 1H, J = 4 Hz), 7.86-7.83 (m, 1H), 7.80-7.77 (m, 2H), 7.58-7.51 (m, 3H), 6.96 (t, 1H, J = 8.8 Hz), 3.06 (s, 3H), 2.86-2.80 (m, 1H), 1.16 (s, 3H), 0.70-0.68 (m, 2H), 0.58-0.57 (m, 2H) MS: m/z 602.1 (M + 1). |
| 3 | i | 1-(3-(azetidine-1-carbonyl)phenyl)-5-((2-fluoro-4-iodophenyl)amino)-6,8-dimethyl pyrido[4,3-d]pyrimidine-2,4,7(1H,3H,6H)-trione | $^1$H NMR (400 MHz, DMSO-$d_6$), δ 11.59 (s, 1H), 11.18 (s, 1H), 7.79 (dd, J = 1.6 and 10.0 Hz, 1H), 7.62-7.59 (m, 2H), 7.56-7.52 (m, 3H), 6.96 (t, 1H, J = 8.8 Hz), 4.28-4.26 (m, 2H), 4.06-4.02 (m, 2H), 3.06 (s, 3H), 2.27-2.23 (m, 2H), 1.18 (s, 3H). MS: m/z 602.1 (M + 1). |
| 4 | ii | N-cyclopropyl-2-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide | $^1$H NMR (400 MHz, DMSO-$d_6$), δ 11.58 (s, 1H), 11.22 (s, 1H), 8.14 (d, 1H, J = 4 Hz), 7.79 (dd, J = 1.6 and 10.0 Hz, 1H), 7.55-7.53 (m, 1H), 7.39-7.36 (m, 1H), 7.28-7.21 (m, 3H), 6.93 (t, 1H, J = 8.8 Hz), 3.38 (s, 2H), 3.05 (s, 3H), 2.60-2.54 (m, 1H), 1.17 (s, 3H), 0.59-0.57 (m, 2H), 0.36-0.35 (m, 2H). MS: m/z 615.9 (M + 1). |
| 5 | xxv | 2-(3-(5-((2-fluoro-4-iodophenyl)amino)-6,8-dimethyl-2,4,7-trioxo-3,4,6,7-tetrahydro pyrido[4,3-d]pyrimidin-1(2H)- | $^1$H NMR (400 MHz, DMSO-$d_6$), δ 11.57 (s, 1H), 11.21 (s, 1H), 8.07 (brs, 1H), 7.80-7.77 (m, 1H), 7.56-7.53 (m, 2H), 7.40-7.36 (m, 2H), 7.04-7.01 (m, 3H), 6.94 (t, 1H, J = 8 Hz), 4.48 (s, 2H), |

TABLE 2-continued

| Cmpd. No. | Intermed. No. | Name | Analytical data |
|---|---|---|---|
| | | yl)phenoxy)-N-methylacetamide | 3.06 (s, 3H), 2.64 (s, 3H), 1.26 (s, 3H). MS: m/z 606.0 (M + 1). |
| 6 | iii | N-cyclopropyl-2-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenoxy)acetamide | $^1$HNMR (400 MHz, DMSO-d6), δ 11.58 (s, 1H), 11.20 (s, 1H), 8.15 (d, J = 4 Hz, 1H), 7.79 (dd, J = 1.6 and 10.0 Hz, 1H), 7.55 (d, J = 8 Hz, 1H), 7.37 (t, J = 8.8 Hz, 1H), 7.02-6.92 (m, 4H), 4.45 (s, 2H), 3.06 (s, 3H), 2.69-2.65 (m, 1H), 1.23 (s, 3H), 0.64-0.59 (m, 2H), 0.48-0.46 (m, 2H). MS: m/z 632.0 (M + 1). |
| 7 | xxi | 5-((2-fluoro-4-iodophenyl)amino)-6,8-dimethyl-1-(3-(morpholine-4-carbonyl)phenyl) pyrido[4,3-d]pyrimidine-2,4,7(1H,3H,6H)-trione | $^1$HNMR (400 MHz, DMSO-d6), δ 11.61 (s, 1H), 11.18 (s, 1H), 7.80 (dd, J = 2 & 10.4 Hz, 1H), 7.56-7.43 (m, 5H), 6.96 (t, J = 8.8 Hz, 1H), 3.61-3.39 (m, 6H), 3.34-3.32 (m, 2H), 3.06 (s, 3H), 1.21 (s, 3H). MS: m/z 631.9 (M + 1). |
| 8 | v | 1-(3-(1,1-dioxidothiomorpholine-4-carbonyl)phenyl)-5-((2-fluoro-4-iodophenyl)amino)-6,8-dimethylpyrido[4,3-d]pyrimidine-2,4,7(1H,3H,6H)-trione | $^1$HNMR (400 MHz, DMSO-d6), δ 11.64 (s, 1H), 11.18 (s, 1H), 7.79 (dd, J = 2 & 10.4 Hz, 1H), 7.60-7.49 (m, 5H), 6.96 (t, J = 8.8 Hz, 1H), 4.03-4.01 (m, 2H), 3.68 (brs, 2H), 3.29-3.27 (m, 4H), 3.06 (s, 3H), 1.21 (s, 3H). MS: m/z 680.0 (M + 1) |
| 9 | vi | 2-(3-(5-((2-fluoro-4-iodophenyl)amino)-6,8-dimethyl-2,4,7-trioxo-3,4,6,7-tetrahydro pyrido[4,3-d]pyrimidin-1(2H)-yl)phenyl)-2-methylpropanamide | $^1$HNMR (400 MHz, DMSO-d6), δ 11.57 (s, 1H), 11.26 (s, 1H), 7.78 (dd, J = 2 & 10.4 Hz, 1H), 7.55 (dd, J = 1.2 & 8.4 Hz, 1H), 7.43-7.37 (m, 2H), 7.29-7.26 (m, 2H), 6.98-6.91 (m, 3H), 3.06 (s, 3H), 1.43 (s, 6H), 1.16 (s, 3H). MS: m/z 603.9 (M + 1). |
| 10 | viii | 2-(3-(5-((2-fluoro-4-iodophenyl)amino)-6,8-dimethyl-2,4,7-trioxo-3,4,6,7-tetrahydro pyrido[4,3-d]pyrimidin-1(2H)-yl)phenyl)-N,N-dimethylacetamide | $^1$HNMR (400 MHz, DMSO-d6), δ 11.57 (s, 1H). 11.21 (s, 1H), 7.79 (dd, J = 1.6 & 10 Hz, 1H), 7.55 (dd, J = 1.2 & 8.4 Hz, 1H), 7.39 (m, 1H), 7.29-7.19 (m, 3H), 6.94 (t, J = 8.8 Hz, 1H), 3.73 (s, 2H), 3.06 (s, 3H), 2.99 (s, 3H), 2.82 (s, 3H), 1.21 (s, 3H), MS: m/z 604.0 (M + 1). |
| 11 | vii | 2,2-difluoro-2-(3-(5-((2-fluoro-4-iodophenyl)amino)-6,8-dimethyl-2,4,7-trioxo-3,4,7,8-tetrahydropyrido[2,3-d]pyrimidin-1(2H)-yl)phenyl)acetamide | $^1$HNMR (400 MHz, DMSO-d6), δ 11.63 (s, 1H), 11.22 (s, 1H), 8.40 (brs, 1H), 8.07 (brs, 1H), 7.79 (dd, J = 1.6 & 10.4 Hz, 1H), 7.64-7.54 (m, 5H), 6.95 (t, J = 8.8 Hz, 1H), 3.06 (s, 3H), 1.13 (s, 3H). MS: m/z 612.0 (M + 1). |
| 12 | xix | N-(1-Carbamoylcyclopropyl)-3-(5-((2-fluoro-4-iodophenyl)amino)-6,8-dimethyl-2,4,7-trioxo-3,4,6,7-tetrahydropyrido[4,3-d]pyrimidin-1(2H)-yl)benzamide | $^1$HNMR (400 MHz, DMSO-d6), δ 11.62 (s, 1H), 11.21 (s, 1H), 8.98 (s, 1H), 7.93 (d, 1H, J = 7.6 Hz), 7.82-7.77 (m, 2H), 7.59-7.52 (m, 2H), 7.36 (s, 1H), 7.03 (s, 1H), 6.96 (t, 1H, J = 8.8 Hz), 5.76 (s, 1H), 3.06 (s, 3H), 1.21 (s, 3H), 0.98-0.92 (m, 2H), 0.87-0.83 (m, 2H). MS: m/z 645.0 (M + 1). |
| 13 | xiv | 3-(5-((2-Fluoro-4-iodophenyl)amino)-6,8-dimethyl-2,4,7-trioxo-3,4,6,7-tetrahydropyrido [4,3-d]pyrimidin-1(2H)-yl)-N-(tetrahydro-2H-pyran-4-yl)benzamide | $^1$HNMR (400 MHz, DMSO-d6), δ 11.63 (s, 1H), 11.22 (s, 1H), 8.41 (d, 1H, J = 7.6 Hz), 7.91-7.88 (m, 1H), 7.83 (s, 1H), 7.79 (dd, 1H, J = 2 and 8.4 Hz), 7.59-7.53 (m, 3H), 6.96 (t, 1H, J = 8.8 Hz), 4.01-3.96 (m, 1H), 3.88 (dd, 2H, J = 2 and 11.2 Hz), 3.38 (dd, 2H, J = 2 and 12 Hz), 3.06 (s, 3H), 1.78-1.74 (m, 2H), 1.62-1.55 (m, 2H), 1.18 (s, 3H). MS: m/z 646.0 (M + 1). |
| 14 | xiii | 2-(3-(5-((2-Fluoro-4-iodophenyl)amino)-6,8-dimethyl-2,4,7-trioxo-3,4,6,7-tetrahydro pyrido[4,3-d]pyrimidin-1(2H)-yl)phenyl)-2-hydroxyacetamide | $^1$HNMR (400 MHz, DMSO-d6), δ 11.58 (s, 1H), 11.23 (s, 1H), 7.79 (dd, 1H, J = 2 and 8.4 Hz), 7.55 (dd, 1H, J = 2 and 8.4 Hz), 7.47-7.39 (m, 3H), 7.36-7.32 (m, 2H), 7.22 (bs, 1H), 6.94 (t, 1H, J = 8.8 Hz), 6.15 (bs, 1H), 4.88 (d, 1H, J = 4.8 Hz), 3.06 (s, 3H), 1.16 (s, 3H). MS: m/z 592.0 (M + 1). |
| 15 | ix | 3-(3-(5-((2-fluoro-4-iodophenyl)amino)-6,8- | $^1$H NMR (400 MHz, DMSO-d$_6$) δ 11.56 (s ,1H), 11.21 (s, 1H), 7.80-7.75 |

TABLE 2-continued

| Cmpd. No. | Intermed. No. | Name | Analytical data |
| --- | --- | --- | --- |
| | | dimethyl-2,4,7-trioxo-3,4,6,7-tetrahydro pyrido[4,3-d]pyrimidin-1(2H)-yl)phenyl)-N-methylpropanamide | (m, 2H), 7.54 (d, 1H, J = 8 Hz), 7.36 (t, J = 7.6 Hz, 1H), 7.24-7.19 (m, 3H), 6.94 (t, 1H, J = 8 Hz ), 3.05 (s, 3H), 2.84-2.81 (m, 2H), 2.50 (s, 3H), 2.37-2.35 (m,2H), 1.17 (s, 3H). MS: m/z 602.9 (M + 1). |
| 16 | xxvii | 2-(3-(5-((2-fluoro-4-iodophenyl)amino)-6,8-dimethyl-2,4,7-trioxo-3,4,6,7-tetrahydro pyrido[4,3-d]pyrimidin-1(2H)-yl)phenoxy)acetamide | $^1$H NMR (400 MHz, DMSO-d$_6$) δ 11.57 (s, 1H), 11.21 (s, 1H), 7.79 (dd, 1H, J = 1.6 and 10.4 Hz), 7.57-7.53 (m, 2H), 7.41 (brs, 1H), 7.37 (t, J = 8.0 Hz), 7.04-7.00 (m, 3H), 6.94 (t, J = 8 Hz, 1H,), 4.43 (s, 2H), 3.06 (s, 3H), 1.26 (s, 3H). MS: m/z 591.08 (M + 1). |
| 17 | iv | 1-(3-(1,1-dioxidothiazolidine-3-carbonyl)phenyl)-5-((2-fluoro-4-iodophenyl)amino)-6,8-dimethylpyrido[4,3-d]pyrimidine-2,4,7(1H,3H,6H)-trione | $^1$HNMR (400 MHz, DMSO-d6), δ 11.62 (s, 1H), 11.17 (s, 1H), 7.78 (dd, 1H, J = 2.0 and 10.4 Hz), 7.60-7.54 (m, 5H), 6.96 (t, 1H J = 8.4 Hz), 4.67 (bs, 2H), 3.99 (bs, 2H), 3.50 (t, 2H J = 7.4 Hz), 3.06 (s, 3H), 1.21 (s, 3H). |
| 18 | x | 5-((2-fluoro-4-iodophenyl)amino)-1-(3-(4-hydroxypiperidine-1-carbonyl)phenyl)-6,8-dimethylpyrido[4,3-d]pyrimidine-2,4,7(1H,3H,6H)-trione | $^1$HNMR (400 MHz, DMSO-d6), δ 11.60 (s, 1H), 11.17 (s, 1H), 7.78 (dd, 1H, J = 2 Hz, J = 10.4 Hz), 7.56-7.49 (m, 3H), 7.47-7.38 (m, 2H), 6.95 (t, 1H, J = 8.8 Hz), 4.81 (d, 1H, J = 3.6 Hz), 4.67 (bs, 2H), 4.01-3.99 (m, 1H0, 3.74-3.72 (m, 1H), 3.51-3.48 (m, 1H), 3.18-3.16 (m, 2H), 3.06 (s, 3H), 1.78-1.67 (m, 2H), 1.37-1.23 (m, 2H), 1.21 (s, 3H). MS: m/z 645.8 (M + 1). |
| 19 | xviii | N-cyclopropyl-3-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide | $^1$H NMR (400 MHz, DMSO-d$_6$) δ: 11.35 (brs, 2H), 7.88 (d, J = 4.0 Hz, 1H), 7.75 (d, J = 9.2 Hz, 1H), 7.52 (d, J = 8.4 Hz, 1H), 7.35 (t, J = 8.0 Hz, 1H), 7.21 (t, J = 7.2 Hz, 2H), 7.17 (s, 1H), 6.92 (t, J = 8.4 Hz, 1H), 3.07 (s, 3H), 2.82 (t, J = 8.0 Hz, 2H), 2.58-2.53 (m, 1H), 2.32 (t, J = 7.2 Hz, 2H), 1.18 (s, 3H), 0.58-0.53 (m, 2H), 0.33-0.29 (m, 2H). MS: m/z 630 (M + 1). |
| 20 | xxii | 2-(3-(5-((2-fluoro-4-iodophenyl)amino)-6,8-dimethyl-2,4,7-trioxo-3,4,6,7-tetrahydro pyrido[4,3-d]pyrimidin-1(2H)-yl)phenoxy)-2-methylpropanamide | $^1$HNMR (400 MHz, DMSO-d6), δ 11.56 (s, 1H), 11.20 (s, 1H), 7.79 (dd, J = 1.6 & J = 10.0 Hz, 1H), 7.61 (brs, 1H), 7.56-7.54 (m, 1H), 7.35 (t, J = 7.6 Hz 1H), 7.29 (brs, 1H), 7.04-7.02 (m, 1H), 6.96-6.92 (m, 3H) 3.06 (s, 3H), 1.43 (s, 6H), 1.26 (s, 3H), MS: m/z 619.6 (M + 1). |
| 21 | xxiii | 5-((2-fluoro-4-iodophenyl)amino)-6,8-dimethyl-1-(3-(4-methylpiperazine-1-carbonyl)phenyl)pyrido[4,3-d]pyrimidine-2,4,7(1H,3H,6H)-trione | $^1$HNMR (400 MHz, DMSO-d6), δ 11.60 (s, 1H), 11.18 (s, 1H), 7.79 (d, J = 10.4 Hz, 1H), 7.56-7.40 (m, 5H), 6.95 (t, J = 8.4 Hz, 1H), 3.61-3.37 (m, 4H), 3.06 (s, 3H), 2.35-2.29 (m, 4H), 2.19 (s, 3H), 1.21 (s, 3H) MS: m/z 644.7 (M + 1). |
| 77 | xxxi | 1-(3-(5-((2-fluoro-4-iodophenyl)amino)-6,8-dimethyl -2,4,7-trioxo-3,4,6,7-tetrahydropyrido [4,3-d] pyrimidin-1(2H)-yl)phenyl) cyclopropanecarboxamide | $^1$HNMR (400 MHz, DMSO-d6), δ 11.57 (s, 1H), 11.12 (s, 1H), 7.78 (dd, J = 1.6 and 8.8 Hz, 1H), 7.55 (dd, J = 0.8 and 8.4 Hz, 1H), 7.45-7.38 (m, 2H), 7.35-7.32 (m, 2H), 7.17 (brs, 1H), 6.95 (t, J = 8.4 Hz, 1H), 6.09 (brs, 1H), 3.06 (s, 3H), 1.34 (brs 2H), 1.21 (s, 3H), 0.98 (brs 2H). MS: m/z 601.9 (M + 1) |

Example-2: Synthesis of 5-((2-fluoro-4-iodophenyl)amino)-1-(3-(3-hydroxypyrrolidine-1-carbonyl)phenyl)-6,8-dimethylpyrido[4,3-d]pyrimidine-2,4,7(1H, 3H,6H)-trione (22)

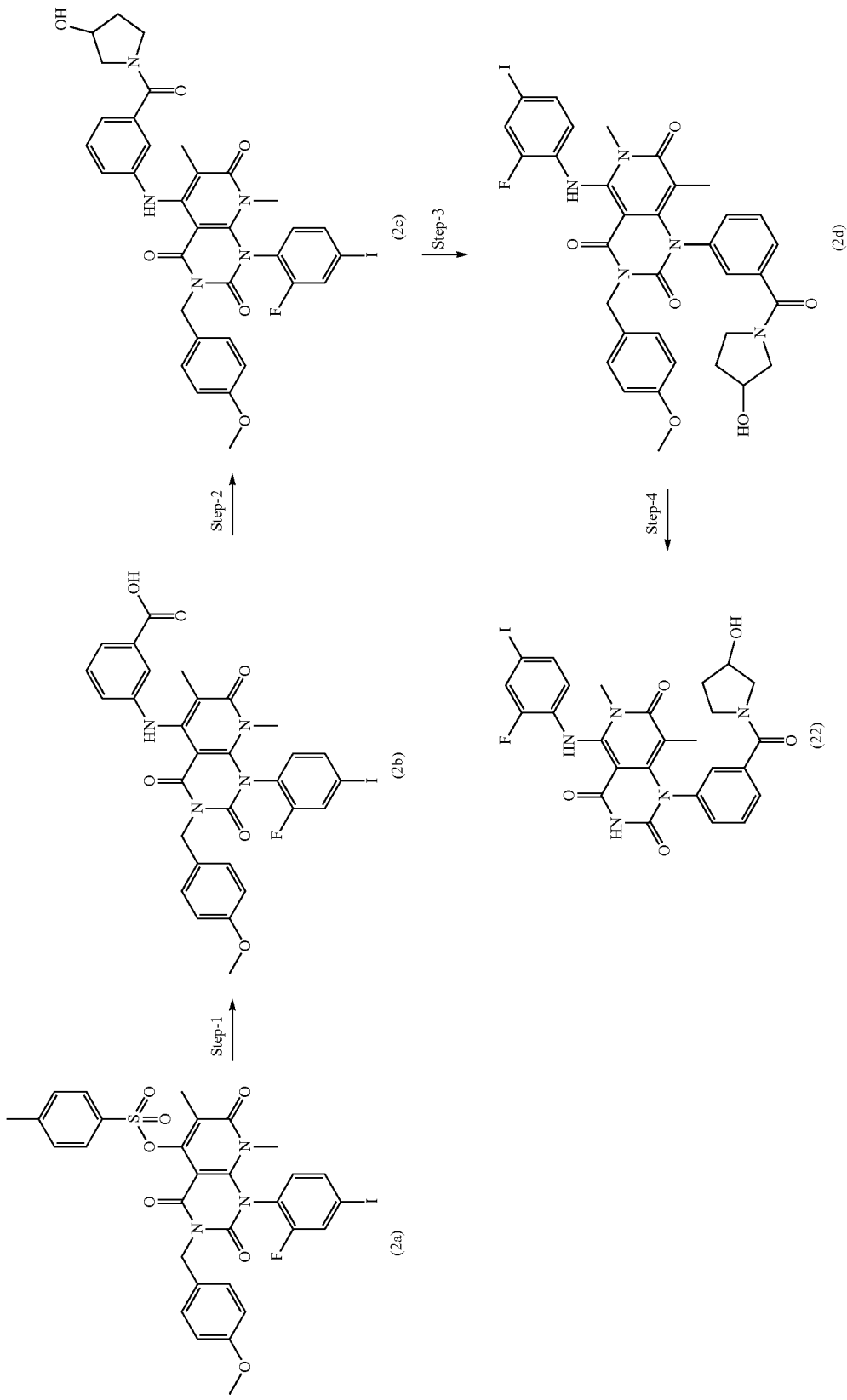

Step-1: Synthesis of 3-((1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl)amino)benzoic acid (2b)

To a stirred solution of 1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl 4-methylbenzene sulfonate (2a) (2.0 gm, 2.79 mmol) in DMA (5 ml) was added 2,6-lutidine (0.98 ml, 8.36 mmol) and 3-aminobenzoic acid (1.147 gm, 8.36 mmol). The reaction mixture was heated at 130° C. for 16 h. The reaction mixture was cooled to room temperature and water was added followed by extraction with Ethyl acetate. The organic phase was dried over sodium sulphate. The solvent was evaporated in vacuo and the residual solid was purified by silica gel column chromatography, eluting with Hexane: Ethyl acetate (1:1), to yield the titled compound (2b) (1.4 g)

$^1$H NMR (400 MHz, DMSO-d$_6$) δ 13.02 (s, 1H), 10.24 (s, 1H), 7.96 (dd, J=1.2 and 8.0 Hz, 1H), 7.74 (dd, J=1.2 and 8.4 Hz, 1H), 7.57 (d, J=8.0 Hz, 1H), 7.41-7.38 (m, 2H), 7.29-7.22 (m, 3H), 6.86 (d, J=8.8 Hz, 2H), 5.04-4.94 (m, 2H), 3.69 (s, 3H), 2.77 (s, 3H), 1.52 (s, 3H). [m/z=682.5 (M+1)].

Step-2: Synthesis of 1-(2-fluoro-4-iodophenyl)-5-((3-(3-hydroxypyrrolidine-1-carbonyl)phenyl)amino)-3-(4-methoxybenzyl)-6,8-dimethylpyrido[2,3-d]pyrimidine-2,4,7(1H,3H,8H)-trione (2c)

To a stirred solution of 3-((1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl)amino)benzoic acid (2b) (800 mg, 1.172 mmol) in THF (5 ml) was added EDC.HCl (494 mg, 2.58 mmol), HOBT (395 mg, 2.58 mmol), DIPEA (0.819 ml, 4.69 mmol) and pyrrolidin-3-ol hydrochloride (290 mg, 2.35 mmol). The reaction mixture was stirred at room temperature under N2 atm for 6 h. The reaction mixture was then partitioned between water and ethyl acetate. Organic phase was removed, washed with brine and dried over sodium sulphate. The solvent was evaporated in vacuop to afford crude 1-(2-fluoro-4-iodophenyl)-5-((3-(3-hydroxypyrrolidine-1-carbonyl)phenyl)amino)-3-(4-methoxybenzyl)-6,8-dimethylpyrido[2,3-d]pyrimidine-2,4,7(1H,3H,8H)-trione (2c) (550 mg) which was carried forward for the next step without further purification.

$^1$H NMR (400 MHz, DMSO-d$_6$) δ 10.17 (s, 1H), 7.97 (dd, J=1.6 and 9.6 Hz, 1H), 7.74 (dd, J=1.2 and 8.4 Hz, 1H), 7.40-7.34 (m, 2H), 7.28 (d, J=8.4 Hz, 2H), 7.11 (t, J=6.8 Hz, 1H), 7.04 (d, J=8.0 Hz, 1H), 6.97 (brs, 1H), 6.86 (d, J=8.8 Hz, 2H), 5.04-4.93 (m, 3H), 4.31-4.21 (m, 1H), 3.70 (s, 3H), 3.55-3.48 (m, 2H), 3.41-3.35 (m, 1H), 2.76 (s, 3H), 1.94-1.78 (m, 2H), 1.53 (s, 3H), 1.26-1.23 (m, 1H). [m/z=752.0 (M+1)].

Step-3: Synthesis of 5-((2-fluoro-4-iodophenyl)amino)-1-(3-(3-hydroxypyrrolidine-1-carbonyl)phenyl)-3-(4-methoxybenzyl)-6,8-dimethylpyrido[4,3-d]pyrimidine-2,4,7(1H,3H,6H)-trione (2d)

To a stirred solution of 1-(2-fluoro-4-iodophenyl)-5-((3-(3-hydroxypyrrolidine-1-carbonyl)phenyl)amino)-3-(4-methoxybenzyl)-6,8-dimethylpyrido[2,3-d]pyrimidine-2,4,7(1H,3H,8H)-trione (550 mg, 0.732 mmol) in THF (2 ml) and Methanol (1 ml), was added K$_2$CO$_3$ (202 mg, 1.464 mmol) at RT. The reaction mixture was stirred at room temperature for 3 h under N2 atm. The solvents were evaporated in vacuo and the residue was suspended in dilute HCl (10 ml). The suspension was extracted several times with ethyl acetate. The combined organic phase was washed with brine and dried over sodium sulphate. The solvent was evaporated in vacuo to afford crude 5-((2-fluoro-4-iodophenyl)amino)-1-(3-(3-hydroxypyrrolidine-1-carbonyl)phenyl)-3-(4-methoxybenzyl)-6,8-dimethylpyrido[4,3-d]pyrimidine-2,4,7(1H,3H,6H)-trione (2d) (500 mg) which was carried forward for the next step without further purification.

$^1$H NMR (400 MHz, DMSO-d$_6$) δ 11.09 (s, 1H), 7.78 (dd, J=2.0 and 10.4 Hz, 1H), 7.58-7.53 (m, 5H), 7.25 (d, J=8.8 Hz, 2H), 6.99 (t, J=8.8 Hz, 1H), 6.84 (d, J=8.8 Hz, 2H), 5.03-4.96 (m, 3H), 4.32-4.24 (m, 1H), 3.70 (s, 3H), 3.58-3.51 (m, 2H), 3.13-3.12 (m, 1H), 3.09 (s, 3H), 1.95-1.91 (m, 1H), 1.83-1.80 (m, 1H), 1.22 (s, 3H), 1.19-1.15 (m, 1H). [m/z=751.80 (M+1)].

Step-4: Synthesis of 5-((2-fluoro-4-iodophenyl)amino)-1-(3-(3-hydroxypyrrolidine-1-carbonyl)phenyl)-6,8-dimethylpyrido[4,3-d]pyrimidine-2,4,7(1H,3H,6H)-trione Aluminium chloride (0.887 g, 6.65 mmol) was added in small portions to a solution of crude 5-((2-fluoro-4-iodophenyl)amino)-1-(3-(3-hydroxypyrrolidine-1-carbonyl)phenyl)-3-(4-methoxybenzyl)-6,8-dimethylpyrido[4,3-d]pyrimidine-2,4,7(1H,3H,6H)-trione (2d) (0.500 g, 0.665 mmol) in Anisole (5 ml). The resulting reaction mixture was stirred at room temperature for 16 h, which was then quenched by addition of MeOH (15 ml) and 2N HCl (0.5 ml). The resulting mixture was concentrated under vacuum and the residue thus obtained was purified by silica gel column chromatography to yield the titled compound (22) (0.13 g)

$^1$H NMR (400 MHz, DMSO-d$_6$) δ 11.60 (s, 1H), 11.19 (s, 1H), 7.78 (dd, J=1.6 and 10.4 Hz, 1H), 7.56-7.51 (m, 5H), 6.96 (t, J=8.4 Hz, 1H), 5.0 (brs, 1H), 4.32-4.24 (m, 1H), 3.60-3.51 (m, 2H), 3.41-3.37 (m, 1H), 3.06 (s, 3H), 1.95-1.92 (m, 1H), 1.83-1.75 (m, 1H), 1.25 (s, 3H), 1.24-1.21 (m, 1H). [[m/z=631.50 (M+1)].

Example-3: Synthesis of 5-((2-fluoro-4-iodophenyl)amino)-6,8-dimethyl-1-(3-(piperazine-1-carbonyl)phenyl)pyrido[4,3-d]pyrimidine-2,4,7(1H,3H,6H)-trione (Compound 23)

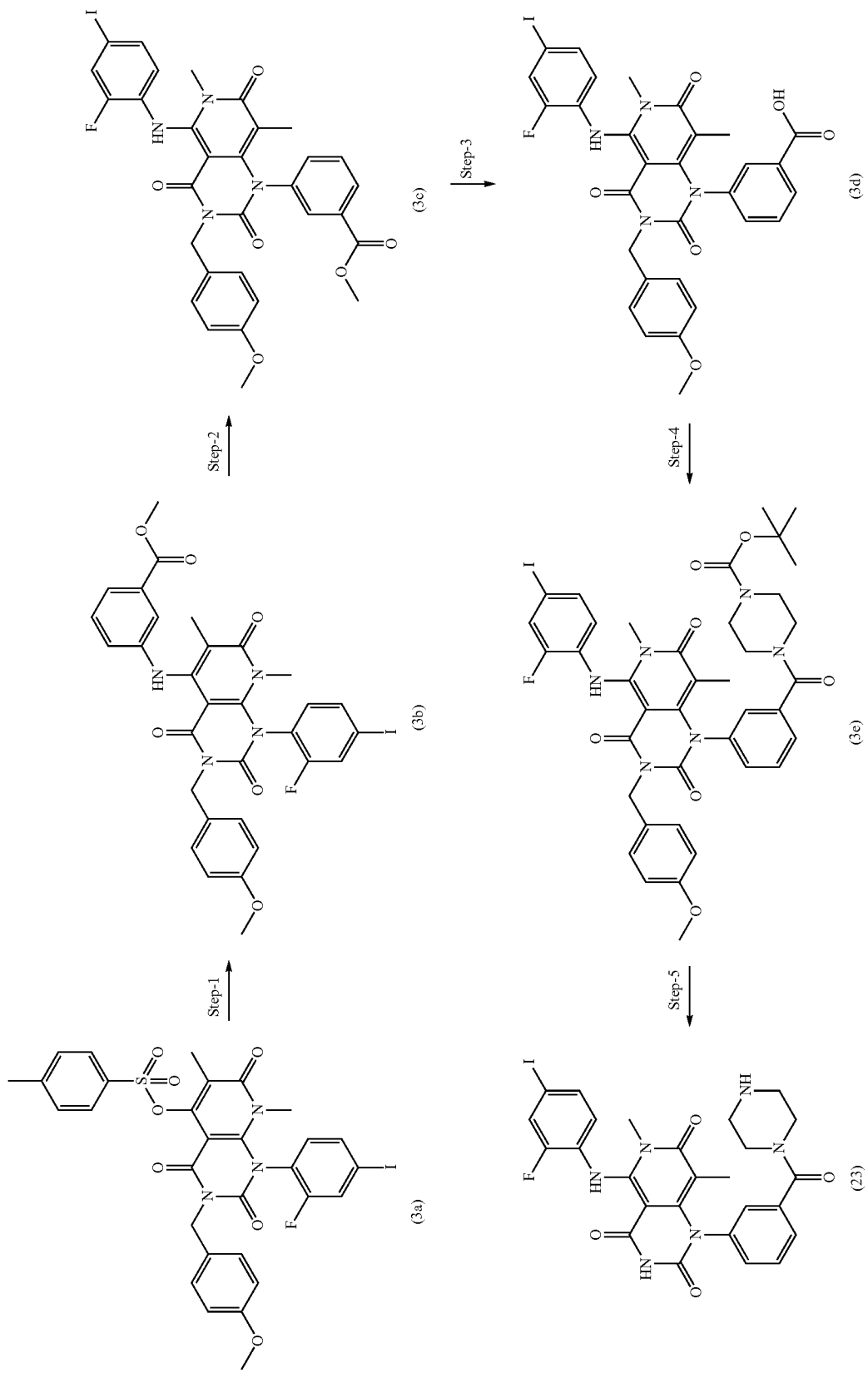

Step-1: Synthesis of methyl 3-((1-(2-fluoro-4-iodo-phenyl)-3-(4-methoxybenzyl)-6,8-dimethyl-2,4,7-trioxo-1,2,3,4,7,8-hexahydropyrido[2,3-d]pyrimidin-5-yl)amino)benzoate (3b)

To a stirred solution of 1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl 4-methylbenzene sulfonate (3a) (8.70 gm, 12.13 mmol) in DMA (10 ml) was added 2,6-lutidine (3.5 ml, 30.3 mmol) and methyl 3-aminobenzoate (5.5 g, 36.4 mmol). The reaction mixture was heated at 130° C. for 16 h. The reaction mixture was cooled to room temperature and water was added followed by extraction with Ethyl acetate. The organic phase was dried over sodium sulphate. The solvent was evaporated in vacuo and the residual solid was purified by silica gel column chromatography, eluting with Hexane: Ethyl acetate, to yield the titled compound (3b) (4.2 g)

$^1$H NMR (400 MHz, DMSO-d$_6$) δ 10.24 (s, 1H), 7.97 (d, J=9.6 Hz, 1H), 7.75 (d, J=8.4 Hz, 1H), 7.58 (d, J=7.6 Hz, 1H), 7.48-7.37 (m, 3H), 7.30-7.23 (m, 3H), 6.85 (d, J=8.4 Hz, 2H), 5.04-4.94 (m, 2H), 3.84 (s, 3H), 3.70 (s, 3H), 2.78 (s, 3H), 1.53 (s, 1H). [m/z=630.7 (M+1)].

Step-2: Synthesis of methyl 3-(5-((2-fluoro-4-iodo-phenyl)amino)-3-(4-methoxybenzyl)-6,8-dimethyl-2,4,7-trioxo-3,4,6,7-tetrahydropyrido[4,3-d]pyrimidin-1(2H)-yl)benzoate (3c)

To a stirred solution of methyl 3-((1-(2-fluoro-4-iodophenyl)-3-(4-methoxybenzyl)-6,8-dimethyl-2,4,7-trioxo-1,2,3,4,7,8-hexahydropyrido[2,3-d]pyrimidin-5-yl)amino)benzoate (3b) (3.20 g, 4.59 mmol) in THF (5 ml) and Methanol (10 ml), was added K$_2$CO$_3$ (2.54 g, 18.38 mmol) at RT. The reaction mixture was stirred at room temperature for 3 h under N$_2$ atm. The solvents were evaporated in vacuo and the residue was suspended in water, the precipitated product was collected by filtration and dried under high vacuum to afford the titled compound (3c), (2.1 g). The crude product was carried forward for the next step without further purification.

[m/z=697.0 (M+1)].

Step-3: Synthesis of 3-(5-((2-fluoro-4-iodophenyl)amino)-3-(4-methoxybenzyl)-6,8-dimethyl-2,4,7-trioxo-3,4,6,7-tetrahydropyrido[4,3-d]pyrimidin-1(2H)-yl)benzoic acid (3d)

A mixture of methyl 3-(5-((2-fluoro-4-iodophenyl)amino)-3-(4-methoxybenzyl)-6,8-dimethyl-2,4,7-trioxo-3,4,6,7-tetrahydropyrido[4,3-d]pyrimidin-1(2H)-yl)benzoate (0.500 g, 0.718 mmol) and LiOH.H$_2$O (0.120 g, 2.87 mmol) in THF (5.0 ml), MeOH (5.0 ml), and Water (5.0 ml) was stirred at room temperature for 17 h. The solvents were evaporated in vacuo and the residue was acidified with 1 N HCl until solid was precipitated. The product was collected by filtration and triturated in pentane, drying of this solid under vacuum afforded titled compound (3d), (0.312 g, 63.7%); which was carried forward for the next step without further purification.

$^1$H NMR (400 MHz, DMSO-d$_6$) δ 13.24 (s, 1H), 11.09 (s, 1H), 7.98-7.96 (m, 2H), 7.79 (dd, J=1.6 and 10.4 Hz, 1H), 7.70 (d, J=8.4 Hz, 1H), 7.62-7.53 (m, 2H), 7.25 (d, J=8.8 Hz, 2H), 7.00 (t, J=8.4 Hz, 1H), 6.86 (d, J=8.8 Hz, 2H), 3.70 (s, 3H), 3.09 (s, 3H), 1.17 (s, 3H). [m/z=683.0 (M+1)].

Step-4: Synthesis of tert-butyl 4-(3-(5-((2-fluoro-4-iodophenyl)amino)-3-(4-methoxybenzyl)-6,8-dimethyl-2,4,7-trioxo-3,4,6,7-tetrahydropyrido[4,3-d]pyrimidin-1(2H)-yl)benzoyl)piperazine-1-carboxylate (3e)

To a stirred solution of 3-(5-((2-fluoro-4-iodophenyl)amino)-3-(4-methoxybenzyl)-6,8-dimethyl-2,4,7-trioxo-3,4,6,7-tetrahydropyrido[4,3-d]pyrimidin-1(2H)-yl)benzoic acid (1 g, 1.465 mmol), EDC (0.421 g, 2.198 mmol), HOBT (0.337 g, 2.198 mmol) and tert-butyl piperazine-1-carboxylate (0.409 g, 2.198 mmol) in THF (5 ml); cooled to 0° C., was added Hunig's base (0.512 ml, 2.93 mmol). The resulting mixture was stirred under N2 atm for 2 h at room temperature. The solvent was evaporated in vacuo and the residue was partitioned between ethyl acetate (25 ml) and water (25 ml). The organic phase was separated and aq. phase was re-extracted with ethyl acetate. The combined organic layers were dried over sodium sulphate and evaporated in vacuo to obtain crude product, which was carried forward for the next step without further purification.

$^1$H NMR (400 MHz, DMSO-d$_6$) δ 7.78 (dd, J=2.0 and 6.0 Hz, 1H), 7.58-7.46 (m, 5H), 7.28 (d, J=8.8 Hz, 2H), 7.01 (t, J=8.4 Hz, 1H), 6.86 (d, J=8.8 Hz, 2H), 4.96 (s, 2H), 3.72 (s, 3H), 3.58-3.30 (m, 6H), 3.09 (s, 3H), 1.40 (s, 9H), 1.17 (s, 3H).

Step-5: Synthesis of 5-((2-fluoro-4-iodophenyl)amino)-6,8-dimethyl-1-(3-(piperazine-1-carbonyl)phenyl)pyrido[4,3-d]pyrimidine-2,4,7(1H,3H,6H)-trione (23)

Aluminium chloride (1.57 g, 11.76 mmol) was added in small portions to a solution of crude tert-butyl 4-(3-(5-((2-fluoro-4-iodophenyl)amino)-3-(4-methoxybenzyl)-6,8-dimethyl-2,4,7-trioxo-3,4,6,7-tetrahydropyrido[4,3-d]pyrimidin-1(2H)-yl)benzoyl)piperazine-1-carboxylate (1 g, 1.176 mmol) in Anisole (5 ml). The resulting reaction mixture was stirred at room temperature for 17 h, methanol (10 ml) was added dropwise and the resulting mixture was concentrated in vacuo. Aq. ammonia was added to the resulting residue and the reaction mixture was extracted several times with DCM. The combined organic phase was washed with brine and dried over sodium sulphate. The solvent was evaporated in vacuo and the residue was purified by column chromatography over neutral alumina to afford the titled compound (23) (0.113 g).

$^1$HNMR (400 MHz, DMSO-d6), δ (ppm): 7.78 (dd, J=2 & 10.4 Hz, 1H), 7.56-7.39 (m, 5H), 6.95 (t, J=8.8 Hz, 1H), 3.54-3.25 (m, 4H), 3.06 (s, 3H), 2.73-2.64 (m, 4H), 1.21 (s, 3H). [m/z=630.4 (M+1)].

Example 4: 1-(3-(azetidine-1-carbonyl)phenyl)-3-cyclopropyl-5-((2-fluoro-4-iodo phenyl)amino)-6,8-dimethylpyrido[4,3-d]pyrimidine-2,4,7(1H,3H,6H)-trione (Compound 24)

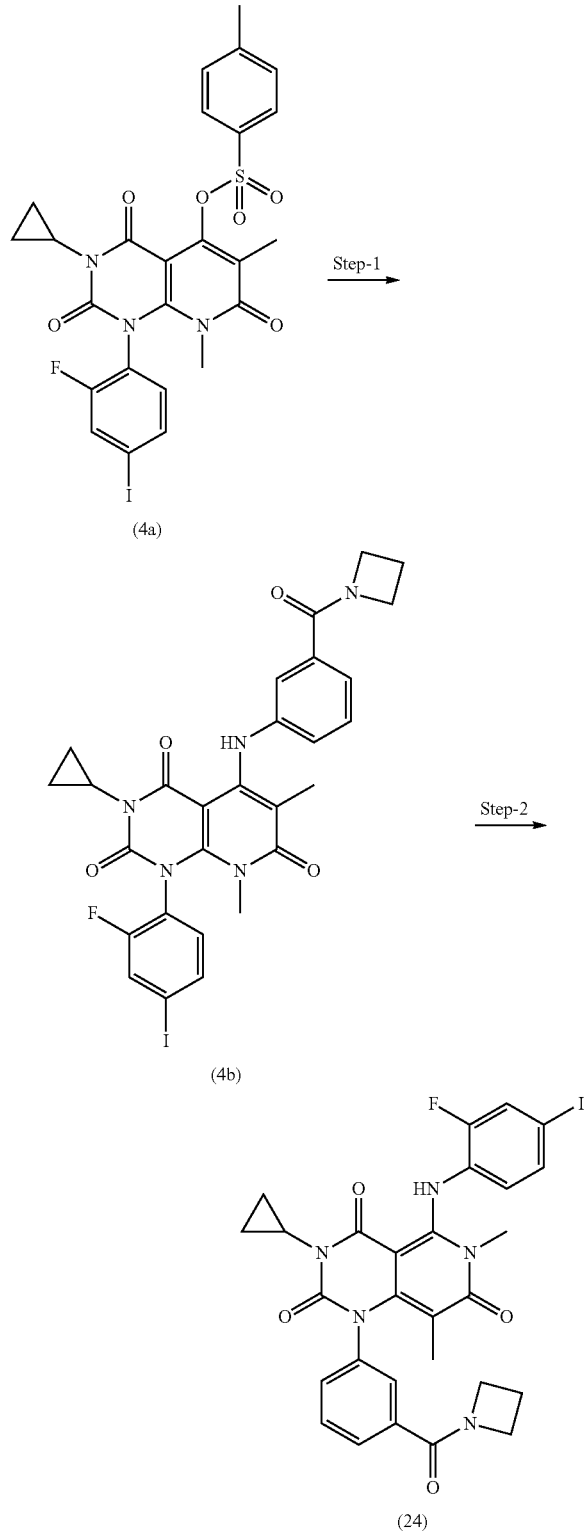

Step-1: Synthesis of 5-((3-(azetidine-1-carbonyl)phenyl)amino)-3-cyclopropyl-1-(2-fluoro-4-iodophenyl)-6,8-dimethylpyrido[2,3-d]pyrimidine-2,4,7(1H,3H,8H)-trione. (4b)

In a sealed tube 3-cyclopropyl-1-(2-fluoro-4-iodophenyl)-6,8-dimethyl-2,4,7-trioxo-1,2,3,4,7,8-hexahydropyrido[2,3-d]pyrimidin-5-yl 4-methylbenzenesulfonate (4a) (0.5 g, 0.78 mmol), (3-aminophenyl)(azetidin-1-yl)methanone (intermediate 1) (0.27 g, 1.56 mmol) were taken to the mixture DMA (2 ml) and 2,6-lutidine (0.42 mg, 3.92 mmol) were added and the mixture was heated at 130° C. for 16 hr under nitrogen atmosphere. After completion of the reaction, the reaction mixture was poured into ice cold water, the separated solid was filtered off and washed with water and dried under vacuum. The crude solid was purified by column chromatography to yield the titled compound (0.11 g).

$^1$H NMR (400 MHz, DMSO-$d_6$) δ (ppm): 10.13 (s, 1H), 7.95 (dd, J=1.6 & 9.2 Hz, 1H), 7.75-7.70 (m, 1H), 7.37 (t, J=8 Hz, 1H), 7.27 (t, J=8 Hz, 1H), 7.21 (d, J=7.6 Hz, 1H), 7.12-7.06 (m, 2H), 4.27 (t, J=7.2 Hz, 2H), 4.02 (t, J=7.6 Hz, 2H), 2.74 (s, 3H), 2.67-2.64 (m, 1H), 2.28-2.21 (m, 2H), 1.52 (s, 3H), 1.01-0.99 (m, 2H), 0.72-0.63 (m, 2H). [m/z=642.1 (M+1)].

Step-2: Synthesis of 1-(3-(azetidine-1-carbonyl)phenyl)-3-cyclopropyl-5-((2-fluoro-4-iodophenyl)amino)-6,8-dimethylpyrido[4,3-d]pyrimidine-2,4,7(1H,3H,6H)-trione (24)

5-((3-(azetidine-1-carbonyl)phenyl)amino)-3-cyclopropyl-1-(2-fluoro-4-iodophenyl)-6,8-dimethylpyrido[2,3-d]pyrimidine-2,4,7(1H,3H,8H)-trione (4b) (0.11 g, 0.17 mmol) was taken in tetrahydrofuran (3 ml) at room temperature, sodium methoxide (25% in MeOH, 371 mg, 1.71 mmol) was added and the reaction mixture was stirred at the same temperature for 1 hr under nitrogen atmosphere. The progress of the reaction was monitored by HPLC. After complete consumption of the substrate, the reaction mixture was diluted with HCl (2 mL, 2 N) and concentrated under vacuum. To the residue DCM (20 ml) was added, the organic layer was dried over sodium sulphate and concentrated under vacuum to give the crude compound which was purified by column chromatography to give the title product (0.09 g).

$^1$H NMR (400 MHz, DMSO-$d_6$) δ (ppm): 11.05 (s, 1H), 7.80-7.77 (m, 1H), 7.63-7.59 (m, 2H), 7.58-7.51 (m, 3H), 6.96-6.92 (m, 1H), 4.27-4.21 (m, 2H), 4.06-4.02 (m, 2H), 3.07 (s, 3H), 2.62-2.59 (m, 1H), 2.27-2.23 (m, 2H), 1.18 (s, 3H), 0.97-0.95 (m, 2H), 0.72-0.60 (m, 2H). ESI-MS:[m/z=642.1 (M+1)].

The compounds given below in Table 3: were prepared by procedure similar to the one described above in Example 4 with the above stated intermediates and with appropriate variations in reactants, reaction conditions and quantities of reagents.

TABLE 3

| Cmpd. No. | Intermed. No. | Name | Analytical data |
|---|---|---|---|
| 25 | iii | N-cyclopropyl-2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenoxy)acetamide | $^1$HNMR (400 MHz, DMSO-d6), δ 11.06 (s, 1H), 8.15 (d, J = 4 Hz, 1H), 7.79 (dd, J = 1.6 and 10.4 Hz, 1H), 7.55 (d, J = 8.4 Hz, 1H), 7.36 (t, J = 8.0 Hz, 1H), 6.99-6.91 (m, 4H), 4.44 (s, 2H), 3.07 (s, 3H), 2.68-2.51 (m, 2H), 1.25 (s, 3H), 0.96-0.95 (m, 2H), 0.68-0.59 (m, 4H), 0.48-0.44 (m, 2H). MS: m/z 672.0 (M + 1). |
| 26 | xxviii | 2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide | $^1$HNMR (400 MHz, DMSO-d6), δ 11.08 (brs, 1H), 7.78-7.76 (m, 1H), 7.52-7.49 (m, 2H), 7.38 (t, J = 7.6 Hz, 1H), 7.28-7.23 (m, 3H), 6.92-6.89 (m, 2H), 3.40 (s, 2H), 3.08 (s, 3H), 2.59 (brs, 1H), 1.18 (s, 3H), 0.95-0.93 (m, 2H), 0.65 (brs, 2H). MS: m/z 616.1 (M + 1). |
| 27 | xxix | 3-cyclopropyl-5-((2-fluoro-4-iodophenyl)amino)-6,8-dimethyl-1-(3-(pyrrolidine-1-carbonyl)phenyl)pyrido[4,3-d]pyrimidine-2,4,7(1H,3H,6H)-trione | $^1$HNMR (400 MHz, DMSO-d6), δ 11.04 (s, 1H), 7.79 (dd, J = 1.6 and 10.4 Hz, 1H), 7.56-7.45 (m, 5H), 6.94 (t, J = 8.8 Hz, 1H), 3.47-3.29 (m, 4H), 3.01 (s, 3H), 2.66-2.63 (m, 1H), 1.88-1.74 (m, 4H), 1.21 (s, 3H), 0.98-0.93 (m, 2H), 0.69-0.65 (m, 2H). MS: m/z 656.0 (M + 1). |
| 28 | vi | 2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-2-methylpropanamide | $^1$HNMR (400 MHz, DMSO-d6), δ 11.10 (s, 1H), 7.79 (d, J = 10.4 Hz, 1H), 7.55 (d, J = 8.8 Hz, 1H), 7.43-7.36 (m, 2H), 7.28-7.24 (m, 2H), 6.97-6.89 (m, 3H), 3.11 (s, 3H), 2.62-2.61 (m, 1H), 1.43 (s, 6H), 1.18 (s, 3H), 0.96-0.95 (m, 2H), 0.68 (brs, 2H). MS: m/z 644.1 (M + 1). |
| 29 | viii | 2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N,N-dimethylacetamide | $^1$HNMR (400 MHz, DMSO-d6), δ 11.07 (s, 1H), 7.79 (d, J = 1.2 Hz, 1H), 7.55 (d, J = 8.4 Hz, 1H), 7.38 (m, 1H), 7.27-7.19 (m, 3H), 6.92 (t, J = 8.4 Hz, 1H), 3.73 (s, 2H), 3.08 (s, 3H), 2.99 (s, 3H), 2.82 (s, 3H), 2.63-2.55 (m, 1H), 1.21 (s, 3H), 0.96-0.94 (m, 2H), 0.67(brs, 2H). MS: m/z 644.3 (M + 1). |
| 30 | vii | 2-(3-(3-cyclopropyl-5-((2-fluoro-4-iodophenyl)amino)-6,8-dimethyl-2,4,7-trioxo-3,4,7,8-tetrahydropyrido[2,3-d]pyrimidin-1(2H)-yl)phenyl)-2,2-difluoroacetamide | $^1$HNMR (400 MHz, DMSO-d6), δ 11.08 (s, 1H), 8.42 (brs, 1H), 8.07 (brs, 1H), 7.79 (dd, 1H, J = 1.6 & 10.4 Hz), 7.65-7.54 (m, 5H), 6.94 (t, J = 8.4 Hz, 1H), 3.08 (s, 3H), 2.64-2.59 (m, 1H), 1.13 (s, 3H), 0.98-0.93 (m, 2H), 0.70-0.66 (m, 2H). MS: m/z 652.0 (M + 1). |
| 31 | xvi | 2-(3-(3-Cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N-(oxetan-3-yl)acetamide | $^1$HNMR (400 MHz, DMSO-d6), δ11.07 (s, 1H), 8.85 (d, 1H, J = 6.4 Hz), 7.77 (d, 1H, J = 9.6 Hz), 7.53 (d, 1H, J = 8.4 Hz), 7.38 (t, 1H, J = 7.6 Hz), 7.27-7.16 (m, 3H), 6.91 (t, 1H, J = 8.8 Hz), 4.76-4.73 (m, 1H), 4.71-4.67 (m, 2H), 4.39-4.36 (m, 2H), 3.46 (s, 2H), 3.08 (s, 3H), 2.55-2.54 (m, 1H), 1.16 (s, 3H), 0.95-0.93 (m, 2H), 0.7-0.6 (m, 2H). MS: m/z 672.0 (M + 1). |
| 32 | xiii | 2-(3-(3-Cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-2-hydroxyacetamide | $^1$HNMR (400 MHz, DMSO-d6), δ 11.08 (s, 1H), 7.78 (d, 1H, J = 9.2 Hz), 7.54 (d, 1H, J = 8.4 Hz), 7.46-7.36 (m, 4H), 7.30 (d, 1H, J = 7.6 Hz), 7.22 (s, 1H), 6.93-6.87 (m, 1H), 6.14 (d, 1H, J = 4.8 Hz), 4.88 (d, 1H, J = 4.8 Hz), 3.08 (s, 3H), 2.67-2.60 (m, 1H), 1.16 (s, 3H), 1.0-0.9 (m, 2H), 0.7-0.6 (m, 2H). MS: m/z 632.0 (M + 1). |
| 33 | xvii | 3-Cyclopropyl-5-((2-fluoro-4-iodophenyl)amino)-1-(3-(2-(3-hydroxyazetidin-1-yl)-2-oxo ethyl)phenyl)-6,8-dimethylpyrido[4,3-d]pyrimidine-2,4,7(1H,3H,6H)-trione | $^1$HNMR (400 MHz, DMSO-d6), δ 11.11 (bs, 1H), 7.78 (dd, 1H, J = 1.6 and 10.4), 7.54 (d, 1H, J = 8.4), 7.40-7.36 (m, 1H), 7.27-7.23 (m, 2H), 7.20-7.14 (m, 1H), 6.91 (t, 1H, J = 8.8 Hz), 5.72 (bs, 1H), 4.42 (bs, 1H), 4.34-4.30 (m, 1H), 4.03-3.99 (m, 1H), 3.89-3.59 (m, 1H), 3.58- |

TABLE 3-continued

| Cmpd. No. | Intermed. No. | Name | Analytical data |
|---|---|---|---|
| | | | 3.46 (m, 1H), 3.33 (s, 2H), 3.07 (s, 3H), 2.63-2.60 (m, 1H), 1.19 (s, 3H), 0.95-0.93 (m, 2H), 0.65-0.64 (m, 2H). MS: m/z 672.0 (M + 1). |
| 34 | xxvi | 3-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide | $^1$H NMR (400 MHz, DMSO-d$_6$) δ 11.06 (s, 1H), 7.78 (d, J = 10.4 Hz, 1H), 7.55 (d , J = 8.8 Hz, 1H), 7.37-7.30 (m, 2H), 7.23-7.18 (m, 3H), 6.92 (t, J = 8.4 Hz, 1H), 6.75 (brs, 1H), 3.08 (s, 3H), 2.82 (t, J = 7.6 Hz, 2H), 2.66-2.60 (m, 1H), 2.36 (t, J = 8.4 Hz, 2H), 1.16 (s, 3H), 0.96-0.94 (m, 2H), 0.67-0.60 (m, 2H). MS: m/z 630.1 (M + 1). |
| 35 | xxvii | 2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenoxy)acetamide | $^1$H NMR (400 MHz, DMSO-d$_6$) δ 11.05 (s, 1H), 7.78 (dd, J = 10.0 and 1.6 Hz, 1H), 7.58-7.53 (m, 2H), 7.42 (bs, 1H), 7.37 (t, J = 8.0 Hz, 1H), 7.03-6.98 (m, 3H), 6.93 (t, J = 8.4 Hz, 1H), 4.43 (s, 2H), 3.07 (s, 3H), 2.63-2.59 (m, 1H), 1.25 (s, 3H), 0.96-0.94 (m, 2H), 0.68-0.66 (m, 2H). MS: m/z 632.1 (M + 1). |
| 36 | ix | 3-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N-methylpropanamide | $^1$H NMR (400 MHz, DMSO-d$_6$) δ 11.32 (s, 1H), 7.53 (dd, J = 9.6 and 2 Hz, 1H), 7.46 (d, J = 8.4 Hz, 1H), 7.35 (t, J = 7.6 Hz, 1H), 7.23-7.20 (m, 1H), 7.15-7.12 (m, 2H), 6.71 (t, J = 8.0 Hz, 1H,), 5.4 (brs, 1H), 3.2 1 (s, 3H), 3.00 (t, J = 7.2 Hz, 2H), 2.76-2.72 (m, 4H), 2.47 (t, J = 7.2 Hz, 2H), 1.35 (s, 3H), 1.16-1.11 (m, 2H), 0.82-0.78 (m, 2H). MS: m/z 643.58 (M + 1). |
| 37 | xxiv | N-cyclopropyl-3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)benzamide | $^1$HNMR (400 MHz, DMSO-d6), δ 11.06 (s, 1H), 8.53-8.52 (d, 1H, J = 4.4 Hz), 7.85-7.82 (m, 1H), 7.80-7.77 (m, 2H), 7.56-7.53 (m, 3H), 6.96-6.92 (t, 1H, J = 8 Hz), 3.08 (s, 3H), 2.86-2.82 (m, 1H), 2.64-2.59 (m, 1H), 1.17 (s, 3H), 0.96-0.94 (m, 2H), 0.70-0.68 (m, 4H), 0.60-0.56 (m, 2H). MS: m/z 642.0 (M + 1). |
| 38 | iv | 3-cyclopropyl-1-(3-(1,1-dioxidothiazolidine-3-carbonyl)phenyl)-5-((2-fluoro-4-iodophenyl)amino)-6,8-dimethylpyrido[4,3-d]pyrimidine-2,4,7(1H,3H,6H)-trione | $^1$HNMR (400 MHz, DMSO-d6), δ 11.03 (s, 1H), 7.78 (dd, 1H, J = 1.6 Hz and 10.4 Hz), 7.60-7.54 (m, 5H), 6.96-6.92 (t, 1H, J = 8.8 Hz), 4.65 (bs, 2H), 4.01 (bs, 2H), 3.48 (t, 2H J = 7.2 Hz), 3.07 (s, 3H), 2.66-2.55 (m, 1H), 1.17 (s, 3H), 0.98-0.90 (m, 2H), 0.72-0.60 (m, 2H). MS: m/z 705.9 (M + 1). |
| 39 | v | 3-cyclopropyl-1-(3-(1,1-dioxidothiomorpholine-4-carbonyl)phenyl)-5-((2-fluoro-4-iodophenyl)amino)-6,8-dimethylpyrido[4,3-d]pyrimidine-2,4,7(1H,3H,6H)-trione | $^1$HNMR (400 MHz, CDCl3-d1), δ 11.29 (s, 1H), 7.55-7.53 (m, 2H), 7.49-7.47 (m, 3H), 7.39-7.37 (m, 1H), 6.73 (t, 1H, J = 8.4 Hz), 4.18-4.14 (m, 4H), 3.23 (s, 3H), 3.17-3.13 (m, 4H), 2.78-2.74 (m, 1H), 1.39 (s, 3H), 1.16-1.14 (m, 2H), 0.85-0.75 (m, 2H). MS: m/z 719.9 (M + 1). |
| 40 | xviii | N-cyclopropyl-3-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide | $^1$HNMR (400 MHz, DMSO-d6), δ 11.07 (s, 1H), 7.94-7.77 (m, 1H), 7.91-7.90 (d, 1H, J = 3.6 Hz), 7.55-7.53 (m, 1H), 7.36-7.32 (m, 1H), 7.22-7.17 (m, 3H), 6.89 (t, 1H J = 8 Hz), 3.07 (s, 3H), 2.83-2.79 (m, 2H), 2.51 (bs, 2H), 2.31 (bs, 2H), 1.17 (s, 3H), 0.95-0.93 (m, 2H), 0.65 (bs, 2H), 0.58-0.53 (m, 2H), 0.31-0.30 (bs, 2H). MS: m/z 670 (M + 1). |
| 41 | iii | N-cyclopropyl-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenoxy)acetamide | $^1$HNMR (400 MHz, DMSO-d6), δ 11.19 (s, 1H), 8.15 (d, J = 4.4 Hz, 1H), 7.79 (dd, J = 2 and 10.4 Hz, 1H), 7.55 (dd, J = 1.2 and 8.4 Hz, 1H), 7.38 (t, J = 8.4 Hz, 1H), 7.03-6.98 (m, 3H), 6.94 (t, J = 8.8 Hz, 1H), 4.45 (s, 2H), 3.21 (s, 3H), 2.69-2.64 (m, 1H), 2.08 (s, 3H), 1.26 (s, 3H), 0.64-0.59 (m, 2H), 0.47-0.43 (m, 2H). MS: m/z 645.7 (M + 1). |
| 42 | xxviii | 2-(3-(5-((2-fluoro-4-iodophenyl)amino)-3,6,8-trimethyl-2,4,7-trioxo- | $^1$HNMR (400 MHz, DMSO-d6), δ 11.20 (s, 1H), 7.79 (dd, J = 1.6 and 10.4 Hz, 1H), 7.56-7.48 (m, 2H), 7.39 (t, J = 7.6 |

TABLE 3-continued

| Cmpd. No. | Intermed. No. | Name | Analytical data |
|---|---|---|---|
| | | 3,4,6,7-tetrahydropyrido[4,3-d]pyrimidin-1(2H)-yl)phenyl)acetamide | Hz, 1H), 7.30-7.24 (m, 3H), 6.95-6.90 (m, 2H), 3.41 (s, 2H), 3.21 (s, 3H), 3.09 (s, 3H), 1.20 (s, 3H). MS: m/z 590.0 (M + 1). |
| 43 | vi | 2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)-2-methylpropanamide | $^1$HNMR (400 MHz, DMSO-d6), δ 11.25 (s, 1H), 7.79 (d, J = 10.4 Hz, 1H), 7.55 (d, J = 8.0 Hz, 1H), 7.43-7.41 (m, 2H), 7.30-7.27 (m, 2H), 6.98-6.90 (m, 3H), 3.22 (s, 3H), 3.09 (s, 3H), 1.44 (s, 6H), 1.18 (s, 3H) MS: m/z 618.1 (M + 1). |
| 44 | viii | 2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)-N,N-dimethylacetamide | $^1$HNMR (400 MHz, DMSO-d6), δ 11.19 (s, 1H), 7.79 (dd, J = 1.6 & 10 Hz, 1H), 7.55 (d, J = 8.4 Hz, 1H), 7.42-7.20 (m, 4H), 6.92 (t, J = 8.4 Hz, 1H), 3.73 (s, 2H), 3.21 (s, 3H), 3.08 (s, 3H), 2.99 (s, 3H), 2.82 (s, 3H), 1.22 (s, 3H). MS: m/z 618.1 (M + 1). |
| 45 | vii | 2,2-difluoro-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)acetamide | $^1$HNMR (400 MHz, DMSO-d6), δ 11.20 (s, 1H), 8.41 (brs, 1H), 8.07 (brs, 1H), 7.79 (dd, J = 1.2 & 10.0 Hz, 1H), 7.63-7.54 (m, 5H), 6.94 (t, J = 8.8 Hz, 1H), 3.09 (s, 3H), 3.21 (s, 3H), 1.14 (s, 3H). MS: m/z 626.0 (M + 1). |
| 46 | xv | 1-(3-(2-(Azetidin-1-yl)-2-oxoethyl)phenyl)-5-((2-fluoro-4-iodophenyl)amino)-3,6,8-trimethylpyrido[4,3-d]pyrimidine-2,4,7(1H,3H,6H)-trione | $^1$HNMR (400 MHz, DMSO-d6), δ 11.20 (s, 1H), 7.79 (dd, 1H, J = 10 & 1.6), 7.56-7.53 (m, 1H), 7.42-7.38 (m, 1H), 7.30-7.22 (m, 3H), 6.93 (t, 1H, J = 8.4 Hz), 4.15 (t, 2H, J = 7.6 Hz), 3.83 (t, 2H, J = 7.6 Hz), 3.43 (s, 2H), 3.21 (s, 3H), 3.08 (s, 3H), 2.18-2.15 (m, 2H), 1.2 (s, 3H). MS: m/z 630.0 (M + 1). |
| 47 | xiii | 2-(3-(5-((2-Fluoro-4-iodophenyl)amino)-3,6,8-trimethyl-2,4,7-trioxo-3,4,6,7-tetrahydropyrido[4,3-d]pyrimidin-1(2H)-yl)phenyl)-2-hydroxyacetamide | $^1$HNMR (400 MHz, DMSO-d6), δ 11.21 (s, 1H), 7.78 (dd, 1H, J = 1.6 & 8.8 Hz), 7.54 (d, 1H, J = 8.8 Hz), 7.48-7.33 (m, 5H), 7.22 (s, 1H), 6.92 (t, 1H, J = 8.8 Hz), 6.15 (bs, 1H), 4.88 (d, 1H, J = 4.8 Hz), 3.21 (s, 3H), 3.08 (s, 3H), 1.16 (s, 3H). MS: m/z 605 (M + 1). |
| 48 | xvii | 5-((2-Fluoro-4-iodophenyl)amino)-1-(3-(2-(3-hydroxyazetidin-1-yl)-2-oxoethyl)phenyl)-3,6,8-trimethylpyrido[4,3-d]pyrimidine-2,4,7(1H,3H,6H)-trione | $^1$HNMR (400 MHz, DMSO-d6), δ 11.20 (s, 1H), 7.78 (d, 1H, J = 9.6 Hz), 7.54 (d, 1H, J = 8 Hz), 7.41-7.38 (m, 1H), 7.30-7.22 (m, 3H), 6.93 (t, 1H, J = 8.4 Hz), 5.72 (d, 1H, J = 6), 4.42-4.35 (m, 1H), 4.32-4.01 (m, 1H), 3.99-3.90 (m, 1H), 3.89-3.87 (m, 1H), 3.58-3.54 (m, 1H), 3.33 (s, 2H), 3.20 (s, 3H), 3.08 (s, 3H), 1.2 (s, 3H). MS: m/z 646 (M + 1). |
| 49 | xi | 3-(5-((2-Fluoro-4-iodophenyl)amino)-3,6,8-trimethyl-2,4,7-trioxo-3,4,6,7-tetrahydropyrido[4,3-d]pyrimidin-1(2H)-yl)-N-(oxetan-3-yl)benzamide | $^1$HNMR (400 MHz, DMSO-d6), δ 11.18 (s, 1H), 7.89-7.86 (m, 2H), 7.79 (dd, 1H, J = 10.4 and 2 Hz), 7.59-7.54 (m, 3H), 6.95 (t, 1H, J = 8.4 Hz), 4.85 (t, 1H, J = 5.6 Hz), 4.45-4.44 (m, 1H), 4.30-4.28 (m, 2H), 3.60-3.56 (m, 1H), 3.49-3.46 (m, 1H), 3.19 (s, 3H), 3.08 (s, 3H), 1.19 (s, 3H). MS: m/z 632.0 (M + 1). |
| 50 | xvi | 2-(3-(5-((2-Fluoro-4-iodophenyl)amino)-3,6,8-trimethyl-2,4,7-trioxo-3,4,6,7-tetrahydropyrido[4,3-d]pyrimidin-1(2H)-yl)phenyl)-N-(oxetan-3-yl)acetamide | $^1$HNMR (400 MHz, DMSO-d6), δ 11.20 (s, 1H), 8.85 (d, 1H, J = 6.4 Hz), 7.78 (d, 1H, J = 10.4 Hz), 7.54 (d, 1H, J = 8.4 Hz), 7.41-7.37 (m, 1H), 7.30-7.24 (m, 3H), 6.92 (t, 1H, J = 8.4 Hz), 4.78-4.74 (m, 1H), 4.73-4.67 (m, 2H), 4.38 (t, 2H, J = 6 Hz), 3.46 (s, 2H), 3.20 (s, 3H), 3.08 (s, 3H), 1.18 (s, 3H). MS: m/z 646.0 (M + 1). |
| 51 | xii | 3-(5-((2-Fluoro-4-iodophenyl)amino)-3,6,8-trimethyl-2,4,7-trioxo-3,4,6,7-tetrahydropyrido[4,3-d]pyrimidin- | $^1$HNMR (400 MHz, CDCl$_3$), δ 11.41 (s, 1H), 7.79 (d, 1H, J = 7.6 Hz), 7.71 (bs, 1H), 7.57-7.46 (m, 4H), 6.72 (t, 1H, J = 8.4 Hz), 6.46 (d, 1H, J = 7.6 Hz), 4.74 (bs, 1H), 4.12-3.82 (m, 4H), 3.39 (s, 3H), 3.23 (s, 3H), 2.41-2.35 (m, 1H), 2.00- |

TABLE 3-continued

| Cmpd. No. | Intermed. No. | Name | Analytical data |
|---|---|---|---|
| | | 1(2H)-yl)-N-(tetrahydrofuran-3-yl)benzamide | 1.90 (m, 1H), 1.35 (s, 3H).<br>MS: m/z 646.0 (M + 1). |
| 52 | xiv | 3-(5-((2-fluoro-4-iodophenyl)amino)-3,6,8-trimethyl-2,4,7-trioxo-3,4,6,7-tetrahydropyrido[4,3-d]pyrimidin-1(2H)-yl)-N-(tetrahydro-2H-pyran-4-yl)benzamide | $^1$HNMR (400 MHz, DMSO-d6) δ 11.21 (s, 1H), 8.42 (d, 1H, J = 7.6 Hz), 7.92-7.90 (m, 1H), 7.84 (s, 1H), 7.79 (dd, 1H, J = 2 & 8.4 Hz), 7.59-7.54 (m, 3H), 6.93 (t, 1H, J = 8.8 Hz), 4.05-3.99 (m, 1H), 3.86 (dd, 2H, J = 2 & 9.2 Hz), 3.41-3.38 (m, 2H), 3.21 (s, 3H), 3.08 (s, 3H), 1.77-1.74 (m, 2H), 1.60-1.56 (m, 2H), 1.19 (s, 3H). |
| 53 | xx | 3-(5-((2-fluoro-4-iodophenyl)amino)-3,6,8-trimethyl-2,4,7-trioxo-3,4,6,7-tetrahydropyrido[4,3-d]pyrimidin-1(2H)-yl)-N-(1-(hydroxymethyl)cyclopropyl)benzamide | $^1$HNMR (400 MHz, DMSO-d6), δ: 11.2 (s, 1H), 8.79 (s, 1H), 7.91-7.78 (m, 3H), 7.58-7.51 (m, 3H), 6.96 (t, 1H, J = 8.8 Hz), 4.79 (t, 1H, J = 6 Hz), 3.52 (bs, 2H), 3.21 (s, 3H), 3.09 (s, 3H), 1.93 (s, 3H), 0.75-0.70 (m, 4H).<br>MS: m/z 646.0 (M + 1). |
| 78 | xxxi | 1-(3-(3-cyclopropyl-5-((2-fluoro-4-iodophenyl)amino)-6,8-dimethyl-2,4,7-trioxo-3,4,6,7-tetrahydropyrido[4,3-d] pyrimidin-1(2H)-yl) phenyl)cyclopropanecarboxamide | $^1$HNMR (400 MHz, DMSO-d6), δ 11.05 (s, 1H), 7.79 (dd, J = 1.6 and 8.8 Hz, 1H), 7.55 (dd, J = 1.2 and 8.4 Hz, 1H), 7.45-7.29 (m, 4H), 7.19 (brs, 1H), 6.93 (t, J = 8.4 Hz, 1H), 5.97 (brs, 1H), 3.08 (s, 3H), 2.62-2.59 (m, 1H), 1.35 (brs, 2H), 1.21 (s, 3H), 0.98-0.93 (m, 4H), 0.69-0.65 (m, 2H).<br>MS: m/z 642.0 (m + 1) |

Example-5: N-cyclopropyl-3-(5-((2-fluoro-4-iodophenyl)amino)-3,6,8-trimethyl-2,4,7-trioxo-3,4,6,7-tetrahydropyrido[4,3-d]pyrimidin-1(2H)-yl)benzamide (Compound 54)

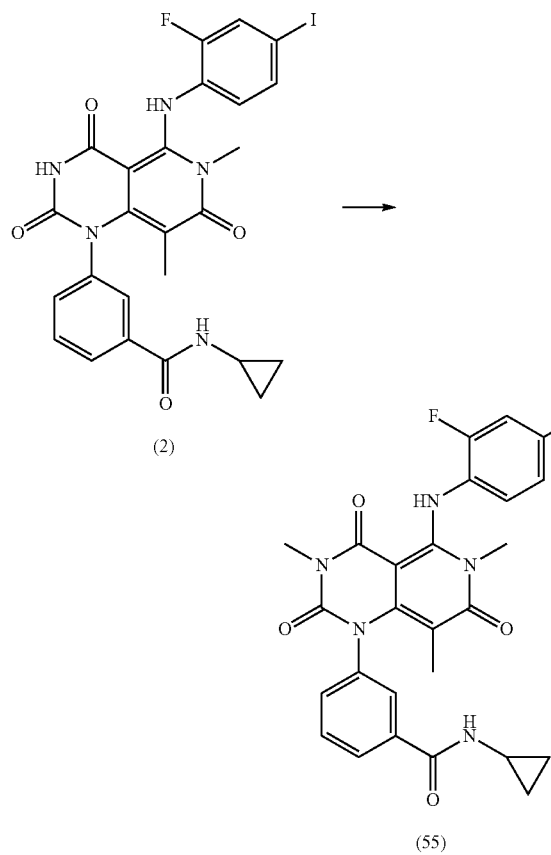

To a mixture of N-cyclopropyl-3-(5-((2-fluoro-4-iodophenyl)amino)-6,8-dimethyl-2,4,7-trioxo-3,4,6,7-tetrahydropyrido[4,3-d]pyrimidin-1(2H)-yl)benzamide (2) (110 mg, 0.183 mmol) and $K_2CO_3$ (0.51 mg, 0.37 mmol) in DMF (3 ml) was added Iodomethane (9.15 µl, 0.146 mmol) portion wise. The solution was heated at 60° C. for 3 hrs. The reaction mixture was cooled to room temperature followed by the addition of water and the mixture was extracted with ethyl acetate (3×10 ml). The combined organic layers were washed with water, brine and dried over sodium sulfate. The organic layer was concentrated to obtain a crude product, which was purified by column chromatography to yield the product (55) (0.06 gm).

$^1$H NMR (400 MHz, DMSO-d$_6$) δ 11.19 (s, 1H), 8.53 (d, 1H, J=4 Hz), 7.87-7.84 (m, 1H), 7.80-7.77 (m, 2H), 7.59-7.54 (m, 3H), 6.95 (t, 1H, J=8.0 Hz), 3.21 (s, 3H), 3.09 (s, 3H), 2.85-2.83 (m, 1H), 1.18 (s, 3H), 0.70-0.68 (m, 2H), 0.58-0.57 (m, 2H).

MS: m/z 616.1 (M+1)].

The compounds given below in Table 4: were prepared by procedure similar to the one described above in Example 5 using the above prepared compounds as starting material and with appropriate variations in reactants, reaction conditions and quantities of reagents.

TABLE 4

| Cmpd. | Intermed. No. | Name | Analytical data |
|---|---|---|---|
| 55 | 2 | N-cyclopropyl-3-(5-((2-fluoro-4-iodophenyl)amino)-3-(2-hydroxyethyl)-6,8-dimethyl-2,4,7-trioxo-3,4,6,7-tetrahydropyrido[4,3-d]pyrimidin-1(2H)-yl)benzamide | $^1$H NMR (400 MHz, DMSO-d$_6$) δ 11.24 (s, 1H), 8.56 (d, 1H, J = 4 Hz), 7.87-7.78 (m, 3H), 7.58-7.52 (m, 3H), 6.96 (t, 1H, J = 8.4 Hz), 4.80 (t, 1H, J = 6 Hz), 3.93 (t, 2H, J = 6.4), 3.55-3.51 (m, 2H), 3.08 (s, 3H), 2.86-2.81 (m, 1H), 1.17 (s, 3H), 0.70-0.68 (m, 2H), 0.58-0.57 (m, 2H), MS: m/z 646.1 (M + 1)]. |
| 56 | 3 | 1-(3-(azetidine-1-carbonyl)phenyl)-5-((2-fluoro-4-iodophenyl)amino)-3,6,8-trimethyl pyrido[4,3-d]pyrimidine-2,4,7(1H,3H,6H)-trione | $^1$H NMR (400 MHz, CDCl3) δ 11.39 (s, 1H), 7.66-7.62 (m, 2H), 7.55-7.51 (m, 2H), 7.50-7.43 (m, 2H), 6.71 (t, 1H, J = 8 Hz), 4.4-4.28 (m, 4H), 3.38 (s, 3H), 3.23 (s, 3H), 2.41-2.33 (m, 2H), 1.34 (s, 3H). MS: m/z 616.1 (M + 1)]. |
| 57 | 16 | 2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenoxy)acetamide | $^1$H NMR (400 MHz, DMSO-d$_6$) δ 11.19 (s, 1H), 7.78 (d, 1H, J = 8 Hz), 7.57-7.53 (m, 2H), 7.41-7.35 (m, 2H), 7.04-7.00 (m, 3H), 6.93 (t, 1H, J = 8 Hz ), 4.43 (s, 2H), 3.20 (s, 3H), 3.08 (s, 3H), 1.27 (s, 3H). MS: m/z 605.9 (M + 1)]. |
| 58 | 4 | N-cyclopropyl-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)acetamide | $^1$H NMR (400 MHz, DMSO-d$_6$) δ 11.20 (s, 1H), 8.14 (d, 1H, J = 4 Hz), 7.79 (dd, 1H, J = 2 and 10.4 Hz), 7.55 (dd, 1H, J = 1.2 and 8.4 Hz), 7.41-7.37 (m, 1H), 7.30-7.22 (m, 3H), 6.93 (t, 1H, J = 8.8 Hz), 3.37 (s, 2H), 3.21 (s, 3H), 3.08 (s, 3H), 2.59-2.56 (m, 1H), 1.18 (s, 3H), 0.60-0.58 (m, 2H), 0.37-0.33 (m, 2H). MS: m/z 630.1 (M + 1)]. |
| 59 | 4 | N-cyclopropyl-2-(3-(3-ethyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide | $^1$H NMR (400 MHz, DMSO-d$_6$) δ 11.23 (s, 1H), 8.14 (d, 1H, J = 4 Hz), 7.79 (dd, 1H, J = 1.6 and 10.4 Hz), 7.55 (d, 1H, J = 8.4 Hz), 7.41-7.37 (m, 1H), 7.31-7.23 (m, 3H), 6.94 (t, 1H, J = 8.8 Hz), 3.87 (q, 2H, J = 7.2 Hz), 3.37 (s, 2H), 3.08 (s, 3H), 2.59-2.55 (m, 1H), 1.18 (s, 3H), 1.11 (t, 3H, J = 9 Hz), 0.60-0.58 (m, 2H), 0.35-0.33 (m, 2H). MS: m/z 643.9 (M + 1)]. |
| 60 | 5 | 2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenoxy)-N-methylacetamide | $^1$H NMR (400 MHz, DMSO-d$_6$) δ 11.18 (s, 1H), 8.07-8.06 (d, 1H, J = 4 Hz), 7.79 (dd, 1H, J = 2 and 10.4 Hz), 7.56-7.54 (m, 1H), 7.40-7.36 (m, 1H), 7.04-7.01 (m, 3H), 6.93 (t, 1H, J = 8 Hz), 4.47 (s, 2H), 3.20 (s, 3H), 3.08 (s, 3H), 2.64 (d, 3H, J = 4 Hz), 1.23 (s, 3H). MS: m/z 616.1 (M + 1)]. |
| 61 | 1 | 3-(3-(3-ethyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide | $^1$HNMR (400 MHz, DMSO-d6), δ 11.25 (s, 1H), 7.79 (dd, J = 2 and 10.4 Hz, 1H), 7.55 (d, J = 8.4 Hz, 1H), 7.43-7.32 (m, 2H), 7.27-7.22 (m, 3H), 6.95 (t, J = 8.4 Hz, 1H). 6.79 (s, 1H), 3.87 (q, J = 7.2 Hz, 2H), 3.08 (s, 3H), 2.82 (t, J = 7.6 Hz, 2H), 2.38-2.35 (m, 2H), 1.19 (s, 3H), 1.13 (t, J = 7.2 Hz, 3H). MS: m/z 618.1 (M + 1)]. |
| 62 | 2 | N-cyclopropyl-3-(3-ethyl-5-((2-fluoro-4-iodophenyl)amino)-6,8-dimethyl-2,4,7-trioxo-3,4,6,7-tetrahydropyrido[4,3-d]pyrimidin-1(2H)-yl)benzamide | $^1$HNMR (400 MHz, DMSO-d6), δ 11.24 (s, 1H), 8.54 (d, J = 4.4 Hz, 1H), 7.87-7.78 (m, 3H), 7.61-7.52 (m, 3H), 6.97 (t, J = 8.8 Hz, 1H), 3.87 (q, J = 7.2 Hz, 2H), 3.08 (s, 3H), 2.86-2.81 (m, 1H), 1.17-1.08 (m, 6H), 0.70-0.68 (m, 2H), 0.58-0.57 (m, 2H). MS: m/z 630.1 (M + 1)]. |
| 63 | 7 | 5-((2-fluoro-4-iodophenyl)amino)-3,6,8-trimethyl-1-(3-(morpholine-4-carbonyl)phenyl) pyrido[4,3-d]pyrimidine-2,4,7(1H,3H,6H)-trione | $^1$HNMR (400 MHz, DMSO-d6), δ 11.17(s, 1H), 7.79 (d, J-10.4 Hz, 1H), 7.57-7.44 (m, 5H), 6.95 (t, J = 8.8 Hz, 1H), 3.62-3.36 (m, 8H), 3.21 (s, 3H), 3.09 (s, 3H), 1.21 (s, 3H). MS: m/z 645.9 (M + 1)]. |
| 64 | 2 | ethyl 2-(1-(3-(cyclopropylcarbamoyl)phenyl)-5-((2-fluoro-4-iodophenyl)amino)-6,8- | $^1$HNMR (400 MHz, DMSO-d6), δ 10.96 (s, 1H), 8.58 (d, J = 4.0 Hz, 1H), 7.89-7.78 (m, 3H), 7.60-7.54 (m, 3H), 7.03 (t, J = 8.4 Hz, 1H), 4.60 (s, 2H), 4.12 (q, J = 6.8 Hz, |

TABLE 4-continued

| Cmpd. | Intermed. No. | Name | Analytical data |
|---|---|---|---|
|  |  | dimethyl-2,4,7-trioxo-1,2,6,7-tetrahydropyrido[4,3-d]pyrimidin-3(4H)-yl)acetate | 2H), 3.08 (s, 3H), 2.87-2.82 (m, 1H), 1.24 (s, 3H), 1.19 (t, J = 4.8 Hz, 3H), 0.88-0.84 (m, 2H), 0.70 (m, 2H) |
| 65 | 8 | 1-(3-(1,1-dioxidothiomorpholine-4-carbonyl)phenyl)-5-((2-fluoro-4-iodophenyl)amino)-3,6,8-trimethylpyrido[4,3-d]pyrimidine-2,4,7(1H,3H,6H)-trione | $^1$HNMR (400 MHz, DMSO-d6), δ 11.17(s, 1H), 7.79 (dd, J = 2 & 10.4 Hz, 1H), 7.59-7.50 (m, 5H), 6.95 (t, J = 8.8 Hz, 1H), 4.00-3.69 (m, 4H), 3.38-3.26 (m, 4H), 3.22(s, 3H), 3.08 (s, 3H), 1.22 (s, 3H).<br>MS: m/z 694.0 (M + 1)] |
| 66 | 8 | 1-(3-(1,1-dioxidothiomorpholine-4-carbonyl)phenyl)-3-ethyl-5-((2-fluoro-4-iodophenyl)amino)-6,8-dimethylpyrido[4,3-d]pyrimidine-2,4,7(1H,3H,6H)-trione | $^1$HNMR (400 MHz, DMSO-d6), δ 11.20 (s, 1H), 7.79 (dd, J = 1.6 & 10.4 Hz, 1H), 7.61-7.51 (m, 5H), 6.97 (t, J = 8.4 Hz, 1H), 4.04-4.00 (m, 2H), 3.88 (q, J = 6.4 Hz, 2H), 3.69 (m, 2H), 3.28-3.27 (m, 4H), 3.08 (s, 3H), 1.21 (s, 3H), 1.16 (t, J = 6.4 Hz, 3H).<br>MS: m/z 708.0 (M + 1)]. |
| 67 | 10 | 2-(3-(3-ethyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N,N-dimethylacetamide | $^1$HNMR (400 MHz, DMSO-d6), δ 11.23 (s, 1H), 7.79 (dd, J = 1.6 & 10 Hz, 1H), 7.54 (d, J = 8.4 Hz, 1H), 7.42-7.22 (m, 4H), 6.95 (t, J = 8.8 Hz, 1H), 3.87 (q, J = 6.8 Hz, 2H), 3.73 (s, 2H), 3.08 (s, 3H), 2.99 (s, 3H), 2.82 (s, 3H), 1.21 (s, 3H), 1.11 (t, J = 7.2 Hz, 3H).<br>MS: m/z 632.5 (M + 1)]. |
| 68 | 1 | 3-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)propanamide | $^1$H NMR (400 MHz, DMSO-$d_6$) δ 11.20 (s, 1H), 7.79 (dd, J = 10.4 and 1.6 Hz, 1H), 7.54 (d, J = 8.4 Hz, 1H), 7.37 (t, J = 8.4 Hz, 1H), 7.31 (brs, 1H), 7.27-7.21 (m, 3H), 6.93 (t, J = 8.4 Hz, 1H), 6.77 (brs, 1H), 3.20 (s, 3H), 3.08 (s, 3H), 2.82 (t, J = 7.6 Hz, 2H), 2.36 (t, J = 7.2 Hz, 2H), 1.19 (s, 3H).<br>MS: m/z 604.1 (M + 1)]. |
| 69 | 2 | N-cyclopropyl-3-(5-((2-fluoro-4-iodophenyl)amino)-3-isopropyl-6,8-dimethyl-2,4,7-trioxo-3,4,6,7-tetrahydropyrido[4,3-d]pyrimidin-1(2H)-yl)benzamide | $^1$HNMR (400 MHz, DMSO-d6), δ 11.21 (s, 1H), 8.54-8.53 (d, 1H, J = 4 Hz), 7.86-7.77 (m, 3H), 7.59-7.52 (m, 3H), 6.99-6.95 (t, 1H, J = 8.8 Hz), 4.97-4.94 (m, 1H), 3.07 (s, 3H), 2.86-2.81 (m, 1H), 1.39-1.37 (m, 6H), 1.16 (s, 3H), 0.70-0.68 (m, 2H), 0.59-0.56 (m, 2H).<br>MS: m/z 644.1 (M + 1)]. |
| 70 | 2 | 3-(3-allyl-5-((2-fluoro-4-iodophenyl)amino)-6,8-dimethyl-2,4,7-trioxo-3,4,6,7-tetrahydropyrido[4,3-d]pyrimidin-1(2H)-yl)-N-cyclopropylbenzamide | $^1$HNMR (400 MHz, DMSO-d6), δ 11.16 (s, 1H), 8.54 (d, 1H, J = 4 Hz), 7.87-7.84 (m, 1H), 7.87-7.78 (m, 3H), 7.59-7.53 (m, 3H), 6.98 (t, 1H, J = 8.4 Hz), 5.85-5.80 (m, 1H), 5.19-5.10 (m, 1H ), 4.44 (d, 2H, J = 5.6 Hz), 3.08 (s, 3H), 2.85-2.81 (m, 1H), 1.18 (s, 3H), 0.70-0.68 (m, 2H), 0.58-0.57 (m, 2H).<br>MS: m/z 641.4 (M + 1)]. |
| 71 | 16 | 2-(3-(5-((2-fluoro-4-iodophenyl)amino)-6,8-dimethyl-3-(oxetan-3-yl)-2,4,7-trioxo-3,4,6,7-tetrahydropyrido[4,3-d]pyrimidin-1(2H)-yl)phenoxy)acetamide | $^1$HNMR (400 MHz, DMSO-d6), δ 11.05 (s, 1H), 7.56-7.49 (m, 2H), 7.41 (t, 1H, J = 8.0 Hz), 6.97-6.89 (m, 3H), 6.75 (t, 1H, J = 8.0 Hz), 6.51 (s, 1H), 5.72 (s, 1H), 5.03-5.01 (m, 1H), 4.90-4.82 (m, 2H), 4.52 (s, 2H), 4.14-4.08 (m, 2H), 3.21 (s, 3H), 1.44 (s, 3H).<br>MS: m/z 648.0 (M + 1)]. |
| 79 | 77 | 1-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)cyclopropanecarboxamide | $^1$HNMR (400 MHz, DMSO-d6), δ 11.19 (s, 1H), 7.79 (dd, J = 2 and 10.4 Hz, 1H), 7.55 (dd, J = 1.2 and 8.4 Hz, 1H), 7.46-7.32 (m, 4H), 7.33 (brs, 1H), 6.94 (t, J = 8.8 Hz, 1H), 6.09 (s, 1H), 3.21 (s, 3H), 3.09 (S, 3H), 1.35 (brs, 2H), 1.23 (s, 3H), 0.98 (brs 2H).<br>MS: m/z 616.0 (m + 1) |

Example 6: N-cyclopropyl-3-(3-(difluoromethyl)-5-((2-fluoro-4-iodophenyl)amino)-6,8-dimethyl-2,4,7-trioxo-3,4,6,7-tetrahydropyrido[4,3-d]pyrimidin-1(2H)-yl) benzamide (Compound 72)

Example 7: N-cyclopropyl-3-(3-(2,3-dihydroxypropyl)-5-((2-fluoro-4-iodophenyl)amino)-6,8-dimethyl-2,4,7-trioxo-3,4,6,7-tetrahydropyrido[4,3-d]pyrimidin-1(2H)-yl)benzamide (Compound 73)

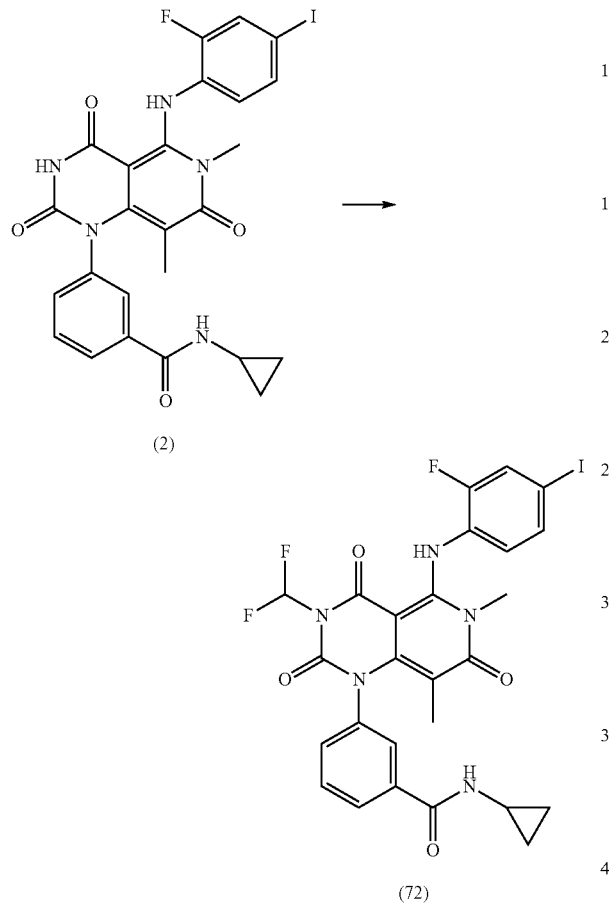

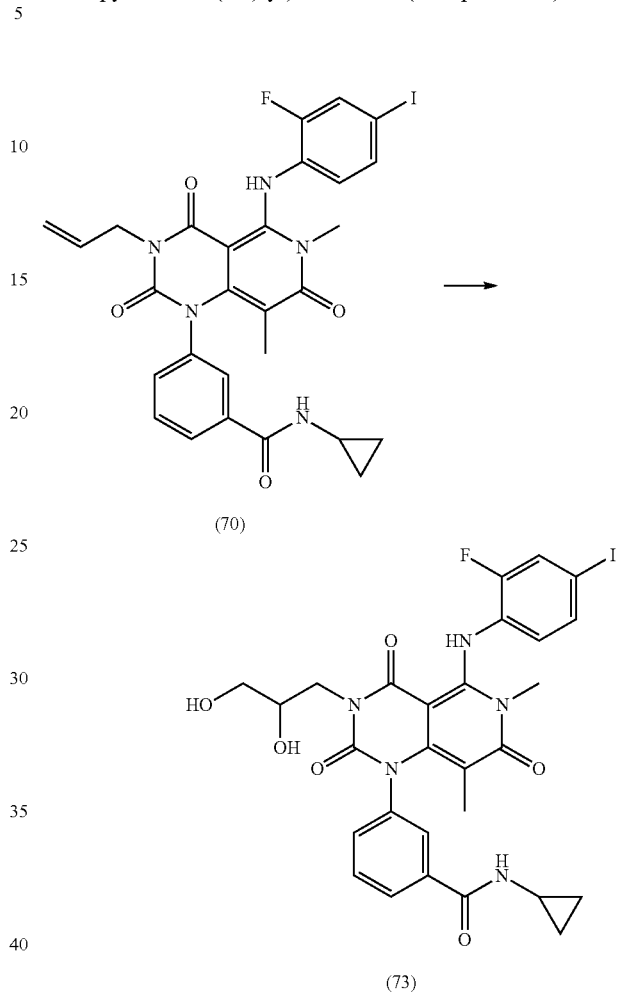

5 ml DMF was added to N-cyclopropyl-3-(5-((2-fluoro-4-iodophenyl)amino)-6,8-dimethyl-2,4,7-trioxo-3,4,6,7-tetrahydropyrido[4,3-d]pyrimidin-1(2H)-yl)benzamide (Compound 2) (200 mg, 0.333 mmol), to the mixture Potassium Carbonate (230 mg, 1.663 mmol) was added and the mixture was stirred at 60° C. for 20 min period and Sodium chlorodifluoroacetatae (101 mg, 0.665 mmol) was added and the mixture was heated at 90° C. for 18 hrs. The reaction mixture was cooled to room temperature followed by the addition of water and the mixture was extracted with ethyl acetate (3×10 ml). The combined organic layers were washed with water, brine and dried over sodium sulfate. The organic layer was concentrated to obtain a crude product, which was purified by column chromatography to yield the product (72) as solid (0.05 mg).

$^1$HNMR (400 MHz, DMSO-d6), δ 10.53 (s, 1H), 8.56-8.55 (d, 1H, J=4 Hz), 7.87-7.84 (m, 2H), 7.80-7.78 (m, 1H), 7.65-7.51 (m, 4H), 7.07-7.03 (t, 1H J=8 Hz), 3.09 (s, 3H), 2.85-2.82 (m, 1H), 1.19 (s, 3H), 0.70-0.68 (m, 2H), 0.59-0.58 (m, 2H).

MS: m/z 651.9 (M+1)].

To a stirred solution of 3-(3-allyl-5-((2-fluoro-4-iodophenyl)amino)-6,8-dimethyl-2,4,7-trioxo-3,4, 6,7-tetrahydropyrido[4,3-d]pyrimidin-1(2H)-yl)-N-cyclopropylbenzamide (compound 70) (180 mg, 0.281 mmol) and 4-methylmorpholine N-oxide (32.9 mg, 0.281 mmol) in THF (3 ml) was added osmium tetraoxide (10% in water) (0.088 ml, 0.281 mmol) slowly. Reaction was stirred at room temperature for 3 hrs. Water (20 mL) was added to the reaction mixture and the mixture was extracted with ethyl acetate (3×10 ml). The combined organic layers were washed with water, brine and dried over sodium sulfate. The organic layer was concentrated under vacuum to obtain a crude product, which was purified by column chromatography using a gradient of hexane-90% ethyl acetate in hexane eluent to yield the product (73) (100 mg).

$^1$H NMR (400 MHz, DMSO-d$_6$) δ 11.29 (s, 1H), 8.56 (d, 1H, J=4 Hz), 7.87-7.84 (m, 1H), 7.83-7.78 (m, 2H), 7.57-7.52 (m, 3H), 6.96 (t, 1H, J=8.8 Hz), 4.79 (d, 1H, J=5.6), 4.59 (t, 1H, J=5.6 Hz), 4.01-3.98 (m, 1H), 3.82-3.76 (m, 2H), 3.40-3.30 (m, 2H), 3.08 (s, 3H), 2.86-2.81 (m, 1H), 1.18 (s, 3H), 0.70-0.68 (m, 2H), 0.58-0.57 (m, 2H).

MS: m/z 676.1 (M+1)].

Example 8: 2-(1-(3-(cyclopropylcarbamoyl)phenyl)-5-((2-fluoro-4-iodophenyl)amino)-6,8-dimethyl-2,4,7-trioxo-1,2,6,7-tetrahydropyrido[4,3-d]pyrimidin-3(4H)-yl)acetic acid (Compound 74)

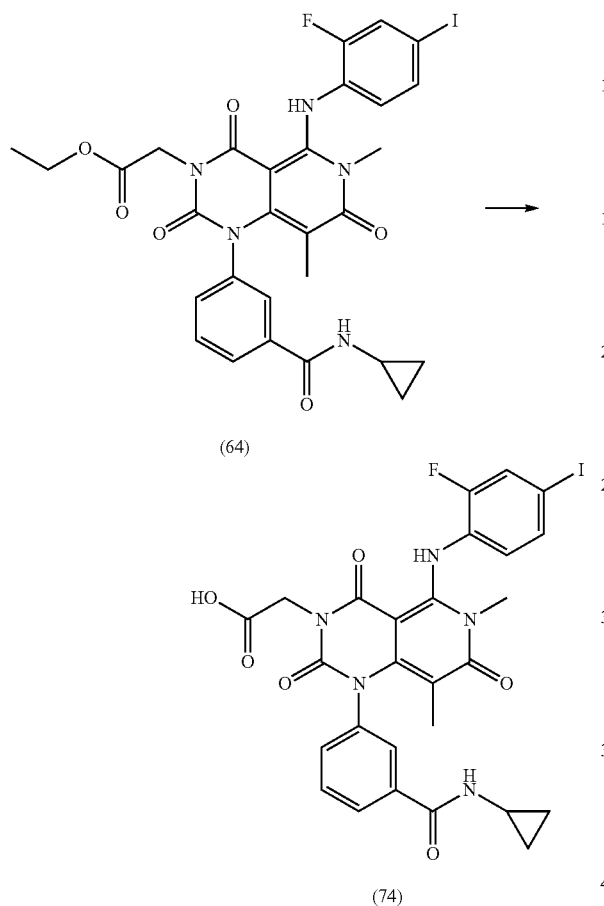

To a solution of ethyl 2-(1-(3-(cyclopropylcarbamoyl)phenyl)-5-((2-fluoro-4-iodophenyl)amino)-6,8-dimethyl-2,4,7-trioxo-1,2,6,7-tetrahydropyrido[4,3-d]pyrimidin-3(4H)-yl)acetate (compound 64) (66 mg, 0.096 mmol) in THF:Water (2 ml, 7:3) was added lithium hydroxide (8.06 mg, 0.192 mmol). The reaction mixture was stirred at room temperature for 3 h. Reaction mixture was concentrated under vacuum and treated with 2N HCl, the precipitate were collected by filtration and purified by flash chromatography to give the pure product (74) (28 mg).

$^1$HNMR (400 MHz, DMSO-d6), δ 13.09 (bs, 1H), 11.03 (s, 1H), 8.57 (d, J=4 Hz, 1H), 7.83 (m, 3H), 7.61-7.54 (m, 3H), 7.03 (t, J=8.8 Hz, 1H), 4.51 (s, 2H), 3.08 (s, 3H), 2.86-2.83 (m, 1H), 1.19 (s, 3H), 0.70-0.68 (m, 2H), 0.58-0.50 (m, 2H).
MS: m/z 659.9 (M+1)].

Example 9

Enantiomeric separation of 2-(3-(5-((2-Fluoro-4-iodophenyl)amino)-3,6,8-trimethyl-2,4,7-trioxo-3,4,6,7-tetrahydro pyrido[4,3-d]pyrimidin-1(2H)-yl)phenyl)-2-hydroxy acetamide (compound 47)

Compound 47 was enantiomerically separated by using the preparative HPLC by the methods described below.

Method-1
Column: CHIRAL PAK IA, 250 mm×4.6µ. Flow 1.5 ml/min, Mobile Phase: A=hexane: IPA (90:10% v/v, 0.1% DEA), B=MeOH:EtOH (1:1). A:B=60:40 v/v Method-2
Column: CHIRAL IA, 250 mm×4.6µ. Flow 1.5 ml/min, Mobile Phase: A=n-hexane: IPA (90:10% v/v, 0.1% DEA), B=MeOH:EtOH (1:1). A:B=85:15 v/v (R)-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)-2-hydroxyacetamide (Compound 75)

$^1$HNMR (400 MHz, DMSO-d6) δ 11.21 (s, 1H), 7.78 (dd, 1H, J=2 and 8.4 Hz), 7.55 (d, 1H, J=8.4 Hz), 7.48-7.33 (m, 5H), 7.22 (s, 1H), 6.93 (t, 1H, J=8.4 Hz), 6.15 (bs, 1H), 4.88 (d, 1H, J=4.8 Hz), 3.21 (s, 3H), 3.08 (s, 3H), 1.17 (s, 3H).
MS: m/z 606.1 (M+1)].
Retention time is 6.56.

(S)-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)-2-hydroxyacetamide (Compound 76)

$^1$H NMR (400 MHz, DMSO-d6) δ 11.21 (s, 1H), 7.78 (dd, 1H, J=2 and 8.4 Hz), 7.55 (dd, 1H, J=1.2 and 7.2 Hz), 7.48-7.33 (m, 5H), 7.22 (s, 1H), 6.93 (t, 1H, J=8.4 Hz), 6.15 (bs, 1H), 4.88 (d, 1H, J=4.8 Hz), 3.21 (s, 3H), 3.08 (s, 3H), 1.17 (s, 3H).
MS: m/z 606.1 (M+1)].
Retention time is 8.93.

Pharmacological Activity:
In-Vitro Experiments:

Example-A: Identification of Compounds Inhibiting MEK Kinase Activity

In a 25 µL reaction, MEK enzyme (final concentration 2-4 µg/ml), and ERK substrate (final concentration 50-100 µg/ml), were incubated with various concentration of test compounds (diluted such that the reaction had 1% DMSO), at 25-30° C. for 20 to 120 min on a shaker incubator. The reactions were initiated by the addition of ATP. The reactions were terminated by adding an equal volume of KinaseGlo reagent (Promega), following the manufacturer's instructions. The plates were read on a luminometer. IC$_{50}$ calculations were done using GraphPad Prism 5.

IC$_{50}$ values of the compounds of inventions were provided below in table 5. Compounds exhibiting IC$_{50}$ in the range 1 nM to 499 nM were grouped as 'a', compounds exhibiting IC$_{50}$ value in the range 0.5 µM to 1.5 µM were grouped as 'b', and the compounds exhibiting IC$_{50}$ value in the range 1.6 µM to 3.0 µM were grouped as 'c'.

TABLE 5

MEK kinase inhibition activity of the compounds (IC$_{50}$):

| Group | Compound No. |
|---|---|
| a | 1, 2, 4, 5, 6, 7, 8, 9, 10, 11, 12, 13, 14, 15, 16, 17, 18, 19, 20, 21, 23, 24, 26, 27, 28, 29, 30, 31, 32, 33, 34, 35, 37, 38, 39, 40, 41, 43, 44, 46, 48, 50, 54, 57, 58, 60, 61, 62, 63, 65, 66, 67, 68, 73, 76, 77, 78, 79 |
| b | 3, 25, 36, 42, 45, 47, 49, 51, 52, 55, 56, 59, 75. |
| c | 22, 53, 69, 71, 72, 74. |

Example-B: Analysis of ERK Phosphorylation

This assay was carried out with human melanoma cells, human and mouse colon cancer cells. Cells were treated for 1 h with various concentrations of test compounds. ERK phosphorylation analysis was performed using the Alphascreen SureFire Phospho-ERK 1/2 Kit (Perkin Elmer), by following the manufacturer's instructions. % inhibition of ERK phosphorylation was determined as:

100−{(RFU test−RFU lysis buffer control)/(RFU vehicle treated control−RFU lysis buffer control)}×100. The compounds prepared were tested using the above assay procedure and the results obtained are given in Table 6. Percentage inhibition at concentrations of 0.01 nM, 0.03 nM, 0.1-0.9 nM, 1 nM to 3 nM, 4-100 nM, and >100 nM, for the stated examples is setworth here. The percentage inhibiton at the above depicted concentrations for the compounds stated are given in the following groups.

TABLE 6

| Minimum concentration (nM) required for ≥80% inhibition of pERK | Compound No |
|---|---|
| 0.01 | 2, 6, 13, 31, 46, 49, 51, 66 |
| 0.03 | 35 |
| 0.1-0.9 | 5, 9, 10, 11, 17, 21, 24, 25, 28, 29, 38, 41, 42, 43, 44, 47, 60, 65, 67, 78, 77 |
| 1-3 | 1, 3, 4, 8, 15, 16, 20, 27, 30, 32, 33, 34, 36, 37, 39, 45, 48, 54, 56, 57, 58, 59, 61, 63, 68, 75 |
| 4-100 | 7, 12, 14, 18, 19, 22, 23, 26, 40, 50, 52, 53, 55, 62, 71, 72, 73, 76, 79 |
| >100 | 69, 74 |

Example-C: Analysis of B-Raf-Mediated MEK Phosphorylation

This assay was carried out with human melanoma cells. Cells were treated for 1 h with various concentrations of test compounds. MEK phosphorylation (S218 and S222) analysis was performed using the Alphascreen SureFire Phospho-MEK Kit (Perkin Elmer), by following the manufacturer's instructions. % inhibition of ERK phosphorylation was determined as:

100−{(RFU test−RFU lysis buffer control)/(RFU vehicle treated control−RFU lysis buffer control)}×100. The % inhibition of MEK phosphorylation at concentrations of 100 nM, 10 nM and 1 nM for some of the compounds of the present invention is showed in table-7.

TABLE 7

| Compound No. | Concentration (nM) | % Inhibition of MEK phosphorylation |
|---|---|---|
| Compound 2 | 100 | 96.4 |
| | 10 | 93.4 |
| | 1 | 72.2 |
| Compound 5 | 100 | 97.4 |
| | 10 | 97.4 |
| | 1 | 93.9 |
| Compound 16 | 100 | 94.71 |
| | 10 | 93.33 |
| | 1 | 89.24 |
| Compound 29 | 100 | 76.4 |
| | 10 | 72.9 |
| | 1 | 52.9 |
| Compound 37 | 100 | 92.39 |
| | 10 | 85.92 |
| | 1 | 54.69 |

TABLE 7-continued

| Compound No. | Concentration (nM) | % Inhibition of MEK phosphorylation |
|---|---|---|
| Compound 57 | 100 | 83.01 |
| | 10 | 76.44 |
| | 1 | 63.31 |
| Compound 77 | 100 | 85.5 |
| | 10 | 67.8 |
| | 1 | 49.0 |
| Compound 78 | 100 | 75.4 |
| | 10 | 56.7 |
| | 1 | 42.6 |

In-Vivo Experiments

Athymic nude mice were acclimatized in the experimental animal room for 15 days prior to the cell inoculation. Mice were inoculated subcutaneously at $5 \times 10^6$ COLO205/A375 cells (in 0.2 mL PBS) single cell suspension without conglomerates with viability of 98% into the right flank of the mice. Post cell inoculation, tumor dimension were measured with digimatic Vernier caliper (Mitutoyo, Japan) when tumor becomes palpable. Tumor volume was calculated by using the formula:

Tumor Volume in $Mm^3$(Length×Width×Width)/2

Mice were randomized on the basis of tumor volume into different groups with approximately equal mean and equal variation on desired day post cell inoculation. All groups were orally administered once/twice daily with some compounds of the invention and vehicle control for 21/22 days. Tumor measurements were done with Vernier caliper twice weekly. Body weights of mice were recorded daily.

Percentage change in body weight was calculated as per the following formula:

(Final body weight−Initial body weight)/(Initial body weight)×100

Percent tumor growth inhibition was calculated as:

$$= 1 - \left(\frac{(Tf - Ti)}{(Cf - Ci)}\right) \times 100$$

Where, Tf and Ti, are the final and initial treatment tumor volumes, and Cf and Ci are the final and initial control mean tumor volumes, respectively.

Percent tumor regression (TR %) was calculated as:

$$= \left(\frac{\text{(Final day tumor volume} - \text{Initial day tumor volume)}}{\text{(Initial day tumor volume)}}\right) \times 100$$

Data was analyzed by GraphPad Prism 5.00 software using Two-way ANOVA followed by Bonferroni post hoc test. Differences were considered significant at *$p<0.05$, $p<0.01$ and *$p<0.001$ treatment versus vehicle control group.

The compounds 2, 5, 9, and 35 were tested for tumor growth in Colo205 xenograft nude mice model using the assay procedure given above; the % of tumour growth inhibition after 20 days at 1 mg/kg dose was found to be in the range 60% to 100%.

The foregoing description is considered illustrative only of the principles of the disclosure. Further, since numerous modifications and changes will readily be apparent to those skilled in the art, it is not intended to limit the disclosure to the exact construction and process shown as described herein. Accordingly, all suitable modifications and equivalents may be resorted to as falling within the scope of the disclosure and as defined by the claims that follow.

The words "comprise", "comprising", "include" and "including" when used in this specification and in the following claims are intended to specify the presence of the stated features, integers, components, or steps, but they do not preclude the presence or addition of one or more additional features, integers, components, or steps thereof.

The invention claimed is:

1. A method for treatment of lung cancer in an individual in need thereof comprising administering to said individual an effective amount of a composition comprising a compound of formula (I), its tautomeric forms, its stereoisomers, or its pharmaceutically acceptable salts,

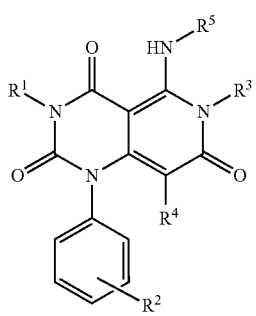

(I)

wherein:
$R^1$ is selected from the group consisting of hydrogen, substituted- or unsubstituted-alkyl, substituted- or unsubstituted-alkenyl, substituted- or unsubstituted-alkynyl, substituted- or unsubstituted-cycloalkyl, substituted- or unsubstituted-cycloalkenyl, substituted- or unsubstituted-aryl, substituted- or unsubstituted-heteroaryl, and substituted- or unsubstituted-heterocyclyl;
$R^2$ is selected from the group consisting of —(C(R$^c$)(R$^d$))$_m$—C(=O)—N(R$^6$)R$^7$, —C(=O)N(R$^8$)R$^9$ and —O—(C(R$^c$)(R$^d$))$_m$—C(=O)—N(R$^6$)R$^7$;
$R^3$ is selected from the group consisting of hydrogen, substituted- or unsubstituted-alkyl, and substituted- or unsubstituted-cycloalkyl;
$R^4$ is selected from the group consisting of hydrogen, halogen, substituted- or unsubstituted-alkyl, and substituted- or unsubstituted-cycloalkyl;
$R^5$ is substituted- or unsubstituted-aryl, wherein the substituents are selected from $R^a$ and $R^b$;
$R^6$ and $R^7$ are each independently selected from the group consisting of hydrogen, substituted- or unsubstituted-alkyl, substituted- or unsubstituted-cycloalkyl, and substituted- or unsubstituted-heterocyclyl; or $R^6$ and $R^7$ taken together with the nitrogen to which they are attached form a substituted- or unsubstituted-heterocycle;
$R^8$ and $R^9$ are each independently selected from the group consisting of hydrogen, substituted- or unsubstituted-cycloalkyl, and substituted- or unsubstituted-heterocyclyl, or $R^8$ and $R^9$ taken together with the nitrogen to which they are attached form a substituted- or unsubstituted-heterocycle;
with the provisos that both $R^8$ and $R^9$ cannot be hydrogen at the same time; and when $R^8$ and $R^9$ are not a part of a heterocycle formed together with the nitrogen to which they are attached, at least one of the $R^8$ and $R^9$ is substituted- or unsubstituted-cycloalkyl or substituted- or unsubstituted-heterocyclyl;
$R^a$ and $R^b$ are selected from the group consisting of hydrogen, halogen, and haloalkyl;
$R^c$ and $R^d$ are independently selected from the group consisting of hydrogen, halogen, hydroxyl, and substituted- or unsubstituted-alkyl; or $R^c$ and $R^d$ taken together with the carbon to which they are attached form a substituted- or unsubstituted-cycloalkyl;
m is an integer selected from the group consisting of 1, 2, 3, and 4;
further wherein:
when the alkyl group or alkenyl group is substituted, the alkyl group or alkenyl group is substituted with 1 to 4 substituents independently selected from the group consisting of oxo, halogen, nitro, cyano, perhaloalkyl, cycloalkyl, aryl, heteroaryl, heterocyclyl, —OR$^{10b}$, —SO$_2$R$^{10a}$, —C(=O)OR$^{10a}$, —OC(=O)R$^{10a}$, —C(=O)N(H)R$^{10}$, —OR$^{10a}$, —C(=O)N(alkyl)R$^{10}$, —N(H)C(=O)R$^{10a}$, —N(H)R$^{10}$, —N(alkyl)R$^{10}$—N(H)C(=O)N(H)R$^{10}$, —N(H)C(=O)N(alkyl)R$^{10}$, —NH—SO$_2$-alkyl, and —NH—SO$_2$-cycloalkyl;
when the cycloalkyl group or cycloalkenyl group is substituted, the cycloalkyl group or cycloalkenyl group is substituted with 1 to 3 substituents independently selected from the group consisting of oxo, halogen, nitro, cyano, alkyl, alkenyl, perhaloalkyl, hydroxyalkyl, aryl, heteroaryl, heterocyclyl, —OR$^{10b}$, —SO$_2$R$^{10a}$, —C(=O)R$^{10a}$, —C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, and —N(H)C(=O)N(alkyl)R$^{10}$, —NH—SO$_2$-alkyl, and —NH—SO$_2$-cycloalkyl;
when the aryl group is substituted, the aryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, —O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl, and —NH—SO$_2$-cycloalkyl;
when the heteroaryl group is substituted, the heteroaryl group is substituted with 1 to 3 substituents independently selected from the group consisting of halogen, nitro, cyano, hydroxy, alkyl, alkenyl, perhaloalkyl, cycloalkyl, cycloalkenyl, heterocycle, —O-alkyl, O-perhaloalkyl, —N(alkyl)alkyl, —N(H)alkyl, —NH$_2$, —SO$_2$-alkyl, —SO$_2$-perhaloalkyl, —N(alkyl)C(=O)alkyl, —N(H)C(=O)alkyl, —C(=O)N(alkyl)alkyl, —C(=O)N(H)alkyl, —C(=O)NH$_2$, —SO$_2$N(alkyl)alkyl, —SO$_2$N(H)alkyl, —SO$_2$NH$_2$, —NH—SO$_2$-alkyl, and —NH—SO$_2$-cycloalkyl;
when the heterocyclyl group is substituted, the heterocyclyl group is substituted with 1 to 3 substituents, when the heterocyclic group is substituted on a ring carbon of the 'heterocycle', the substituents are independently selected from the group consisting of halogen, nitro, cyano, oxo, alkyl, alkenyl, perhaloalkyl, cycloalkyl, cycloalkenyl, aryl, heteroaryl, heterocyclyl, —OR$^{10b}$, —C(=O)OR$^{10a}$, —OC(=O)R$^{10a}$, —C(=O)N(H)R$^{10}$, —C(=O)N(alkyl)R$^{10}$, —N(H)C(=O)R$^{10a}$, —N(H)R$^{10}$, —N(alkyl)R$^{10}$, —N(H)C(=O)N(H)R$^{10}$, —N(H)C(=O)N(alkyl)R$^{10}$; when the heterocyclic group is substituted on a ring nitrogen of the 'heterocycle', the substituents are independently selected from the group consisting of alkyl, alkenyl, cycloalkyl, cycloalkenyl, aryl, heteroaryl, —SO$_2$R$^{10a}$, —C(=O)R$^{10a}$, C(=O)OR$^{10a}$,
—C(=O)N(H)R$^{10}$, —C(=O)N(alkyl)R$^{10}$, —NH—SO$_2$-alkyl and —NH—SO$_2$-cycloalkyl; when the heterocyclic group is substituted on a ring sulfur of the 'heterocycle', the sulfur is substituted with 1 or 2 oxo groups;

R$^{10}$ is selected from the group consisting of hydrogen, alkyl, alkenyl, cycloalkyl, cycloalkenyl, aryl, heteroaryl, and heterocyclyl;

R$^{10a}$ is selected from the group consisting of alkyl, alkenyl, perhaloalkyl, cycloalkyl, cycloalkenyl, aryl, heteroaryl, and heterocyclyl; and R$^{10b}$ is selected from the group consisting of hydrogen, alkyl, alkenyl, perhaloalkyl, cycloalkyl, cycloalkenyl, aryl, heteroaryl, and heterocyclyl.

2. The method as claimed in claim 1, wherein R$^1$ is selected from the group consisting of hydrogen, substituted- or unsubstituted-alkyl, substituted- or unsubstituted-alkenyl, substituted- or unsubstituted-cycloalkyl, and substituted- or unsubstituted-heterocyclyl.

3. The method as claimed in claim 1, wherein R$^1$ is selected from the group consisting of hydrogen, methyl, ethyl, isopropyl, allyl, difluoromethyl, cyclopropyl, 3-oxetanyl, —CH$_2$COOC$_2$H$_5$, —CH$_2$CH(OH)CH$_2$(OH), and —C$_2$H$_4$OH.

4. The method as claimed in claim 1, wherein R$^3$ and R$^4$ are independently substituted- or unsubstituted-alkyl.

5. The method as claimed in claim 1, wherein R$^3$ and R$^4$ are methyl.

6. The method as claimed in claim 1, wherein R$^a$ and R$^b$ are independently hydrogen or halogen.

7. The method as claimed in claim 1, wherein R$^a$ and R$^b$ are independently fluorine or iodine.

8. The method as claimed in claim 1, wherein R$^c$ and R$^d$ are independently selected from the group consisting of hydrogen, substituted- or unsubstituted-alkyl, halogen, and hydroxyl; or R$^c$ and R$^d$ taken together with the carbon to which they are attached form a substituted- or unsubstituted-cycloalkyl ring.

9. The method as claimed in claim 1, wherein R$^c$ and R$^d$ are independently selected from the group consisting of hydrogen, methyl, fluoro, and hydroxyl; or R$^c$ and R$^d$ taken together with the carbon to which they are attached form cyclopropyl.

10. The method as claimed in claim 1, wherein m is 1 or 2.

11. The method as claimed in claim 1, wherein R$^6$ and R$^7$ are independently selected from the group consisting of hydrogen, substituted- or unsubstituted-alkyl, substituted- or unsubstituted-cycloalkyl, and substituted- or unsubstituted-heterocyclyl; or R$^6$ and R$^7$ taken together with the nitrogen atom to which they are attached form a substituted- or unsubstituted-heterocycle.

12. The method as claimed in claim 1, wherein R$^6$ and R$^7$ are independently selected from the group consisting of hydrogen, methyl, cyclopropyl, and 3-oxetane; or R$^6$ and R$^7$ are taken together with the nitrogen atom to which they are attached form azetidinyl or 3-hydroxyazetidinyl.

13. The method as claimed in claim 1, wherein R$^8$ and R$^9$ are independently selected from the group consisting of hydrogen, substituted- or unsubstituted-cycloalkyl and substituted- or unsubstituted-heterocyclyl; or R$^8$ and R$^9$ taken together with the nitrogen to which they are attached form a substituted- or unsubstituted-heterocycle; with the provisos that both R$^8$ and R$^9$ are not hydrogen at the same time, and when R$^8$ and R$^9$ are not a part of a heterocycle formed together with the nitrogen to which they are attached, at least one of the R$^8$ and R$^9$ is substituted- or unsubstituted-cycloalkyl or substituted- or unsubstituted-heterocyclyl.

14. The method as claimed in claim 1, wherein R$^8$ and R$^9$ are independently selected from the group consisting of hydrogen, cyclopropyl, cyclopropyl substituted with —C(=O)NH$_2$ or —CH$_2$OH, 3-oxetanyl, tetrahydrofuran-3-yl, and tetrahydro-2H-pyranyl, or R$^8$ and R$^9$ taken together with the nitrogen to which they are attached form 1,1-dioxidothiazolidinyl, 1,1-dioxidothiomorpholinyl, morpholinyl, azetidinyl, 1-pyrrolidinyl, piperazinyl, 4-methylpiperazinyl, 3-hydroxypyrrolidinyl or 4-hydroxypiperidinyl; with the provisos that both R$^8$ and R$^9$ are not hydrogen at the same time, and when R$^8$ and R$^9$ are not a part of a heterocycle formed together with the nitrogen to which they are attached, at least one of the R$^8$ and R$^9$ is substituted- or unsubstituted-cycloalkyl, or substituted- or unsubstituted-heterocyclyl.

15. The method as claimed in claim 1, wherein:
R$^1$ is selected from the group consisting of hydrogen, substituted- or unsubstituted-alkyl, substituted- or unsubstituted-alkenyl, and substituted- or unsubstituted-heterocyclyl;
R$^3$ and R$^4$ are independently substituted- or unsubstituted-alkyl;
R$^a$ and R$^b$ are independently hydrogen or halogen;
R$^c$ and R$^d$ are independently selected from the group consisting of hydrogen, substituted- or unsubstituted-alkyl, halogen, and hydroxyl, or R$^c$ and R$^d$ taken together with the carbon to which they are attached form a substituted- or unsubstituted-cycloalkyl ring;
m is 1 or 2;
R$^6$ and R$^7$ are independently selected from the group consisting of hydrogen, substituted- or unsubstituted-alkyl, substituted- or unsubstituted-cycloalkyl, and substituted- or unsubstituted-heterocyclyl; or R$^6$ and R$^7$ taken together with the nitrogen atom to which they are attached form a substituted- or unsubstituted-heterocycle;
R$^8$ and R$^9$ are independently selected from the group consisting of hydrogen, substituted- or unsubstituted-cycloalkyl and substituted- or unsubstituted-heterocyclyl, or R$^8$ and R$^9$ taken together with the nitrogen to which they are attached form a substituted- or unsubstituted-heterocycle; with the provisos that both R$^8$ and R$^9$ are not hydrogen at the same time, and when R$^8$ and R$^9$ are not a part of a heterocycle formed together with the nitrogen to which they are attached, at least one of the R$^8$ and R$^9$ is substituted- or unsubstituted-cycloalkyl or substituted- or unsubstituted-heterocyclyl.

16. The method as claimed in claim 1, wherein:
R$^1$ is selected from the group consisting of hydrogen, methyl, ethyl, isopropyl, allyl, difluoromethyl, cyclopropyl, 3-oxetanyl, —CH$_2$COOC$_2$H$_5$, —CH$_2$CH(OH)CH$_2$(OH), and —C$_2$H$_4$OH;
R$^3$ and R$^4$ are methyl;
R$^a$ and R$^b$ are independently hydrogen, fluorine or iodine;
R$^c$ and R$^d$ are independently selected from the group consisting of hydrogen, methyl, fluoro, and hydroxyl, or R$^c$ and R$^d$ taken together with the carbon to which they are attached form a substituted- or unsubstituted-cyclopropyl;

m is 1 or 2;

$R^6$ and $R^7$ are independently selected from the group consisting of methyl, cyclopropyl, and 3-oxetane; or $R^6$ and $R^7$ taken together with the nitrogen atom to which they are attached form azetidinyl or 3-hydroxyazetidinyl;

$R^8$ and $R^9$ are independently selected from the group consisting of hydrogen, cyclopropyl, cyclopropyl substituted with —C(=O)NH$_2$ or —CH$_2$OH, 3-oxetanyl, tetrahydrofuran-3-yl, and tetrahydro-2H-pyranyl, or $R^8$ and $R^9$ are taken together with the nitrogen to which they are attached form 1,1-dioxidothiazolidinyl, 1,1-dioxidothiomorpholinyl, morpholinyl, azetidinyl, 1-pyrrolidinyl, piperazinyl, 4-methylpiperazinyl, 3-hydroxypyrrolidinyl or 4-hydroxypiperidinyl; with the provisos that both $R^8$ and $R^9$ are not hydrogen at the same time, and when $R^8$ and $R^9$ are not a part of a heterocycle formed together with the nitrogen to which they are attached, at least one of the $R^8$ and $R^9$ is substituted- or unsubstituted-cycloalkyl or substituted- or unsubstituted-heterocyclyl.

17. The method as claimed in claim 1, wherein a compound is selected from the group consisting of:

3-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide;

N-cyclopropyl-3-(5-((2-fluoro-4-iodophenyl)amino)-6,8-dimethyl-2,4,7-trioxo-3,4,6,7-tetrahydropyrido[4,3-d]pyrimidin-1(2H)-yl)benzamide;

1-(3-(azetidine-1-carbonyl)phenyl)-5-((2-fluoro-4-iodophenyl)amino)-6,8-dimethylpyrido[4,3-d]pyrimidine-2,4,7(1H,3H,6H)-trion;

N-cyclopropyl-2-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide;

2-(3-(5-((2-fluoro-4-iodophenyl)amino)-6,8-dimethyl-2,4,7-trioxo-3,4,6,7-tetrahydro pyrido[4,3-d]pyrimidin-1(2H)-yl)phenoxy)-N-methylacetamide;

N-cyclopropyl-2-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenoxy)acetamide;

5-((2-fluoro-4-iodophenyl)amino)-6,8-dimethyl-1-(3-(morpholine-4-carbonyl)phenyl) pyrido[4,3-d]pyrimidine-2,4,7(1H,3H,6H)-trione;

1-(3-(1,1-dioxidothiomorpholine-4-carbonyl)phenyl)-5-((2-fluoro-4-iodophenyl)amino)-6,8-dimethylpyrido[4,3-d]pyrimidine-2,4,7(1H,3H,6H)-trione;

2-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-2-methylpropanamide;

2-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N,N-dimethylacetamide;

N-(1-carbamoylcyclopropyl)-3-(5-((2-fluoro-4-iodophenyl)amino)-6,8-dimethyl-2,4,7-trioxo-3,4,6,7-tetrahydropyrido[4,3-d]pyrimidin-1(2H)-yl)benzamide;

3-(5-((2-fluoro-4-iodophenyl)amino)-6,8-dimethyl-2,4,7-trioxo-3,4,6,7-tetrahydropyrido[4,3-d]pyrimidin-1(2H)-yl)-N-(tetrahydro-2H-pyran-4-yl)benzamide;

2-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-2-hydroxyacetamide;

3-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N-methylpropanamide;

2-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenoxy)acetamide;

1-(3-(1,1-dioxidothiazolidine-3-carbonyl)phenyl)-5-((2-fluoro-4-iodophenyl)amino)-6,8-dimethylpyrido[4,3-d]pyrimidine-2,4,7(1H,3H,6H)-trione;

5-((2-fluoro-4-iodophenyl)amino)-1-(3-(4-hydroxypiperidine-1-carbonyl)phenyl)-6,8-dimethylpyrido[4,3-d]pyrimidine-2,4,7(1H,3H,6H)-trione;

N-cyclopropyl-3-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide;

2-(3-(5-((2-fluoro-4-iodophenyl)amino)-6,8-dimethyl-2,4,7-trioxo-3,4,6,7-tetrahydropyrido[4,3-d]pyrimidin-1(2H)-yl)phenoxy)-2-methylpropanamide;

5-((2-fluoro-4-iodophenyl)amino)-6,8-dimethyl-1-(3-(4-methylpiperazine-1-carbonyl) phenyl)pyrido[4,3-d]pyrimidine-2,4,7(1H,3H,6H)-trione;

5-((2-fluoro-4-iodophenyl)amino)-1-(3-(3-hydroxypyrrolidine-1-carbonyl)phenyl)-6,8-dimethylpyrido[4,3-d]pyrimidine-2,4,7(1H,3H,6H)-trione;

5-((2-fluoro-4-iodophenyl)amino)-6,8-dimethyl-1-(3-(piperazine-1-carbonyl)phenyl)pyrido[4,3-d]pyrimidine-2,4,7(1H,3H,6H)-trione;

1-(3-(azetidine-1-carbonyl)phenyl)-3-cyclopropyl-5-((2-fluoro-4-iodophenyl)amino)-6,8-dimethylpyrido[4,3-d]pyrimidine-2,4,7(1H,3H,6H)-trione;

N-cyclopropyl-2-(3-(3-cyclopropyl-5-((2-fluoro-4-iodophenyl)amino)-6,8-dimethyl-2,4,7-trioxo-3,4,6, 7-tetrahydropyrido[4,3-d]pyrimidin-1(2H)-yl)phenoxy)acetamide;

2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide;

3-cyclopropyl-5-((2-fluoro-4-iodophenyl)amino)-6,8-dimethyl-1-(3-(pyrrolidine-1-carbonyl)phenyl)pyrido[4,3-d]pyrimidine-2,4,7(1H,3H,6H)-trione;

2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-2-methylpropanamide;

2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N,N-dimethylacetamide;

2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N-(oxetan-3-yl)acetamide;

2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-2-hydroxyacetamide;

3-cyclopropyl-5-((2-fluoro-4-iodophenyl)amino)-1-(3-(2-(3-hydroxyazetidin-1-yl)-2-oxo ethyl)phenyl)-6,8-dimethylpyrido[4,3-d]pyrimidine-2,4,7(1H,3H,6H)-trione;

3-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide;

2-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenoxy)acetamide;

3-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N-methylpropanamide;

N-cyclopropyl-3-(3-cyclopropyl-5-((2-fluoro-4-iodophenyl)amino)-6,8-dimethyl-2,4,7-trioxo-3,4,6, 7-tetrahydropyrido[4,3-d]pyrimidin-1(2H)-yl)benzamide;

3-cyclopropyl-1-(3-(1,1-dioxidothiazolidine-3-carbonyl) phenyl)-5-((2-fluoro-4-iodophenyl)amino)-6,8-dimethylpyrido[4,3-d]pyrimidine-2,4,7(1H,3H,6H)-trione;

3-cyclopropyl-1-(3--(1,1-dioxidothiomorpholine-4-carbonyl)phenyl)-5-((2-fluoro-4-iodo phenyl)amino)-6,8-dimethylpyrido[4,3-d]pyrimidine-2,4,7(1H,3H,6H)-trione;

N-cyclopropyl-3-(3-(3-cyclopropyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl) propanamide;

N-cyclopropyl-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenoxy)acetamide;

2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)acetamide;

2-(3-(5-((2-fluoro-4-iodophenyl)amino)-3,6,8-trimethyl-2,4,7-trioxo-3,4,6,7-tetra hydropyrido[4,3-d]pyrimidin-1(2H)-yl)phenyl)-2-methylpropanamide;

2-(3-(5-((2-fluoro-4-iodophenyl)amino)-3,6,8-trimethyl-2,4,7-trioxo-3,4,6,7-tetra hydropyrido[4,3-d]pyrimidin-1(2H)-yl)phenyl)-N,N-dimethylacetamide;

2,2-difluoro-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)acetamide;

1-(3-(2-(azetidin-1-yl)-2-oxoethyl)phenyl)-5-((2-fluoro-4-iodophenyl)amino)-3,6,8-trimethylpyrido[4,3-d]pyrimidine-2,4,7(1H,3H,6H)-trione;

2-(3-(5-((2-fluoro-4-iodophenyl)amino)-3,6,8-trimethyl-2,4,7-trioxo-3,4,6,7-tetra hydropyrido[4,3-d]pyrimidin-1(2H)-yl)phenyl)-2-hydroxyacetamide;

5-((2-fluoro-4-iodophenyl)amino)-1-(3-(2-(3-hydroxyazetidin-1-yl)-2-oxoethyl) phenyl)-3,6,8-trimethylpyrido[4,3-d]pyrimidine-2,4,7(1H,3H,6H)-trione;

3-(5-((2-fluoro-4-iodophenyl)amino)-3,6,8-trimethyl-2,4,7-trioxo-3,4,6,7-tetra hydropyrido[4,3-d]pyrimidin-1(2H)-yl)-N-(oxetan-3-yl)benzamide;

2-(3-(5-((2-fluoro-4-iodophenyl)amino)-3,6,8-trimethyl-2,4,7-trioxo-3,4,6,7-tetra hydropyrido[4,3-d]pyrimidin-1(2H)-yl)phenyl)-N-(oxetan-3-yl)acetamide;

3-(5-((2-fluoro-4-iodophenyl)amino)-3,6,8-trimethyl-2,4,7-trioxo-3,4,6,7-tetra hydropyrido[4,3-d]pyrimidin-1(2H)-yl)-N-(tetrahydrofuran-3-yl)benzamide;

3-(5-((2-fluoro-4-iodophenyl)amino)-3,6,8-trimethyl-2,4,7-trioxo-3,4,6,7-tetrahydropyrido[4,3-d]pyrimidin-1(2H)-yl)-N-(tetrahydro-2H-pyran-4-yl)benzamide;

3-(5-((2-fluoro-4-iodophenyl)amino)-3,6,8-trimethyl-2,4,7-trioxo-3,4,6,7-tetrahydropyrido[4,3-d]pyrimidin-1(2H)-yl)-N-(1-(hydroxymethyl)cyclopropyl) benzamide;

N-cyclopropyl-3-(5-((2-fluoro-4-iodophenyl)amino)-3,6,8-trimethyl-2,4,7-trioxo-3,4,6,7-tetrahydropyrido[4,3-d]pyrimidin-1(2H)-yl)benzamide;

N-cyclopropyl-3-(5-((2-fluoro-4-iodophenyl)amino)-3-(2-hydroxyethyl)-6,8-dimethyl-2,4,7-trioxo-3,4,6,7-tetrahydropyrido[4,3-d]pyrimidin-1(2H)-yl)benzamide;

1-(3-(azetidine-1-carbonyl)phenyl)-5-((2-fluoro-4-iodophenyl)amino)-3,6,8-trimethylpyrido[4,3-d]pyrimidine-2,4,7(1H,3H,6H)-trione;

2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenoxy)acetamide;

N-cyclopropyl-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)acetamide;

N-cyclopropyl-2-(3-(3-ethyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)acetamide;

2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenoxy)-N-methylacetamide;

3-(3-(3-ethyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)propanamide;

N-cyclopropyl-3-(3-ethyl-5-((2-fluoro-4-iodophenyl)amino)-6,8-dimethyl-2,4,7-trioxo-3,4,6,7-tetrahydropyrido[4,3-d]pyrimidin-1(2H)-yl)benzamide;

5-((2-fluoro-4-iodophenyl)amino)-3,6,8-trimethyl-1l-(3-(morpholine-4-carbonyl)phenyl)pyrido[4,3-d]pyrimidine-2,4,7(1H,3H, 6H)-trione;

1-(3-(1,1-dioxidothiomorpholine-4-carbonyl)phenyl)-5-((2-fluoro-4-iodophenyl)amino)-3,6,8-trimethylpyrido[4,3-d]pyrimidine-2,4,7(1H,3H,6H)-trione;

1-(3-(1,1-dioxidothiomorpholine-4-carbonyl)phenyl)-3-ethyl-5-((2-fluoro-4-iodophenyl)amino)-6,8-dimethylpyrido[4,3-d]pyrimidine-2,4,7(1H,3H,6H)-trione;

2-(3-(3-ethyl-5-((2-fluoro-4-iodophenyl)amino)-6,8-dimethyl-2,4,7-trioxo-3,4,6,7-tetrahydropyrido[4,3-d]pyrimidin-1(2H)-yl)phenyl)-N,N-dimethylacetamide;

3-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)propanamide;

N-cyclopropyl-3-(5-((2-fluoro-4-iodophenyl)amino)-3-isopropyl-6,8-dimethyl-2,4,7-trioxo-3,4,6,7-tetrahydropyrido[4,3-d]pyrimidin-1(2H)-yl)benzamide;

2-(3-(5-((2-fluoro-4-iodophenyl)amino)-6,8-dimethyl-3-(oxetan-3-yl)-2,4,7-trioxo-3,4,6,7-tetrahydropyrido[4,3-d]pyrimidin-1(2H)-yl)phenoxy)acetamide;

N-cyclopropyl-3-(3-(difluoromethyl)-5-((2-fluoro-4-iodophenyl)amino)-6,8-dimethyl-2,4,7-trioxo-3,4,6,7-tetrahydropyrido[4,3-d]pyrimidin-1(2H)-yl)benzamide;

N-cyclopropyl-3-(3-(2,3-dihydroxypropyl)-5-((2-fluoro-4-iodophenyl)amino)-6,8-dimethyl-2,4,7-trioxo-3,4,6,7-tetrahydropyrido[4,3-d]pyrimidin-1(2H)-yl)benzamide;

(R)-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)-2-hydroxyacetamide;

(S)-2-(3-(5-((2-fluoro-4-iodophenyl)amino)-3,6,8-trimethyl-2,4,7-trioxo-3,4,6,7-tetrahydropyrido[4,3-d]pyrimidin-1(2H)-yl)phenyl)-2-hydroxyacetamide;

1-(3-(5-((2-fluoro-4-iodo phenyl)amino)-6,8-dimethyl-2,4,7-trioxo-3,4,6,7-tetra hydropyrido[4,3-d] pyrimidin-1(2H)-yl)phenyl) cyclopropanecarboxamide;

1-(3-(3-cyclopropyl-5-((2-fluoro-4-iodophenyl) amino)-6,8-dimethyl-2,4,7-trioxo-3,4,6,7-tetra hydropyrido[4,3-d] pyrimidin-1(2H)-yl) phenyl)cyclopropane carboxamide; and 1-(3-(5-((2-fluoro-4-iodophenyl)amino)-3,6,8-trimethyl-2,4,7-trioxo-3,4,6,7-tetrahydro pyrido[4,3-d]pyrimidin-1(2H)-yl)phenyl)cyclopropanecarboxamide.

* * * * *

UNITED STATES PATENT AND TRADEMARK OFFICE
CERTIFICATE OF CORRECTION

PATENT NO. : 9,969,731 B2
APPLICATION NO. : 15/388327
DATED : May 15, 2018
INVENTOR(S) : Bhavesh Dave et al.

It is certified that error appears in the above-identified patent and that said Letters Patent is hereby corrected as shown below:

In the Claims

In Column 95, Line 34, replace "2,4,7(1H,3H,6H)-trion;" with --2,4,7(1H,3H,6H)-trione;--

In Column 97, Line 16, replace "5-((2-fluoro-4-iodophenyl)amino)-3,6,8-trimethyl-1l-(3-" with --5-((2-fluoro-4-iodophenyl)amino)-3,6,8-trimethyl-1-(3- --

Signed and Sealed this
Twenty-first Day of August, 2018

Andrei Iancu
*Director of the United States Patent and Trademark Office*